US012529072B2

(12) United States Patent
Hunt et al.

(10) Patent No.: US 12,529,072 B2
(45) Date of Patent: Jan. 20, 2026

(54) TRANSCRIPTION MODULATION IN ANIMALS USING CRISPR/CAS SYSTEMS

(71) Applicant: Regeneron Pharmaceuticals, Inc., Tarrytown, NY (US)

(72) Inventors: Charleen Hunt, Dumont, NJ (US); Suzanne Hartford, Putnam Valley, NY (US); Guochun Gong, Pleasantville, NY (US); Brian Zambrowicz, Sleepy Hollow, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 713 days.

(21) Appl. No.: 18/051,659

(22) Filed: Nov. 1, 2022

(65) Prior Publication Data

US 2023/0123296 A1 Apr. 20, 2023

Related U.S. Application Data

(62) Division of application No. 16/358,395, filed on Mar. 19, 2019, now Pat. No. 11,519,004.

(Continued)

(51) Int. Cl.
*A01K 67/0278* (2024.01)
*A01K 67/0275* (2024.01)

(Continued)

(52) U.S. Cl.
CPC ...... *C12N 15/8509* (2013.01); *A01K 67/0275* (2013.01); *C12N 9/22* (2013.01); *C12N 15/113* (2013.01); *C12N 15/86* (2013.01); *C12N 15/907* (2013.01); *A01K 2217/07* (2013.01); *A01K 2217/072* (2013.01); *A01K 2217/206* (2013.01); *A01K 2227/105* (2013.01); *A01K 2267/03* (2013.01); *A01K 2267/0306* (2013.01);

(Continued)

(58) Field of Classification Search
None
See application file for complete search history.

(56) References Cited

U.S. PATENT DOCUMENTS 5,942,435 A 8/1999 Wheeler
6,586,251 B2 7/2003 Economides et al.

(Continued)

FOREIGN PATENT DOCUMENTS

EP 3045537 A1 7/2016
EP 30644585 A1 9/2016

(Continued)

OTHER PUBLICATIONS

Hunt et al., "Tissue-specific activation of gene expression by the Synergistic Activation Mediator (SAM) CRISPRa system in mice," Nat. Commun., 12(1):2770, (May 13, 2021).

(Continued)

*Primary Examiner* — Arthur S Leonard
(74) *Attorney, Agent, or Firm* — Alston & Bird LLP

(57) ABSTRACT

Non-human animal cells and non-human animals comprising CRISPR/Cas synergistic activation mediator system components and methods of making and using such non-human animal cells and non-human animals are provided. Methods are provided for using such non-human animals to increase expression of target genes in vivo and to assess CRISPR/Cas synergistic activation mediator systems for the ability to increase expression of target genes in vivo.

29 Claims, 22 Drawing Sheets

Specification includes a Sequence Listing.

Related U.S. Application Data

(60) Provisional application No. 62/644,961, filed on Mar. 19, 2018.

(51) Int. Cl.

| | |
|---|---|
| ***C12N 9/22*** | (2006.01) |
| ***C12N 15/113*** | (2010.01) |
| ***C12N 15/85*** | (2006.01) |
| ***C12N 15/86*** | (2006.01) |
| ***C12N 15/90*** | (2006.01) |

(52) U.S. Cl.

CPC ................ *A01K 2267/0362* (2013.01); *C12N 2015/8527* (2013.01); *C12N 2310/20* (2017.05); *C12N 2310/531* (2013.01); *C12N 2320/11* (2013.01); *C12N 2750/14143* (2013.01); *C12N 2800/30* (2013.01); *C12N 2830/008* (2013.01)

(56) References Cited

U.S. PATENT DOCUMENTS

| | | | |
|---|---|---|---|
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 10,329,582 | B2 | 6/2019 | Lee et al. |
| 10,385,359 | B2 | 8/2019 | Lee et al. |
| 10,550,372 | B2 | 2/2020 | Konermann et al. |
| 10,577,630 | B2 | 3/2020 | Zhang et al. |
| 10,760,064 | B2 | 9/2020 | Joung et al. |
| 11,001,829 | B2 | 5/2021 | Zhang et al. |
| 11,519,004 | B2 | 12/2022 | Hunt et al. |
| 11,597,919 | B2 | 3/2023 | Konermann et al. |
| 2008/0078000 | A1 | 3/2008 | Poueymirou et al. |
| 2014/0178879 | A1 | 6/2014 | Economides et al. |
| 2014/0235933 | A1 | 8/2014 | Lee et al. |
| 2014/0310828 | A1 | 10/2014 | Lee et al. |
| 2015/0071899 | A1 | 3/2015 | Liu et al. |
| 2015/0376628 | A1 | 12/2015 | Schoenherr et al. |
| 2015/0376651 | A1 | 12/2015 | Frendewey et al. |
| 2016/0058889 | A1 | 3/2016 | Olson et al. |
| 2016/0145646 | A1 | 5/2016 | Frendewey et al. |
| 2016/0151491 | A1 | 6/2016 | Rabinovich et al. |
| 2016/0208288 | A1 | 7/2016 | Liu et al. |
| 2016/0222416 | A1 | 8/2016 | Church et al. |
| 2016/0237456 | A1 | 8/2016 | Church et al. |
| 2016/0243260 | A1 | 8/2016 | Blits |
| 2016/0257974 | A1 | 9/2016 | Bradley et al. |
| 2016/0281072 | A1 | 9/2016 | Zhang |
| 2016/0326548 | A1 | 11/2016 | Cost |
| 2016/0355797 | A1 | 12/2016 | Konermann et al. |
| 2017/0107536 | A1 | 4/2017 | Zhang et al. |
| 2017/0204407 | A1 | 7/2017 | Gilbert et al. |
| 2017/0239370 | A1 | 8/2017 | Zhu et al. |
| 2018/0057810 | A1 | 3/2018 | Zhang et al. |
| 2018/0110877 | A1 | 4/2018 | Wilson et al. |
| 2018/0119122 | A1 | 5/2018 | Zhang et al. |
| 2018/0179553 | A1 | 6/2018 | Watson et al. |
| 2018/0185516 | A1 | 7/2018 | Ansell et al. |
| 2019/0002869 | A1 | 1/2019 | Yin et al. |
| 2019/0032053 | A1 | 1/2019 | Ji et al. |
| 2019/0038780 | A1 | 2/2019 | Largaespada et al. |
| 2019/0106693 | A1 | 4/2019 | Rinn et al. |
| 2019/0233814 | A1 | 8/2019 | Zhang et al. |
| 2019/0284572 | A1 | 9/2019 | Hunt et al. |
| 2019/0365924 | A1 | 12/2019 | Conway et al. |
| 2019/0376060 | A1 | 12/2019 | Vora et al. |
| 2019/0376090 | A1 | 12/2019 | Joung et al. |
| 2019/0390195 | A1 | 12/2019 | Tondera et al. |
| 2020/0115687 | A1 | 4/2020 | Konermann et al. |
| 2020/0248168 | A1 | 8/2020 | Lundberg et al. |
| 2020/0392541 | A1 | 12/2020 | Zhang et al. |
| 2021/0079394 | A1 | 3/2021 | Hunt et al. |
| 2021/0102206 | A1 | 4/2021 | Liao et al. |
| 2021/0269831 | A1 | 9/2021 | Zhang et al. |
| 2024/0002839 | A1 | 1/2024 | Drummond Samuelson et al. |
| 2024/0035007 | A1 | 2/2024 | Konermann et al. |

FOREIGN PATENT DOCUMENTS

| | | | |
|---|---|---|---|
| EP | 2877571 | B1 | 5/2018 |
| EP | 3392337 | A1 | 10/2018 |
| EP | 3620524 | A1 | 10/2018 |
| EP | 3003392 | B1 | 10/2019 |
| EP | 3080271 | B1 | 2/2020 |
| WO | WO 2001/005962 | A2 | 1/2001 |
| WO | WO 2013/071440 | A1 | 5/2013 |
| WO | WO 2014/093622 | A2 | 6/2014 |
| WO | WO 2014/093655 | A2 | 6/2014 |
| WO | WO 2014/093701 | A1 | 6/2014 |
| WO | WO 2014/130706 | A1 | 8/2014 |
| WO | WO 2014/172489 | A2 | 10/2014 |
| WO | WO 2014/197568 | A2 | 12/2014 |
| WO | WO 2015/006294 | A2 | 1/2015 |
| WO | WO 2015/035139 | A2 | 3/2015 |
| WO | WO 2015/040075 | A1 | 3/2015 |
| WO | WO 2015/042557 | A1 | 3/2015 |
| WO | WO 2015/088643 | A1 | 6/2015 |
| WO | WO 2015/089486 | A2 | 6/2015 |
| WO | WO 2015/200334 | A1 | 12/2015 |
| WO | WO 2015/200805 | A2 | 12/2015 |
| WO | WO 2016/044745 | A1 | 3/2016 |
| WO | WO 2016/049258 | A2 | 3/2016 |
| WO | WO 2016/081923 | A2 | 5/2016 |
| WO | WO 2016/094872 | A1 | 6/2016 |
| WO | WO 2016/094874 | A1 | 6/2016 |
| WO | WO 2016/137949 | A1 | 9/2016 |
| WO | WO 2016/149484 | A2 | 9/2016 |
| WO | WO 2016/176191 | A1 | 11/2016 |
| WO | WO 2017/011721 | A1 | 1/2017 |
| WO | WO 2017/087780 | A1 | 5/2017 |
| WO | WO 2017/106657 | A1 | 6/2017 |
| WO | WO 2017/173054 | A1 | 10/2017 |
| WO | WO 2017/180915 | A2 | 10/2017 |
| WO | WO 2018/007871 | A1 | 1/2018 |
| WO | WO 2018/009869 | A1 | 1/2018 |
| WO | WO 2018/085644 | A1 | 5/2018 |
| WO | WO 2018/096343 | A1 | 5/2018 |
| WO | WO 2018/107026 | A1 | 6/2018 |
| WO | WO 2018/107028 | A1 | 6/2018 |
| WO | WO 2018/119354 | A1 | 6/2018 |
| WO | WO 2018/154380 | A1 | 8/2018 |
| WO | WO 2019/027728 | A1 | 2/2019 |
| WO | WO 2019/183123 | A1 | 9/2019 |
| WO | WO 2019/236081 | A1 | 12/2019 |
| WO | WO 2019/237069 | A1 | 12/2019 |
| WO | WO 2019/246203 | A1 | 12/2019 |
| WO | WO 2020/142714 | A1 | 7/2020 |
| WO | WO 2021/108363 | A1 | 6/2021 |

OTHER PUBLICATIONS

Omer, et al., "CRISPR Correction of a Homozygous Low-Density Lipoprotein Receptor Mutation in Familial Hypercholesterolemia Induced Pluripotent Stem Cells," Hepatol. Commun., 1(9):886-898, (Oct. 16, 2017).

Yin, et al., "Structure-guided chemical modification of guide RNA enables potent non-viral in vivo genome editing," Nat. Biotechnol., 35(12):1179-1187, (Nov. 13, 2017).

Addgene Product Catalogue, plasmid #61425, pp. 10-13, retrieved at www.addgene.org/61425/ on Apr. 26, 2022, (2022).

Baeumler, et al., "Engineering Synthetic Signaling Pathways with Programmable dCas9-Based Chimeric Receptors," Cell Rep., 20(11):2639-2653, (2017).

Barthold, "Genetically altered mice: phenotypes, no phenotypes, and Faux phenotypes," Genetica, 122(1):75-88, (2004).

Birling, et al., "Modeling human disease in rodents by CRISPR/Cas9 genome editing," Mamm. Genome, 28(7-8):291-301, (2017).

Brevini, et al., "No shortcuts to pig embryonic stem cells," Theriogenology, 74(4):544-550, (2010).

(56) References Cited

OTHER PUBLICATIONS

Brevini, et al., "Porcine embryonic stem cells: Facts, challenges and hopes," Theriogenology, 68 Suppl. 1:S206-S213, (2007).
Burova, et al., "Characterization of the Anti-PD-1 Antibody REGN2810 and Its Antitumor Activity in Human PD-1 Knock-In Mice," Mol. Cancer Ther., 16(5):861-870, (2017).
Cao, et al., "Isolation and Culture of Primary Bovine Embryonic Stem Cell Colonies by a Novel Method," J. Exp. Zool. A. Ecol. Genet. Physiol., 311(5):368-376, (2009).
Cas9 SAM, "Cas9-Activators with SAM" [Retrieved from the Internet Oct. 19, 2017 <http://sam.genone-engineering.org/>].
Chavez, et al., "Comparison of Cas9 activators in multiple species," Nat. Methods, 13(7):563-567, (2016).
Chow et al., "AAV-mediated direct in vivo CRISPR screen identifies functional suppressors in glioblastoma," Nat. Neurosci. 20(10):1329-1341 plus supplementary materials, (Aug. 14, 2017).
Clark, et al., "A future for transgenic livestock," Nat. Rev. Genet., 4(10):825-833, (2003).
Dahlman, et al., "Orthogonal gene knockout and activation with a catalytically active Cas9 nuclease," Nat. Biotechnol., 33(11):1159-1161, (2015).
Dechiara, T.M., et al., "VelociMouse: Fully ES Cell-Derived FO-Generation Mice Obtained from the Injection of ES Cells into Eight-Cell-Stage Embryos," Jan. 1, 2009, Methods in Molecular Biology, 530(16): 311-324.
Dennis, "Welfare Issues of Genetically Modified Animals," ILAR J., 43(2):100-109, (2002).
Dominguez, et al., "Beyond editing: repurposing CRISPR-Cas9 for precision genome regulation and interrogation," Nat. Rev. Mol. Cell. Biol., 17(1):5-15, (2016).
Evers, et al., "CRISPR knockout screening outperforms shRNA and CRISPRi in identifying essential genes," Nature Biotechnology, 34(6):631-633 plus Online Methods, (Jun. 2016).
Finn, et al., "A Single Administration of CRISPR/Cas9 Lipid Nanoparticles Achieves Robust and Persistent In Vivo Genome Editing," Cell Reports, 22:1-9, (Feb. 27, 2018).
Frendewey, et al., "The Loss-of-Allele Assay for ES Cell Screening and Mouse Genotyping," Methods Enzymol., 476:295-307, (2010).
Friedrich, et al., "Promoter traps in embryonic stem cells: a genetic screen to identify and mutate developmental genes in mice," Genes Dev., 5(9):1513-1523, (1991).
Genoway, "Humanized Mouse Model," retrieved from https://www.genoway.com/services/customized-mouse/knockin-models/humanisation.htm on May 12, 2018.
Gertz, et al., "Diagnosis, Prognosis, and Therapy of Transthyretin Amyloidosis," J. Am. Coll. Cardiol., 66(21):2451-2466, (2015).
Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
Haapaniemi et al., "CRISPR-Cas9 genome editing induces a p53-mediated DNA damage response," Nat. Med. doi: 10.1038/s41591-018-0049-z, (Jun. 11, 2018, epub ahead of print).
Harari, et al., "Bridging the Species Divide: Transgenic Mice Humanized for Type-I Interferon Response," PLoS ONE, 9(1): e84259, (2014).
Herndler-Brandstetter, et al., "Humanized mouse model supports development, function, and tissue residency of human natural killer cells," Proc. Natl. Acad. Sci. U.S.A., 114(45):E9626-E9634, (2017).
Hopkins, et al., "Characterization of Autosomal Dominant Hypercholesterolemia Caused by PCSK9 Gain of Function Mutations and its Specific Treatment With Alirocumab, a PCSK9 Monoclonal Antibody," Circ. Cardiovasc. Genet., 8(6):823-831, (2015).
Houdebine, "Methods to Generate Transgenic Animals," pp. 31-48 in "Genetic Engineering in Livestock: New Applications and Interdisciplinary Perspectives," Ed. Engelhard et al., (2009).
Ihry et al., "p53 inhibits CRISPR-Cas9 engineering in human pluripotent stem cells," Nat. Med. doi: 10.1038/s41591-018-0050-6 (Jun. 11, 2018, epub ahead of print).
Jean, et al., "Pluripotent genes in avian stem cells," Dev. Growth Differ., 55(1): 41-51, (2013).
Jensen, "Design principles for nuclease-deficient CRISPR-based transcriptional regulators," FEMS Yeast Res., 18(4), doi:10.1093/femsyr/foy039, (2018).
Jia, et al., "Next-generation CRISPR/Cas9 transcriptional activation in *Drosophila* using flySAM," Pros. Natl. Acad. Sci. U.S.A., 115(18), 4719-4724, (Apr. 16, 2018).
Joung, et al., "Genome-scale CRISPR-Cas9 knockout and transcriptional activation screening," Nature Protocols, 12(4):828-863, (2017).
Kawamata, et al., "Generation of genetically modified rats from embryonic stem cells," Proc. Natl. Acad. Sci. U.S.A., 7(32):14223-14228, (2010).
Konermann, et al., "Genome-scale transcriptional activation by an engineered CRISPR-Cas9 complex," Nature, 517:583-588 plus Extended Data, (Jan. 29, 2017).
Kosicki et al., "Repair of double-strand breaks induced by CRISPR-Cas9 leads to large deletions and complex rearrangements," Nat. Biotechnol., 36(8): 765-771, (Jul. 16, 2018).
Kumar, et al., "Transgenic Mouse Technology: Principles and Methods," Methods Mol. Biol., 590:335-362, (2009).
La Russa, et al., "The New State of the Art: Cas9 for Gene Activation and Repression," Mol. Cell. Biol., 35(22):3800-3809, (2015).
Lau, et al., "Targeted Transgene Activation in the Brain Tissue by Systemic Delivery of Engineered AAV1 Expressing CRISPRa," Mol. Ther. Nucleic Acids, 16:637-649, (2019).
Lau, et al., "In vivo genome editing in animals using AAV-CRISPR system: applications to translational research of human disease," F1000Res, 6:2153, doi:10.12688/f1000research. 11243.1, (2017).
Liao, et al., "Amyloid Cardiomyopathy, Disease on the Rise," Circ. Res., 120(12):1865-1867, (2017).
Liao, et al., "In Vivo Target Gene Activation via CRISPR/Cas9-Mediated Trans-epigenetic Modulation," Cell, 171(7):1495-1507. e15 (2017).
Liu, et al., "Editing DNA Methylation in the Mammalian Genome," Cell, 167(1):233-247.e17 (2016).
Liu, et al., "Specific Expression of Interferon-gamma Induced by Synergistic Activation Mediator-Derived Systems Activates Innate Immunity and Inhibits Tumorigenesis," J. Microbiol. Biotechnol., 27(10):1855-1866, (2017).
Lundh, et al., "Bidirectional manipulation of gene expression in adipocytes using CRISPRa and siRNA," Mol. Metab., 6(10):1313-1320, (2017).
Lute, et al., "Human CTLA4 knock-in mice unravel the quantitative link between tumor immunity and autoimmunity induced by anti-CTLA-4 antibodies," Blood, 106(9):3127-3133, (2005).
Malina et al., "Repurposing CRISPR/Cas9 for in situ functional assays," Genes Dev., vol. 27(23):2602-2614, (2013).
Matharu, et al., "CRISPR-mediated activation of a promoter or enhancer rescues obesity caused by haploinsufficiency," Science, 363(6424), doi:10.1126/science.aau0629, (2019).
Morgens, et al., "Systematic comparison of CRISPR/Cas9 and RNAi screens for essential genes," Nature Biotechnology, 34(6):634-636 plus Online Methods, (Jun. 2016).
Mullins, et al., "Transgenesis in the rat and larger mammals," J. Clin. Invest. 97(7):1557-1560, (1996).
Munoz, et al., "Conventional pluripotency markers are unspecific forderived cell-lines," Theriogenology, 69(9): 1159-1164, (2008).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Nishimasu, et al., "Crystal Structure of Cas9 in Complex with Guide RNA and Target DNA," Cell, 156:935-949, (Feb. 27, 2014).
Paris, et al., "Equine embryos and embryonic stem cells: defining reliable markers of pluripotency," Theriogenology, 74(4): 516-524, (2010).
Platt, et al., "CRISPR-Cas9 Knockin Mice for Genome Editing and Cancer Modeling," Cell, 159:440-455, (Oct. 9, 2014).
Poueymirou, et al., "F0 generation mice fully derived from gene-targeted embryonic stem cells allowing immediate phenotypic analyses," Nat. Biotechnol., 25(1):91-99, (2007).

(56) References Cited

OTHER PUBLICATIONS

Ran et al., "In vivo genome editing using *Staphylococcus aureus*Cas9," Nature, 520(7546):186-191, (2015).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Senis, et al., "CRISPR/Cas9-mediated genome engineering: an adeno-associated viral (AAV) vector toolbox," Biotechnol. J., 9(11):1402-1412, (2014).
Shalem, et al., "Genome-Scale CRISPR-Cas9 Knockout Screening in Human Cells," Science, 343:84-87, (Jan. 3, 2014).
Shalem, et al., "High-throughput functional genomics using CRISPR-Cas9," Nature Reviews: Genetics, 16:299-311, (May 2015).
Shapiro, et al., "PCSK9: From Basic Science Discoveries to Clinical Trials," Circ. Res., 122(10):1420-1438, (2018).
Sigmund, "Viewpoint: Are Studies in Genetically Altered Mice out of Control?," Arterioscler. Thromb. Vasc. Biol., 20(6):1425-1429, (2000).
Ueda, et al., "Recent advances in transthyretin amyloidosis therapy,"3:19, doi: 10.1186/2047-9158-3-19, (2014).
Valenzuela, et al., "High-throughput engineering of the mouse genome coupled with high-resolution expression analysis," Nat. Biotechnol., 21(6):652-659, (2003).
Vora, et al., "Rational design of a compact CRISPR-Cas9 activator for AAV-mediated delivery," bioRxiv, doi: 10.1101/298620, (2018).
Wakchaure, et al., "Transgenic Animals: A Review on its Various Dimensions and Applications in Animal Biotechnology," International Journal of Emerging Technology and Advanced Engineering, 5(11):210-213, (2015).
Wang et al., "Mapping a functional cancer genome atlas of tumor suppressors in mouse liver using AAV-CRISPR-mediated direct in vivo screening," Sci. Adv. 4(2):eaao5508, (Feb. 28, 2018).
Wangensteen, al et., "Combinatorial genetics in liver repopulation and carcinogenesis with a in vivo CRISPR activation platform," Hepatology, 68(2):663-676, (2018).
Xu, et al., "CRISPR-ON-Mediated KLF4 overexpression inhibits the proliferation, migration and invasion of urothelial bladder cancer in vitro and in vivo," Oncotarget, 8(60):102078-102087, (2017).
Yin, et al., "Delivery technologies for genome editing," Nat. Rev. Drug Discov., 16(6):387-399, (2017).
Zambrowicz, et al., "Disruption of overlapping transcripts in the ROSA beta geo 26 gene trap strain leads to widespread expression of beta-galactosidase in mouse embryos and hematopoietic cells," Proc. Natl. Acad. Sci. U.S.A., 94(8):3789-3794, (1997).
Zhang Lab—CRISPR Mouse Activation Pooled Library (SAM v1) [Retrieved from the Internet Oct. 19, 2017 <https://www.addgene.org/pooled-library/zhang-mouse-sam-v1/>].
Zhang, et al., "CRISPR/gRNA-directed synergistic activation mediator (SAM) induces specific, persistent and robust reactivation of the HIV-1 latent reservoirs," Scientific Reports, 5:16277, (Nov. 5, 2015).
Zhao, et al., "Inconsistency between hepatic expression and serum concentration of transthyretin in mice humanized at the transthyretin locus," Genes to Cells, 13:1257-1268, (2008).
Zhou, et al., "Developing tTA transgenic rats for inducible and reversible gene expression," Int. J. Biol. Sci., 5(2):171-181, (2009).
Zhou, et al., "In vivo simultaneous transcriptional activation of multiple genes in the brain using CRISPR-dCas9-activator transgenic mice," Nat. Neurosci., 21(3):440-446, (Jan. 15, 2018).
U.S. Appl. No. 16/358,395, Final Office Action mailed May 2, 2022.
U.S. Appl. No. 16/358,395, Non-Final Office Action mailed Oct. 22, 2021.
U.S. Appl. No. 16/358,395, Notice of Allowance and Interview Summary mailed Aug. 2, 2022.
U.S. Appl. No. 16/358,395, Requirement for Restriction/Election mailed Jun. 11, 2021.
WIPO Application No. PCT/US2019/023009, PCT International Search Report and Written Opinion of the International Searching Authority mailed May 21, 2019.

TRANSCRIPTION MODULATION IN ANIMALS USING CRISPR/CAS SYSTEMS

CROSS-REFERENCE TO RELATED APPLICATIONS

This application is a divisional application of U.S. application Ser. No. 16/358,395, filed Mar. 19, 2019, which claims the benefit of U.S. Application No. 62/644,961, filed Mar. 19, 2018, each of which is herein incorporated by reference in its entirety for all purposes.

REFERENCE TO A SEQUENCE LISTING SUBMITTED AS A TEXT FILE VIA EFS WEB

The Sequence Listing written in file 585180SEQLIST.txt is 213 kilobytes, was created on Nov. 1, 2022, and is hereby incorporated by reference.

BACKGROUND

Gene expression in strictly controlled in many biological processes, such as development and diseases. Transcription factors regulate gene expression by binding to specific DNA sequences at the enhancer and promoter regions of target genes, and modulate transcription through their effector domains. Based on the same principle, artificial transcription factors (ATFs) have been generated by fusing various functional domains to a DNA binding domain engineered to bind to genes of interest, thereby modulating their expression. However, binding specificity of these ATFs is usually degenerate, can be difficult to predict, and the complex and time-consuming design and generation limits there applications.

CRISPR/Cas technology is a promising new therapeutic modality and can be used not only to make targeted genomic modifications but to regulate transcription of target genes. However, there is a need for better means of assessing the efficiency of introduced CRISPR/Cas agents in vivo. One limitation of testing the system in vivo is the need to simultaneously introduce all components into a living organism. The typical method of introducing these components is to transiently transfect DNA constructs into cells that will generate the appropriate RNAs and protein. Though effective, this approach has an inherent disadvantage as the cells must rely on the plasmid DNA constructs to first undergo transcription and then translation before the Cas protein is available to interact with the sgRNA component. Better methods and tools are needed to more effectively assess the activity of introduced CRISPR/Cas agents and to assess different delivery methods and parameters for targeting specific tissues or cell types in vivo.

In addition, the delivery of biologically active agents such as CRISPR/Cas agents to subjects is often hindered by difficulties in the components reaching the target cell or tissue. These restrictions can result, for example, in the need to use much higher concentrations of the agents than is desirable to achieve a result, which increases the risk of toxic effects and side effects. Improved delivery methods and methods of assessing such delivery methods in vivo are needed.

SUMMARY

Non-human animals comprising a CRISPR/Cas synergistic activation mediator (SAM) systems are provided, as well as methods of using such non-human animals (e.g., SAM-ready non-human animals) for assessing the ability of CRISPR/Cas SAM agents to activate transcription of a target gene in vivo or to assess the effects of activating transcription or increasing expression of a target gene in vivo. Non-human animal genomes or cells comprising a CRISPR/Cas synergistic activation mediator (SAM) systems are also provided.

In one aspect, provided are non-human animal genomes, non-human animal cells, or non-human animals comprising one or more genomically integrated synergistic activation mediator expression cassettes. Such non-human animal genomes, non-human animal cells, or non-human animals can comprise, for example, a first genomically integrated expression cassette, wherein the first expression cassette comprises: (a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor fused to one or more transcriptional activation domains.

Such non-human animal genomes, non-human animal cells, or non-human animals can further comprise one or more guide RNAs or an expression cassette that encodes the one or more guide RNAs, each guide RNA comprising one or more adaptor-binding elements to which the chimeric adaptor protein can specifically bind, wherein each of the one or more guide RNAs is capable of forming a complex with the Cas protein and guiding it to a target sequence within a target gene. Optionally, the expression cassette encoding the one or more guide RNAs is in an adeno-associated virus (AAV), such as AAV8. Optionally, the expression cassette encoding the one or more guide RNAs is in an AAV, each of the one or more guide RNAs is operably linked to a different U6 promoter, and the one or more guide RNAs comprise multiple guide RNAs that target a single gene.

Such non-human animal genomes, non-human animal cells, or non-human animals can further comprise a second genomically integrated expression cassette that encodes one or more guide RNAs each comprising one or more adaptor-binding elements to which the chimeric adaptor protein can specifically bind, wherein each of the one or more guide RNAs is capable of forming a complex with the Cas protein and guiding it to a target sequence within a target gene.

In some non-human animal genomes, non-human animal cells, or non-human animals, the target sequence comprises a regulatory sequence within the target gene. Optionally, the regulatory sequence comprises a promoter or an enhancer. In some non-human animal genomes, non-human animal cells, or non-human animals, the target sequence is within 200 base pairs of the transcription start site of the target gene. Optionally, the target sequence is within the region 200 base pairs upstream of the transcription start site and 1 base pair downstream of the transcription start site.

In some non-human animal genomes, non-human animal cells, or non-human animals, the sequence encoding each of the one or more guide RNAs is operably linked to a different promoter such as a U6 promoter. In some non-human animal genomes, non-human animal cells, or non-human animals, each of the one or guide RNAs comprises two adaptor-binding elements to which the chimeric adaptor protein can specifically bind. Optionally, a first adaptor-binding element is within a first loop of each of the one or more guide RNAs, and a second adaptor-binding element is within a second loop of each of the one or more guide RNAs. Optionally, each of one or more guide RNAs is a single guide RNA comprising a CRISPR RNA (crRNA) portion fused to a transactivating CRISPR RNA (tracrRNA) portion, wherein the first loop is the tetraloop corresponding to residues 13-16 of SEQ ID NO: 12, and the second loop is the stem loop 2 corresponding to residues 53-56 of SEQ ID NO: 12. In some non-human animal genomes, non-human animal cells, or non-human animals, the adaptor-binding element comprises the sequence set forth in SEQ ID NO: 16. Optionally, each of the one or more guide RNAs comprises the sequence set forth in SEQ ID NO: 40 or 63.

In some non-human animal genomes, non-human animal cells, or non-human animals, at least one of the one or more guide RNAs targets a disease-associated gene. Optionally, at least one of the one or more guide RNAs targets a Ttr gene, optionally wherein the Ttr-targeting guide RNA targets a sequence comprising the sequence set forth in any one of SEQ ID NOS: 34-36 or optionally wherein the Ttr-targeting guide RNA comprises the sequence set forth in any one of SEQ ID NOS: 37-39. Optionally, at least one of the one or more guide RNAs targets a Pcsk9 gene, optionally wherein the Pcsk9-targeting guide RNA targets a sequence comprising the sequence set forth in any one of SEQ ID NOS: 89-91 or optionally wherein the Pcsk9-targeting guide RNA comprises the sequence set forth in any one of SEQ ID NOS: 92-94. Optionally, at least one of the one or more guide RNAs targets a Ldlr gene, optionally wherein the Ldlr-targeting guide RNA targets a sequence comprising the sequence set forth in any one of SEQ ID NOS: 75-77 or optionally wherein the Ldlr-targeting guide RNA comprises the sequence set forth in any one of SEQ ID NOS: 78-80.

In some non-human animal genomes, non-human animal cells, or non-human animals, the one or more guide RNAs target two or more target genes. In some non-human animal genomes, non-human animal cells, or non-human animals, the one or more guide RNAs comprise multiple guide RNAs that target a single target gene. In some non-human animal genomes, non-human animal cells, or non-human animals, the one or more guide RNAs comprise at least three guide RNAs that target a single target gene. Optionally, the at least three guide RNAs target the mouse Ttr locus, wherein a first guide RNA targets a sequence comprising SEQ ID NO: 34 or comprises the sequence set forth in SEQ ID NO: 37, a second guide RNA targets a sequence comprising SEQ ID NO: 35 or comprises the sequence set forth in SEQ ID NO: 38, and a third guide RNA targets a sequence comprising SEQ ID NO: 36 or comprises the sequence set forth in SEQ ID NO: 39. Optionally, the at least three guide RNAs target the mouse Pcsk9 locus, wherein a first guide RNA targets a sequence comprising SEQ ID NO: 89 or comprises the sequence set forth in SEQ ID NO: 92, a second guide RNA targets a sequence comprising SEQ ID NO: 90 or comprises the sequence set forth in SEQ ID NO: 93, and a third guide RNA targets a sequence comprising SEQ ID NO: 91 or comprises the sequence set forth in SEQ ID NO: 94. Optionally, the at least three guide RNAs target the mouse Ldlr locus, wherein a first guide RNA targets a sequence comprising SEQ ID NO: 75 or comprises the sequence set forth in SEQ ID NO: 78, a second guide RNA targets a sequence comprising SEQ ID NO: 76 or comprises the sequence set forth in SEQ ID NO: 79, and a third guide RNA targets a sequence comprising SEQ ID NO: 77 or comprises the sequence set forth in SEQ ID NO: 80.

In some non-human animal genomes, non-human animal cells, or non-human animals, the Cas protein is a Cas9 protein. Optionally, the Cas9 protein is a *Streptococcus pyogenes* Cas9 protein. Optionally, the Cas9 protein comprises mutations corresponding to D10A and N863A when optimally aligned with a *Streptococcus pyogenes* Cas9 protein. Optionally, the sequence encoding the Cas protein is codon-optimized for expression in the non-human animal.

In some non-human animal genomes, non-human animal cells, or non-human animals, the one or more transcriptional activator domains in the chimeric Cas protein are selected from: VP16, VP64, p65, MyoD1, HSF1, RTA, SET7/9, and a combination thereof. Optionally, the one or more transcriptional activator domains in the chimeric Cas protein comprise VP64.

In some non-human animal genomes, non-human animal cells, or non-human animals, the chimeric Cas protein comprises from N-terminus to C-terminus: the catalytically inactive Cas protein; and the VP64 transcriptional activator domain. In some non-human animal genomes, non-human animal cells, or non-human animals, the chimeric Cas protein comprises from N-terminus to C-terminus: the catalytically inactive Cas protein; a nuclear localization signal; and the VP64 transcriptional activator domain. Optionally, the chimeric Cas protein comprises a sequence at least 90%, 95%, 96%, 97%, 98%, 99%, or 100% identical to the sequence set forth in SEQ ID NO: 1. Optionally, the segment of the first expression cassette encoding the chimeric Cas protein comprises a sequence at least 90%, 95%, 96%, 97%, 98%, 99%, or 100% identical to the sequence set forth in SEQ ID NO: 25.

In some non-human animal genomes, non-human animal cells, or non-human animals, the first expression cassette further comprises a polyadenylation signal or transcription terminator upstream of the segment encoding the chimeric Cas protein, wherein the polyadenylation signal or transcription terminator is flanked by recombinase recognition sites, wherein the polyadenylation signal or transcription terminator has been excised in a tissue-specific manner. Optionally, the polyadenylation signal or transcription terminator has been excised in the liver. Optionally, the recombinase is a Cre recombinase. Optionally, the non-human animal genome, non-human animal cell, or non-human animal further comprises a genomically integrated recombinase expression cassette comprising a recombinase coding sequence operably linked to a tissue-specific promoter. Optionally, the recombinase gene is operably linked to one of the promoters set forth in Table 2.

In some non-human animal genomes, non-human animal cells, or non-human animals, the adaptor is at the N-terminal end of the chimeric adaptor protein, and the one or more transcriptional activation domains are at the C-terminal end of the chimeric adaptor protein. Optionally, the adaptor comprises an MS2 coat protein or a functional fragment or variant thereof. Optionally, the one or more transcriptional activation domains in the chimeric adaptor protein are selected from: VP16, VP64, p65, MyoD1, HSF1, RTA, SET7/9, and a combination thereof. Optionally, the one or more transcriptional activation domains in the chimeric adaptor protein comprise p65 and HSF1.

In some non-human animal genomes, non-human animal cells, or non-human animals, the chimeric adaptor protein comprises from N-terminus to C-terminus: an MS2 coat protein; a nuclear localization signal; the p65 transcriptional activation domain; and the HSF1 transcriptional activation domain. Optionally, the chimeric adaptor protein comprises a sequence at least 90%, 95%, 96%, 97%, 98%, 99%, or 100% identical to the sequence set forth in SEQ ID NO: 6. Optionally, the segment of the first expression cassette encoding the chimeric adaptor protein comprises a sequence at least 90%, 95%, 96%, 97%, 98%, 99%, or 100% identical to the sequence set forth in SEQ ID NO: 27.

In some non-human animal genomes, non-human animal cells, or non-human animals, the first expression cassette is multicistronic. Optionally, the segment of the first expression cassette encoding the chimeric Cas protein is separated from the segment of the first expression cassette encoding the chimeric adaptor protein by an internal ribosome entry site (IRES). Optionally, the segment of the first expression cassette encoding the chimeric Cas protein is separated from the segment of the first expression cassette encoding the chimeric adaptor protein by a nucleic acid encoding a 2A peptide. Optionally, the 2A peptide is a T2A peptide.

In some non-human animal genomes, non-human animal cells, or non-human animals, the first expression cassette is integrated into a safe harbor locus. In some non-human animal genomes, non-human animal cells, or non-human animals, the first expression cassette and/or the second expression cassette is integrated into a safe harbor locus. Optionally, the non-human animal genome, non-human animal cell, or non-human animal is heterozygous for the first expression cassette and is heterozygous for the second expression cassette, and the first expression cassette is genomically integrated within a first allele of the safe harbor locus, and the second expression cassette is genomically integrated within a second allele of the safe harbor locus. Optionally, the safe harbor locus is a Rosa26 locus. Optionally, the first expression cassette is operably linked to an endogenous promoter in the safe harbor locus.

Some such non-human animals are mammals. Optionally, the mammal is a rodent. Optionally, the rodent is a rat or a mouse. Optionally, the rodent is a mouse.

In another aspect, provided are targeting vectors for making any of the non-human animal genomes, non-human animal cells, and non-human animals disclosed above. Such targeting vectors can comprise an insert nucleic acid flanked by a 5' homology arm targeting a 5' target sequence at a target genomic locus and a 3' homology arm targeting a 3' targeting sequence at the target genomic locus, wherein the insert nucleic acid comprises an expression cassette, wherein the expression cassette comprises (a) a nucleic acid encoding a chimeric Clustered Regularly Interspaced Short Palindromic Repeats (CRISPR) associated (Cas) protein comprising a nuclease-inactive Cas protein fused to one or more transcriptional activation domains; and (b) a nucleic acid encoding a chimeric adaptor protein comprising an adaptor fused to one or more transcriptional activation domains.

In another aspect, provided are methods of making any of the non-human animals disclosed above. Some such methods comprise: (a) introducing into a non-human animal embryonic stem (ES) cell: (i) a nuclease agent that targets a target sequence in a target genomic locus; and (ii) a targeting vector comprising a nucleic acid insert comprising the first expression cassette flanked by a 5' homology arm corresponding to a 5' target sequence in the target genomic locus and a 3' homology arm corresponding to a 3' target sequence in the target genomic locus, wherein the targeting vector recombines with the target genomic locus to produce a genetically modified non-human ES cell comprising in its genome the first expression cassette at the target genomic locus; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the first expression cassette at the target genomic locus. Optionally, the targeting vector is a large targeting vector at least 10 kb in length or in which the sum total of the 5' and 3' homology arms is at least 10 kb in length.

Some such methods comprise: (a) introducing into a non-human animal one-cell stage embryo: (i) a nuclease agent that targets a target sequence in a target genomic locus; and (ii) a targeting vector comprising a nucleic acid insert comprising the first expression cassette flanked by a 5' homology arm corresponding to a 5' target sequence in the target genomic locus and a 3' homology arm corresponding to a 3' target sequence in the target genomic locus, wherein the targeting vector recombines with the target genomic locus to produce a genetically modified non-human ES cell comprising in its genome the first expression cassette at the target genomic locus; (b) gestating the genetically modified non-human animal one-cell stage embryo in a surrogate mother to produce a genetically modified F0 generation non-human animal comprising in its genome the first expression cassette at the target genomic locus.

In some such methods, the nuclease agent comprises a Cas protein and a guide RNA. Optionally, the Cas protein is a Cas9 protein. Optionally, such methods can comprise introducing a second guide RNA that targets a second target sequence within the target genomic locus.

In some such methods, the non-human animal is a mouse or a rat. Optionally, the non-human animal is a mouse.

In another aspect, provided are methods of increasing expression of a target gene in vivo in any of the non-human animals. Such methods can comprise, for example, introducing into the non-human animal one or more guide RNAs each comprising one or more adaptor-binding elements to which the chimeric adaptor protein can specifically bind, wherein the one or more guide RNAs form complexes with the chimeric Cas protein and chimeric adaptor protein and guide them to a target sequence within the target gene, thereby increasing expression of the target gene. Optionally, the target gene is a gene expressed in the liver.

In some such methods, the one or more guide RNAs are introduced via adeno-associated virus (AAV)-mediated delivery. Optionally, the AAV is AAV8. In some such methods, the one or more guide RNAs are introduced via lipid-nanoparticle-mediated delivery or hydrodynamic delivery. In some such methods, the route of administration of the one or more guide RNAs to the non-human animal is intravenous injection, intraparenchymal injection, intraperitoneal injection, nasal installation, or intravitreal injection.

In some such methods, the target sequence comprises a regulatory sequence within the target gene. Optionally, the regulatory sequence comprises a promoter or an enhancer. In some such methods, the target sequence is within 200 base pairs of the transcription start site of the target gene. Optionally, the target sequence is within the region 200 base pairs upstream of the transcription start site and 1 base pair downstream of the transcription start site.

In some such methods, the one or more guide RNAs are introduced in the form of RNA. In some such methods, the one or more guide RNAs are introduced in the form of DNA. Optionally, each of the one or more guide RNAs is operably linked to a different promoter such as a U6 promoter.

In some such methods, each of the one or guide RNAs comprises two adaptor-binding elements to which the chimeric adaptor protein can specifically bind. Optionally, a first adaptor-binding element is within a first loop of each of the one or more guide RNAs, and a second adaptor-binding element is within a second loop of each of the one or more guide RNAs. Optionally, each of one or more guide RNAs is a single guide RNA comprising a CRISPR RNA (crRNA) portion fused to a transactivating CRISPR RNA (tracrRNA)

portion, wherein the first loop is the tetraloop corresponding to residues 13-16 of SEQ ID NO: 12 and the second loop is the stem loop 2 corresponding to residues 53-56 of SEQ ID NO: 12.

In some such methods, the adaptor-binding element comprises the sequence set forth in SEQ ID NO: 16. Optionally, each of the one or more guide RNAs comprises the sequence set forth in SEQ ID NO: 40 or 63.

In some such methods, at least one of the one or more guide RNAs targets a disease-associated gene. Optionally, the disease-associated gene is a Ttr gene, optionally wherein the Ttr-targeting guide RNA targets a sequence comprising the sequence set forth in any one of SEQ ID NOS: 34-36 or optionally wherein the Ttr-targeting guide RNA comprises the sequence set forth in any one of SEQ ID NOS: 37-39. In some such methods, at least one of the one or more guide RNAs targets a Pcsk9 gene, optionally wherein the Pcsk9-targeting guide RNA targets a sequence comprising the sequence set forth in any one of SEQ ID NOS: 89-91 or optionally wherein the Pcsk9-targeting guide RNA comprises the sequence set forth in any one of SEQ ID NOS: 92-94. Optionally, the method causes hypercholesterolemia in the non-human animal. In some such methods, wherein at least one of the one or more guide RNAs targets a Ldlr gene, optionally wherein the Ldlr-targeting guide RNA targets a sequence comprising the sequence set forth in any one of SEQ ID NOS: 75-77 or optionally wherein the Ldlr-targeting guide RNA comprises the sequence set forth in any one of SEQ ID NOS: 78-80.

In some such methods, the one or more guide RNAs target two or more target genes. In some such methods, the one or more guide RNAs comprise multiple guide RNAs that target a single target gene. In some such methods, the one or more guide RNAs comprise at least three guide RNAs that target a single target gene. Optionally, the at least three guide RNAs target the mouse Ttr locus, wherein a first guide RNA targets a sequence comprising SEQ ID NO: 34 or comprises the sequence set forth in SEQ ID NO: 37, a second guide RNA targets a sequence comprising SEQ ID NO: 35 or comprises the sequence set forth in SEQ ID NO: 38, and a third guide RNA targets a sequence comprising SEQ ID NO: 36 or comprises the sequence set forth in SEQ ID NO: 39. Optionally, the at least three guide RNAs target the mouse Pcsk9 locus, wherein a first guide RNA targets a sequence comprising SEQ ID NO: 89 or comprises the sequence set forth in SEQ ID NO: 92, a second guide RNA targets a sequence comprising SEQ ID NO: 90 or comprises the sequence set forth in SEQ ID NO: 93, and a third guide RNA targets a sequence comprising SEQ ID NO: 91 or comprises the sequence set forth in SEQ ID NO: 94. Optionally, the at least three guide RNAs target the mouse Ldlr locus, wherein a first guide RNA targets a sequence comprising SEQ ID NO: 75 or comprises the sequence set forth in SEQ ID NO: 78, a second guide RNA targets a sequence comprising SEQ ID NO: 76 or comprises the sequence set forth in SEQ ID NO: 79, and a third guide RNA targets a sequence comprising SEQ ID NO: 77 or comprises the sequence set forth in SEQ ID NO: 80.

In some such methods, the increase in expression of the target gene is at least 0.5-fold, 1-fold, 2-fold, 3-fold, 4-fold, 5-fold, 6-fold, 7-fold, 8-fold, 9-fold, 10-fold, or 20-fold higher relative to a control non-human animal.

In some such methods, the first expression cassette further comprises a polyadenylation signal or transcription terminator upstream of the segment encoding the chimeric Cas protein, wherein the polyadenylation signal or transcription terminator is flanked by recombinase recognition sites recognized by a site-specific recombinase, and wherein the method further comprises introducing the recombinase into the non-human animal. Optionally, the recombinase is a Cre recombinase. Optionally, the recombinase is introduced via adeno-associated virus (AAV)-mediated delivery. Optionally, the AAV is AAV8. Optionally, the recombinase is introduced via lipid-nanoparticle-mediated delivery or hydrodynamic delivery. Optionally, the recombinase is introduced or expressed in a tissue-specific manner. Optionally, the recombinase is introduced in the form of protein. Optionally, the recombinase is introduced in the form of DNA or RNA. Optionally, the recombinase is introduced in the form of DNA operably linked to one of the promoters set forth in Table 2. Optionally, the route of administration of the recombinase to the non-human animal is intravenous injection, intraparenchymal injection, intraperitoneal injection, nasal installation, or intravitreal injection.

In some such methods, the one or more guide RNAs are introduced via adeno-associated virus (AAV)-mediated delivery, each of the one or more guide RNAs is operably linked to a different U6 promoter, and the one or more guide RNAs comprise multiple guide RNAs that target a single gene.

In another aspect, provided is a method for modeling hypercholesterolemia in any of the non-human animals described above. Such methods can comprise introducing into the non-human animal one or more guide RNAs targeting Pcsk9, wherein each of the one or more guide RNAs comprise one or more adaptor-binding elements to which the chimeric adaptor protein can specifically bind, wherein the one or more guide RNAs form complexes with the chimeric Cas protein and chimeric adaptor protein and guide them to a target sequence within Pcsk9, thereby increasing expression of Pcsk9 and causing hypercholesterolemia.

DEFINITIONS

Figure 1A:
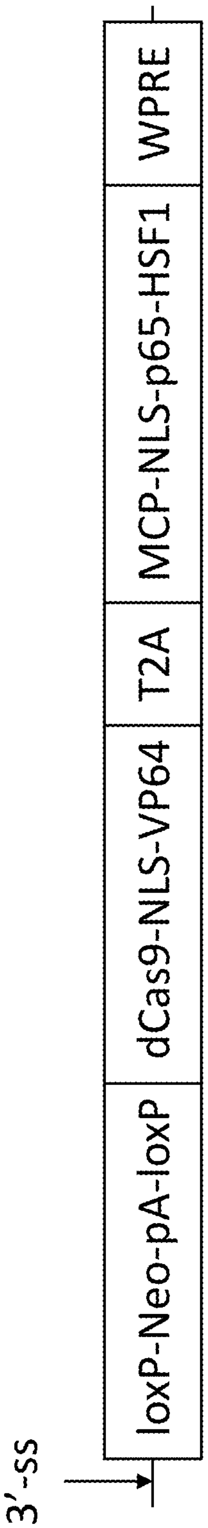
FIG. 1A (not to scale) shows a lox-stop-lox (LSL) dCas9 Synergistic Activation Mediator (SAM) allele, comprising from 5' to 3': a 3' splicing sequence; a first loxP site; a neomycin resistance gene; a polyadenylation signal; a second loxP site; a dCas9-NLS-VP64 coding sequence; a T2A peptide coding sequence; an MCP-NLS-p65-HSF1 coding sequence; and a Woodchuck hepatitis virus posttranscriptional regulatory element (WPRE).

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "expression vector" or "expression construct" or "expression cassette" refers to a recombinant nucleic acid containing a desired coding sequence operably linked to appropriate nucleic acid sequences necessary for the expression of the operably linked coding sequence in a particular host cell or organism. Nucleic acid sequences necessary for expression in prokaryotes usually include a promoter, an operator (optional), and a ribosome binding site, as well as other sequences. Eukaryotic cells are generally known to utilize promoters, enhancers, and termination and polyadenylation signals, although some elements may be deleted and other elements added without sacrificing the necessary expression.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "isolated" with respect to proteins, nucleic acids, and cells includes proteins, nucleic acids, and cells that are relatively purified with respect to other cellular or organism components that may normally be present in situ, up to and including a substantially pure preparation of the protein, nucleic acid, or cell. The term "isolated" also includes proteins and nucleic acids that have no naturally occurring counterpart or proteins or nucleic acids that have been chemically synthesized and are thus substantially uncontaminated by other proteins or nucleic acids. The term "isolated" also includes proteins, nucleic acids, or cells that have been separated or purified from most other cellular components or organism components with which they are naturally accompanied (e.g., other cellular proteins, nucleic acids, or cellular or extracellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous Rosa26 sequence of a non-human animal refers to a native Rosa26 sequence that naturally occurs at the Rosa26 locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "Ttr locus" may refer to the specific location of a Ttr gene, Ttr DNA sequence, TTR-encoding sequence, or Ttr position on a chromosome of the genome of an organism that has been identified as to where such a sequence resides. A "Ttr locus" may comprise a regulatory element of a Ttr gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

A constitutive promoter is one that is active in all tissues or particular tissues at all developing stages. Examples of constitutive promoters include the human cytomegalovirus immediate early (hCMV), mouse cytomegalovirus immediate early (mCMV), human elongation factor 1 alpha (hEF1$\alpha$), mouse elongation factor 1 alpha (mEF1$\alpha$), mouse phosphoglycerate kinase (PGK), chicken beta actin hybrid (CAG or CBh), SV40 early, and beta 2 tubulin promoters.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original, but with retention of the basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| | | | | | |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to an endogenous or heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p \leq 0.05$.

DETAILED DESCRIPTION

I. Overview

The Clustered Regularly Interspersed Short Palindromic Repeats (CRISPR)/CRISPR-associated (Cas) (CRISPR/Cas) system is a powerful tool for genome engineering and for regulating expression of target genes. One limitation of the system in vivo is the need to simultaneously introduce all components into a living organism. Typically, these components are introduced transiently by transfecting DNA constructs into cells that will generate the appropriate RNAs and protein. Though effective, this approach has an inherent disadvantage as the cells must rely on the plasmid DNA constructs to first undergo transcription and then translation before the Cas protein is available to interact with the sgRNA component. Better methods and tools are needed to more effectively assess the activity of CRISPR/Cas agents and to assess different delivery methods and parameters for targeting specific tissues or cell types in vivo.

In an exemplary CRISPR/Cas synergistic activation mediator (SAM) system, several activation domains interact to cause a greater transcriptional activation than could be induced by any one factor alone. To use the SAM system, typically three viruses need to be introduced. The first virus contains catalytically inactive Cas protein directly fused to a VP64 domain, a transcriptional activator composed of four tandem copies of Herpes Simplex Viral Protein 16. When VP64 is fused to a protein that binds near a transcriptional start site, it acts as a strong transcriptional activator. The second virus brings in MS2 coat protein (MCP) fused to two additional activating transcription factors: heat-shock factor 1 (HSF1); and transcription factor 65 (p65). The MCP naturally binds to MS2 stem loops. In an exemplary SAM system, MCP interacts MS2 stem loops engineered into the CRISPR-associated sgRNA and thereby shuttles the bound transcription factors to the appropriate genomic location. The third virus introduces the MS2-loop-containing sgRNA.

Methods and compositions are provided herein for activating transcription of target genes in vivo and ex vivo and for assessing CRISPR/Cas-mediated transcriptional activation activity in vivo and ex vivo. The methods and compositions employ cells and non-human animals comprising chimeric Cas protein expression cassettes, chimeric adaptor protein expression cassettes, or synergistic activation mediator (SAM) expression cassettes (e.g., a chimeric Cas protein coding sequence and a chimeric adaptor protein sequence) so that the components can be constitutively available or, for example, available in a tissue-specific or temporal-specific manner. The cassettes can be genomically integrated. Such cells and non-human animals can also comprise guide RNA expression cassettes and/or recombinase expression cassettes as disclosed elsewhere herein. Alternatively, one or more components (e.g., guide RNAs and/or recombinases)

can be introduced into the cells and non-human animals by other means to induce transcriptional activation of a target gene.

Non-human animals comprising the SAM expression cassettes simplify the process for testing delivery and activity of CRISPR/Cas components in vivo because only the guide RNAs need to be introduced into the non-human animal to activate transcription of a target gene. If the non-human animal also comprises a guide RNA expression cassette, the effects of target gene activation can be studied without introducing any further components. In addition, the SAM expression cassettes or guide RNA expression cassettes can optionally be conditional expression cassettes that can be selectively expressed in particular tissues or developmental stages, which can, for example, reduce the risk of Cas-mediated toxicity in vivo. Alternatively, such expression cassettes can be constitutively expressed to enable testing of activity in any and all types of cells, tissues, and organs.

Methods and compositions are also provided for making and using these non-human animals to test and measure the ability of a Cas-based SAM system to activate transcription of a target gene in vivo or to assess the effects of increasing transcription of a target gene in vivo.

II. Non-Human Animals Comprising Synergistic Activation Mediator (SAM) Expression Cassettes The non-human animal genomes, non-human animal cells, and non-human animals disclosed herein comprise Clustered Regularly Interspersed Short Palindromic Repeats (CRISPR)/CRISPR-associated (Cas)-based synergistic activation mediator (SAM) expression cassettes for use in methods of activating transcription of target genes in vivo or ex vivo and to assess the ability of SAM systems or components of such systems (e.g., guide RNAs introduced into the non-human animal or cell) to activate transcription of a target genomic locus in vivo or ex vivo. The methods and compositions disclosed herein utilize non-human animals or cells comprising Clustered Regularly Interspersed Short Palindromic Repeats (CRISPR)/CRISPR-associated (Cas)-based synergistic activation mediator (SAM) expression cassettes for use in methods of activating transcription of target genes in vivo or ex vivo and to assess the ability of SAM systems or components of such systems (e.g., guide RNAs introduced into the non-human animal or cell) to activate transcription of a target genomic locus in vivo or ex vivo. The SAM systems described herein comprise chimeric Cas proteins and chimeric adaptor proteins and can be used with guide RNAs as described elsewhere herein to activate transcription of target genes. The guide RNAs can be encoded by genomically integrated expression cassettes, or they can be provided by AAV or any other suitable means. Chimeric Cas proteins and chimeric adaptor proteins (e.g., comprising an adaptor that specifically binds to an adaptor-binding element within a guide RNA; and one or more heterologous transcriptional activation domains) are described in further detail elsewhere herein.

CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

The methods and compositions disclosed herein employ the CRISPR/Cas systems by using or testing the ability of CRISPR complexes (comprising a guide RNA (gRNA) complexed with a chimeric Cas protein and a chimeric adaptor protein) to induce transcriptional activation of a target genomic locus in vivo.

The genomes, cells, and non-human animals disclosed herein comprise a chimeric Cas protein expression cassette and/or a chimeric adaptor protein expression cassette. For example, the genomes, cells, and non-human animals disclosed herein can comprise a synergistic activation mediator (SAM) expression cassette comprising a chimeric Cas protein coding sequence and a chimeric adaptor protein coding sequence.

Such genomes, cells, or non-human animals comprising a SAM expression cassette have the advantage of needing delivery only of guide RNAs in order to induce transcriptional activation of a target genomic locus. Some such genomes, cells, or non-human animals also comprise a guide RNA expression cassette so that all components required for transcriptional activation of a target gene are already present. The SAM systems can be used in such cells to provide increased expression of target genes in any desired manner. For example, expression of one or more target genes can be increased in a constitutive manner or in a regulated manner (e.g., inducible, tissue-specific, temporally regulated, and so forth).

A. Chimeric Cas Proteins

Provided are chimeric Cas proteins that can bind to the guide RNAs disclosed elsewhere herein to activate transcription of target genes. Such chimeric Cas proteins can comprise: (a) a DNA-binding domain that is a Clustered Regularly Interspaced Short Palindromic Repeats (CRISPR)-associated (Cas) protein or a functional fragment or variant thereof that is capable of forming a complex with a guide RNA and binding to a target sequence; and (b) one or more transcriptional activation domains or functional fragments or variants thereof. For example, such fusion proteins can comprise 1, 2, 3, 4, 5, or more transcriptional activation domains (e.g., two or more heterologous transcriptional activation domains or three or more heterologous transcriptional activation domains). In one example, the chimeric Cas protein can comprise a catalytically inactive Cas protein (e.g., dCas9) and a VP64 transcriptional activation domain or a functional fragment or variant thereof. For example, such a chimeric Cas protein can comprise, consist essentially of, or consist of an amino acid sequence at least 85%, 90%, 91%, 92%, 93%, 94%, 95%, 96%, 97%, 98%, 99%, or 100% identical to the dCas9-VP64 chimeric Cas protein sequence set forth in SEQ ID NO: 1. However, chimeric Cas proteins in which the transcriptional activation domains comprise other transcriptional activation domains or functional fragments or variants thereof and/or in which the Cas protein comprises other Cas proteins (e.g., catalytically inactive Cas proteins) are also provided. Examples of other suitable transcriptional activation domains are provided elsewhere herein.

The transcriptional activation domain(s) can be located at the N-terminus, the C-terminus, or anywhere within the Cas protein. For example, the transcriptional activation domain(s) can be attached to the Rec domain, the Rec2 domain, the HNH domain, or the PI domain of a *Streptococcus pyogenes* Cas9 protein or any corresponding region of an orthologous Cas9 protein or homologous or orthologous Cas protein when optimally aligned with the *S. pyogenes* Cas9 protein. For example, the transcriptional activation domain can be attached to the Rec domain at position 553, the Rec domain at position 575, the Rec2 domain at any position within positions 175-306 or replacing part of or the entire region within positions 175-306, the HNH domain at any position within positions 715-901 or replacing part of or the entire region within positions 715-901, or the PI domain at position 1153 of the *S. pyogenes* Cas9 protein. See, e.g., WO 2016/049258, herein incorporated by reference in its entirety for all purposes. The transcriptional activation domain may be flanked by one or more linkers on one or both sides as described elsewhere herein.

Chimeric Cas proteins can also be operably linked or fused to additional heterologous polypeptides. The fused or linked heterologous polypeptide can be located at the N-terminus, the C-terminus, or anywhere internally within the chimeric Cas protein. For example, a chimeric Cas protein can further comprise a nuclear localization signal. Examples of suitable nuclear localization signals and other modifications to Cas proteins are described in further detail elsewhere herein.

(1) Cas Proteins

Cas proteins generally comprise at least one RNA recognition or binding domain that can interact with guide RNAs. A functional fragment or functional variant of a Cas protein is one that retains the ability to form a complex with a guide RNA and to bind to a target sequence in a target gene (and, for example, activate transcription of the target gene).

In addition to transcriptional activation domain as described elsewhere herein, Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus. In one example, the Cas protein portions of the chimeric Cas proteins disclosed herein have been modified to have decreased nuclease activity (e.g., nuclease activity is diminished by at least about 70%, 75%, 80%, 85%, 90%, 95%, 96%, 97%, 98%, 99%, or 100% compared to a wild type Cas protein) or to lack substantially all nuclease activity (i.e., nuclease activity is diminished by at least 90%, 95%, 97%, 98%, 99%, or 100% compared to a wild type Cas protein, or having no more than about 0%, 1%, 2%, 3%, 5%, or 10% of the nuclease activity of a wild type Cas protein). A nuclease-inactive Cas protein is a Cas protein having mutations known to be inactivating mutations in its catalytic (i.e., nuclease) domains (e.g., inactivating mutations in a RuvC-like endonuclease domain in a Cpf1 protein, or inactivating mutations in both an HNH endonuclease domain and a RuvC-like endonuclease domain in Cas9) or a Cas protein having nuclease activity diminished by at least about 97%, 98%, 99%, or 100% compared to a wild type Cas protein. Examples of different Cas protein mutations to reduce or substantially eliminate nuclease activity are disclosed below.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonfex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis*, or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis, Lachnospiraceae bacterium* MC20171, *Butyrivibrio proteoclasticus, Peregrinibacteria bacterium* GW2011_GWA2_33_10, Parcubacteria bacterium GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of or a property of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9. One example of a catalytically inactive Cas9 protein (dCas9) comprises, consists essentially of, or consist of an amino acid sequence at least 85%, 90%, 91%, 92%, 93%, 94%, 95%, 96%, 97%, 98%, 99%, or 100% identical to the dCas9 protein sequence set forth in SEQ ID NO: 2.

Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae*

*bacterium* ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, in addition to transcriptional activation domains, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AUl, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005)*Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10):1328-1332; Goodman et al. (2009) *Chembiochem.* 10(9):1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The labeled nucleic acid can be tethered to the C-terminus, the N-terminus, or to an internal region within the Cas protein. In one example, the labeled nucleic acid is tethered to the C-terminus or the N-terminus of the Cas protein. Likewise, the Cas protein can be tethered to the 5' end, the 3' end, or to an internal region within the labeled nucleic acid. That is, the labeled nucleic acid can be tethered in any orientation and polarity. For example, the Cas protein can be tethered to the 5' end or the 3' end of the labeled nucleic acid.

(2) Transcriptional Activation Domains

The chimeric Cas proteins disclosed herein can comprise one or more transcriptional activation domains. Transcriptional activation domains include regions of a naturally occurring transcription factor which, in conjunction with a DNA-binding domain (e.g., a catalytically inactive Cas protein complexed with a guide RNA), can activate transcription from a promoter by contacting transcriptional machinery either directly or through other proteins such as coactivators. Transcriptional activation domains also include functional fragments or variants of such regions of a transcription factor and engineered transcriptional activation domains that are derived from a native, naturally occurring transcriptional activation domain or that are artificially created or synthesized to activate transcription of a target gene. A functional fragment is a fragment that is capable of activating transcription of a target gene when operably linked to a suitable DNA-binding domain. A functional variant is a variant that is capable of activating transcription of a target gene when operably linked to a suitable DNA-binding domain.

A specific transcriptional activation domain for use in the chimeric Cas proteins disclosed herein comprises a VP64 transcriptional activation domain or a functional fragment or variant thereof. VP64 is a tetrameric repeat of the minimal activation domain from the herpes simplex VP16 activation domain. For example, the transcriptional activation domain can comprise, consist essentially of, or consist of an amino acid sequence at least 85%, 90%, 91%, 92%, 93%, 94%, 95%, 96%, 97%, 98%, 99%, or 100% identical to the VP64 transcriptional activation domain protein sequence set forth in SEQ ID NO: 3.

Other examples of transcriptional activation domains include herpes simplex virus VP16 transactivation domain, VP64 (quadruple tandem repeat of the herpes simplex virus VP16), a NF-κB p65 (NF-κB trans-activating subunit p65) activation domain, a MyoD1 transactivation domain, an HSF1 transactivation domain (transactivation domain from human heat-shock factor 1), RTA (Epstein Barr virus R transactivator activation domain), a SET7/9 transactivation domain, a p53 activation domain 1, a p53 activation domain 2, a CREB (cAMP response element binding protein) activation domain, an E2A activation domain, an NFAT (nuclear factor of activated T-cells) activation domain, and functional fragments and variants thereof. See, e.g., US 2016/0298125, US 2016/0281072, and WO 2016/049258, each of which is herein incorporated by reference in its entirety for all purposes. Other examples of transcriptional activation domains include Gcn4, MLL, Rtg3, Gln3, Oaf1, Pip2, Pdrl, Pdr3, Pho4, Leu3, and functional fragments and variants thereof. See, e.g., US 2016/0298125, herein incorporated by reference in its entirety for all purposes. Yet other examples of transcriptional activation domains include Spl, Vax, GATA4, and functional fragments and variants thereof. See, e.g., WO 2016/149484, herein incorporated by reference in its entirety for all purposes. Other examples include activation domains from Oct1, Oct-2A, AP-2, CTF1, P300, CBP, PCAF, SRC1, PvALF, ERF-2, OsGAI, HALF-1, Cl, AP1, ARF-5, ARF-6, ARF-7, ARF-8, CPRF1, CPRF4, MYC-RP/GP, and TRAB1PC4, and functional fragments and variants thereof. See, e.g., US 2016/0237456, EP3045537, and WO 2011/146121, each of which is incorporated by reference in its entirety for all purposes. Additional suitable transcriptional activation domains are also known. See, e.g., WO 2011/146121, herein incorporated by reference in its entirety for all purposes.

B. Chimeric Adaptor Proteins

Also provided are chimeric adaptor proteins that can bind to the guide RNAs disclosed elsewhere herein. The chimeric adaptor proteins disclosed herein are useful in dCas-synergistic activation mediator (SAM)-like systems to increase the number and diversity of transcriptional activation domains being directed to a target sequence within a target gene to activate transcription of the target gene. Nucleic acids encoding the chimeric adaptor proteins can be genomically integrated in a cell or non-human animal (e.g., a cell or non-human animal comprising a genomically integrated chimeric Cas protein expression cassette) as disclosed elsewhere herein, or the chimeric adaptor proteins or nucleic acids can be introduced into such cells and non-human animals using methods disclosed elsewhere herein (e.g., LNP-mediated delivery or AAV-mediated delivery).

Such chimeric adaptor proteins comprise: (a) an adaptor (i.e., adaptor domain or adaptor protein) that specifically binds to an adaptor-binding element within a guide RNA; and (b) one or more heterologous transcriptional activation domains. For example, such fusion proteins can comprise 1, 2, 3, 4, 5, or more transcriptional activation domains (e.g., two or more heterologous transcriptional activation domains or three or more heterologous transcriptional activation domains). In one example, such chimeric adaptor proteins can comprise: (a) an adaptor (i.e., an adaptor domain or adaptor protein) that specifically binds to an adaptor-binding element in a guide RNA; and (b) two or more transcriptional activation domains. For example, the chimeric adaptor protein can comprise: (a) an MS2 coat protein adaptor that specifically binds to one or more MS2 aptamers in a guide RNA (e.g., two MS2 aptamers in separate locations in a guide RNA); and (b) one or more (e.g., two or more transcriptional activation domains). For example, the two transcriptional activation domains can be p65 and HSF1 transcriptional activation domains or functional fragments or variants thereof. However, chimeric adaptor proteins in which the transcriptional activation domains comprise other transcriptional activation domains or functional fragments or variants thereof are also provided.

The one or more transcriptional activation domains can be fused directly to the adaptor. Alternatively, the one or more transcriptional activation domains can be linked to the adaptor via a linker or a combination of linkers or via one or more additional domains. Likewise, if two or more transcriptional activation domains are present, they can be fused directly to each other or can be linked to each other via a linker or a combination of linkers or via one or more additional domains. Linkers that can be used in these fusion proteins can include any sequence that does not interfere with the function of the fusion proteins. Exemplary linkers are short (e.g., 2-20 amino acids) and are typically flexible (e.g., comprising amino acids with a high degree of freedom such as glycine, alanine, and serine). Some specific examples of linkers comprise one or more units consisting of GGGS (SEQ ID NO: 4) or GGGGS (SEQ ID NO: 5), such as two, three, four, or more repeats of GGGS (SEQ ID NO: 4) or GGGGS (SEQ ID NO: 5) in any combination. Other linker sequences can also be used.

The one or more transcriptional activation domains and the adaptor can be in any order within the chimeric adaptor protein. As one option, the one or more transcriptional activation domains can be C-terminal to the adaptor and the adaptor can be N-terminal to the one or more transcriptional activation domains. For example, the one or more transcriptional activation domains can be at the C-terminus of the chimeric adaptor protein, and the adaptor can be at the N-terminus of the chimeric adaptor protein. However, the one or more transcriptional activation domains can be C-terminal to the adaptor without being at the C-terminus of the chimeric adaptor protein (e.g., if a nuclear localization signal is at the C-terminus of the chimeric adaptor protein). Likewise, the adaptor can be N-terminal to the one or more transcriptional activation domains without being at the N-terminus of the chimeric adaptor protein (e.g., if a nuclear localization signal is at the N-terminus of the chimeric adaptor protein). As another option, the one or more transcriptional activation domains can be N-terminal to the adaptor and the adaptor can be C-terminal to the one or more transcriptional activation domains. For example, the one or more transcriptional activation domains can be at the N-terminus of the chimeric adaptor protein, and the adaptor can be at the C-terminus of the chimeric adaptor protein. As yet another option, if the chimeric adaptor protein comprises two or more transcriptional activation domains, the two or more transcriptional activation domains can flank the adaptor.

Chimeric adaptor proteins can also be operably linked or fused to additional heterologous polypeptides. The fused or linked heterologous polypeptide can be located at the N-terminus, the C-terminus, or anywhere internally within the chimeric adaptor protein. For example, a chimeric adaptor protein can further comprise a nuclear localization signal. A specific example of such a protein comprises an MS2 coat protein (adaptor) linked (either directly or via an NLS) to a p65 transcriptional activation domain C-terminal to the MS2 coat protein (MCP), and HSF1 transcriptional activation domain C-terminal to the p65 transcriptional activation domain. Such a protein can comprise from N-terminus to C-terminus: an MCP; a nuclear localization signal; a p65 transcriptional activation domain; and an HSF1 transcriptional activation domain. For example, a chimeric adaptor protein can comprise, consist essentially of, or consist of an amino acid sequence at least 85%, 90%, 91%, 92%, 93%, 94%, 95%, 96%, 97%, 98%, 99%, or 100% identical to the MCP-p65-HSF1 chimeric adaptor protein sequence set forth in SEQ ID NO: 6.

Chimeric adaptor proteins can also be fused or linked to one or more heterologous polypeptides that provide for subcellular localization. Such heterologous polypeptides can include, for example, one or more nuclear localization signals (NLS) such as the SV40 NLS and/or an alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. An NLS can comprise, for example, a stretch of basic amino acids, and can be a monopartite sequence or a bipartite sequence. Optionally, the chimeric adaptor protein comprises two or more NLSs, including an NLS (e.g., an alpha-importin NLS) at the N-terminus and/or an NLS (e.g., an SV40 NLS) at the C-terminus.

Chimeric adaptor proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO2013/176772, each of which is herein incorporated by reference in its entirety for all purposes. As another example, chimeric adaptor proteins can be fused or linked to a heterologous polypeptide providing increased or decreased stability.

Chimeric adaptor proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AUl, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Chimeric adaptor proteins can also be tethered to labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005)*Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10):1328-1332; Goodman et al. (2009) *Chembiochem.* 10(9):1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The labeled nucleic acid can be tethered to the C-terminus, the N-terminus, or to an internal region within the chimeric adaptor protein. Likewise, the chimeric adaptor protein can be tethered to the 5' end, the 3' end, or to an internal region within the labeled nucleic acid. That is, the labeled nucleic acid can be tethered in any orientation and polarity.

(1) Adaptors

Adaptors (i.e., adaptor domains or adaptor proteins) are nucleic-acid-binding domains (e.g., DNA-binding domains and/or RNA-binding domains) that specifically recognize and bind to distinct sequences (e.g., bind to distinct DNA and/or RNA sequences such as aptamers in a sequence-specific manner). Aptamers include nucleic acids that, through their ability to adopt a specific three-dimensional conformation, can bind to a target molecule with high affinity and specificity. Such adaptors can bind, for example, to a specific RNA sequence and secondary structure. These sequences (i.e., adaptor-binding elements) can be engineered into a guide RNA. For example, an MS2 aptamer can be engineered into a guide RNA to specifically bind an MS2 coat protein (MCP). For example, the adaptor can comprise, consist essentially of, or consist of an amino acid sequence at least 85%, 90%, 91%, 92%, 93%, 94%, 95%, 96%, 97%, 98%, 99%, or 100% identical to the MCP sequence set forth in SEQ ID NO: 7.

Some specific examples of adaptors and targets include RNA-binding protein/aptamer combinations that exist within the diversity of bacteriophage coat proteins. For example, the following adaptor proteins or functional fragments or variants thereof can be used: MS2 coat protein (MCP), PP7, Qβ, F2, GA, fr, JP501, M12, R17, BZ13, JP34, JP500, KU1, M11, MX1, TW18, VK, SP, FI, ID2, NL95, TW19, AP205, φCb5, ΦCb8r, ΦCb12r, ΦCb23r, 7s, and PRR1. See, e.g., WO 2016/049258, herein incorporated by reference in its entirety for all purposes. A functional fragment or functional variant of an adaptor protein is one that retains the ability to bind to a specific adaptor-binding element (e.g., ability to bind to a specific adaptor-binding sequence in a sequence-specific manner). For example, a PP7 *Pseudomonas* bacteriophage coat protein variant can be used in which amino acids 68-69 are mutated to SG and amino acids 70-75 are deleted from the wild type protein. See, e.g., Wu et al. (2012) *Biophys J* 102(12):2936-2944 and Chao et al. (2007) *Nature Structural & Molecular Biology* 15(1):103-105, each of which is herein incorporated by reference in its entirety for all purposes. Likewise, an MCP variant may be used, such as a N55K mutant. See, e.g., Spingola and Peabody (1994) *J Biol Chem* 269(12):9006-9010, herein incorporated by reference in its entirety for all purposes.

Other examples of adaptor proteins that can be used include all or part of (e.g., the DNA-binding from) endoribonuclease Csy4 or the lambda N protein. See, e.g., U S 2016/0312198, herein incorporated by reference in its entirety for all purposes.

(2) Transcriptional Activation Domains

The chimeric adaptor proteins disclosed herein comprise one or more transcriptional activation domains. Such transcriptional activation domains can be naturally occurring transcriptional activation domains, can be functional fragments or functional variants of naturally occurring transcriptional activation domains, or can be engineered or synthetic transcriptional activation domains. Transcriptional activation domains that can be used include those described for use in chimeric Cas proteins elsewhere herein.

A specific transcriptional activation domain for use in the chimeric adaptor proteins disclosed herein comprises p65 and/or HSF1 transcriptional activation domains or functional fragments or variants thereof. The HSF1 transcriptional activation domain can be a transcriptional activation domain of human heat shock factor 1 (HSF1). The p65 transcriptional activation domain can be a transcriptional activation domain of transcription factor p65, also known as nuclear factor NF-kappa-B p65 subunit encoded by the RELA gene. As one example, a transcriptional activation domain can comprise, consist essentially of, or consist of an amino acid sequence at least 85%, 90%, 91%, 92%, 93%, 94%, 95%, 96%, 97%, 98%, 99%, or 100% identical to the p65 transcriptional activation domain protein sequence set forth in SEQ ID NO: 8. As another example, a transcriptional activation domain can comprise, consist essentially of, or consist of an amino acid sequence at least 85%, 90%, 91%, 92%, 93%, 94%, 95%, 96%, 97%, 98%, 99%, or 100% identical to the HSF1 transcriptional activation domain protein sequence set forth in SEQ ID NO: 9.

C. Guide RNAs and Guide RNA Arrays

Also provided are guide RNAs or guide RNA arrays that can bind to the chimeric Cas proteins and chimeric adaptor proteins disclosed elsewhere herein to activate transcription of target genes. Nucleic acids encoding the guide RNAs can be genomically integrated in a cell or non-human animal (e.g., a SAM-ready cell or non-human animal) as disclosed elsewhere herein, or the guide RNAs or nucleic acids can be introduced into such cells and non-human animals using methods disclosed elsewhere herein (e.g., LNP-mediated delivery or AAV-mediated delivery). The delivery method can be selected to provide tissue-specific delivery of the recombinase as disclosed elsewhere herein.

A nucleic acid encoding the guide RNAs or guide RNA array can encode one or more guide RNAs (or if guide RNAs are being introduced into the cell or non-human animal, one or more guide RNAs can be introduced). For example, 2 or more, 3 or more, 4 or more, or 5 or more guide RNAs can be encoded or introduced. Each guide RNA coding sequence can be operably linked to the same promoter (e.g., a U6 promoter) or a different promoter (e.g., each guide RNA coding sequence is operably linked to its own U6 promoter). Two or more of the guide RNAs can target a different target sequence in a single target gene. For example, 2 or more, 3 or more, 4 or more, or 5 or more guide RNAs can each target a different target sequence in a single target gene. Similarly, the guide RNAs can target multiple target genes (e.g., 2 or more, 3 or more, 4 or more, or 5 or more target genes). Examples of guide RNA target sequences are disclosed elsewhere herein.

(1) Guide RNAs

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 10). Any of the DNA-targeting segments disclosed herein can be joined to the 5' end of SEQ ID NO: 10 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of (SEQ ID NO: 11)
AGCAUAGCAAGUUAAAAUAAGGCUAGUCCGUUAUCAACUUGAAAAAGUGG

CACCGAGUCGGUGCUUU.

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment and a scaffold sequence (i.e., the protein-binding or Cas-binding sequence of the guide RNA). For example, such guide RNAs can have a 5' DNA-targeting segment joined to a 3' scaffold sequence. Exemplary scaffold sequences comprise, consist essentially of, or consist of: GUUUUAGAGCUAGAAAUAGCAAGUUAAAAUAAGGCUAGUCCGUUAUCAACUUGA AAAAGUGGCACCGAGUCGGUGCU (version 1; SEQ ID NO: 12); GUUGGAACCAUUCAAAACAG-CAUAGCAAGUUAAAAUAAGGCUAGU-CCGUUAUCA ACUUGAAAAAGUGGCACCGAGUCG-GUGC (version 2; SEQ ID NO: 13); GUUUUAGAGCUA-GAAAUAGCAAGUUAAAAUAAGGCUAGU-CCGUUAUCAACUUGA AAAAGUGGCACCGAGUCG-GUGC (version 3; SEQ ID NO: 14); and GUUUAAGAGCUAUGCUGGAAACAG-CAUAGCAAGUUUAAAUAAGGCUAGUCCGUU AUCAACUUGAAAAAGUGGCACCGAGUCGGUGC (version 4; SEQ ID NO: 15). Guide RNAs targeting any of the guide RNA target sequences disclosed herein can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of the above scaffold sequences to form a single guide RNA (chimeric guide RNA).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, such as transcriptional activators); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs. For example, Cas mRNAs can be modified by depletion of uridine using synonymous codons.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Reports* 22:1-9, each of which is herein incorporated by reference in its entirety for all purposes.

In some guide RNAs (e.g., single guide RNAs), at least one loop (e.g., two loops) of the guide RNA is modified by insertion of a distinct RNA sequence that binds to one or more adaptors (i.e., adaptor proteins or domains). Such adaptor proteins can be used to further recruit one or more heterologous functional domains, such as transcriptional activation domains. Examples of fusion proteins comprising such adaptor proteins (i.e., chimeric adaptor proteins) are disclosed elsewhere herein. For example, an MS2-binding loop ggccAACAUGAGGAUCACCCAUGU-CUGCAGggcc (SEQ ID NO: 16) may replace nucleotides+13 to +16 and nucleotides+53 to +56 of the sgRNA scaffold (backbone) set forth in SEQ ID NO: 12 or SEQ ID NO: 14 or the sgRNA backbone for the *S. pyogenes* CRISPR/Cas9 system described in WO 2016/049258 and Konermann et al. (2015) Nature 517(7536):583-588, each of which is herein incorporated by reference in its entirety for all purposes. See, e.g., FIG. 7. The guide RNA numbering used herein refers to the nucleotide numbering in the guide RNA scaffold sequence (i.e., the sequence downstream of the DNA-targeting segment of the guide RNA). For example, the first nucleotide of the guide RNA scaffold is +1, the second nucleotide of the scaffold is +2, and so forth. Residues corresponding with nucleotides+13 to +16 in SEQ ID NO: 12 or SEQ ID NO: 14 are the loop sequence in the region spanning nucleotides+9 to +21 in SEQ ID NO: 12 or SEQ ID NO: 14, a region referred to herein as the tetraloop. Residues corresponding with nucleotides+53 to +56 in SEQ ID NO: 12 or SEQ ID NO: 14 are the loop sequence in the region spanning nucleotides+48 to +61 in SEQ ID NO: 12 or SEQ ID NO: 14, a region referred to herein as the stem loop 2. Other stem loop sequences in in SEQ ID NO: 12 or SEQ ID NO: 14 comprise stem loop 1 (nucleotides+33 to +41) and stem loop 3 (nucleotides+63 to +75). The resulting structure is an sgRNA scaffold in which each of the tetraloop and stem loop 2 sequences have been replaced by an MS2 binding loop. The tetraloop and stem loop 2 protrude from the Cas9 protein in such a way that adding an MS2-binding loop should not interfere with any Cas9 residues. Additionally, the proximity of the tetraloop and stem loop 2 sites to the DNA indicates that localization to these locations could result in a high degree of interaction between the DNA and any recruited protein, such as a transcriptional activator.

Thus, in some sgRNAs, nucleotides corresponding to +13 to +16 and/or nucleotides corresponding to +53 to +56 of the guide RNA scaffold set forth in SEQ ID NO: 12 or SEQ ID NO: 14 or corresponding residues when optimally aligned with any of these scaffold/backbones are replaced by the distinct RNA sequences capable of binding to one or more adaptor proteins or domains. Alternatively or additionally, adaptor-binding sequences can be added to the 5' end or the 3' end of a guide RNA. An exemplary guide RNA scaffold comprising MS2-binding loops in the tetraloop and stem loop 2 regions can comprise, consist essentially of, or consist of the sequence set forth in SEQ ID NO: 40. An exemplary generic single guide RNA comprising MS2-binding loops in the tetraloop and stem loop 2 regions can comprise, consist essentially of, or consist of the sequence set forth in SEQ ID NO: 63.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

(2) Guide RNA Target Sequences

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

It can be preferable for the target sequence to be adjacent to the transcription start site of a gene. For example, the target sequence can be within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair of the transcription start site, within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair upstream of the transcription start site, or within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair downstream of the transcription start site. Optionally, the target sequence is within the region 200 base pairs upstream of the transcription start site and 1 base pair downstream of the transcription start site (−200 to +1).

The target sequence can be within any gene desired to be targeted for transcriptional activation. In some cases, a target gene may be one that is a non-expressing gene or a weakly expressing gene (e.g., only minimally expressed above background, such as 1.1-fold, 1.2-fold, 1.3-fold, 1.4-fold, 1.5-fold, 1.6-fold, 1.7-fold, 1.8-fold, 1.9-fold, or 2-fold). The target gene may also be one that is expressed at low levels compared to a control gene. The target gene may also be one that is epigenetically silenced. The term "epigenetically silenced" refers to a gene that is not being transcribed or is being transcribed at a level that is decreased with respect to the level of transcription of the gene in a control sample (e.g., a corresponding control cell, such as a normal cell), due to a mechanism other than a genetic change such as a mutation. Epigenetic mechanisms of gene silencing are well known and include, for example, hypermethylation of CpG dinucleotides in a CpG island of the 5' regulatory region of a gene and structural changes in chromatin due, for example, to histone acetylation, such that gene transcription is reduced or inhibited.

Target genes can include genes expressed in particular organs or tissues, such as the liver. Target genes can include disease-associated genes. A disease-associated gene refers to any gene that yields transcription or translation products at an abnormal level or in an abnormal form in cells derived from a disease-affected tissues compared with tissues or cells of a non-disease control. It may be a gene that becomes expressed at an abnormally high level, where the altered expression correlates with the occurrence and/or progression of the disease. A disease-associated gene also refers to a gene possessing a mutation or genetic variation that is responsible for the etiology of a disease. The transcribed or translated products may be known or unknown, and may be at a normal or abnormal level. For example, target genes can be genes associated with protein aggregation diseases and disorders, such as Alzheimer's disease, Parkinson's disease, Huntington's disease, amyotrophic lateral sclerosis, prion diseases, and amyloidoses such as transthyretin amyloidosis (e.g., Ttr). Target genes can also be genes involved in pathways related to a disease or condition, such as hypercholesterolemia or atherosclerosis, or genes that when overexpressed can model such diseases or conditions. Target genes can also be genes expressed or overexpressed in one or more types of cancer. See, e.g., Santarius et al. (2010) *Nat. Rev. Cancer* 10(1):59-64, herein incorporated by reference in its entirety for all purposes.

One specific example of such a target gene is the Ttr gene. Optionally, the Ttr gene can comprise a pathogenic mutation (e.g., a mutation causing amyloidosis). Examples of such mutations are provided, e.g., in WO 2018/007871, herein incorporated by reference in its entirety for all purposes. An exemplary human TTR protein and an exemplary human TTR gene are identified by UniProt ID P02766 and Entrez Gene ID 7276, respectively. An exemplary mouse TTR protein and an exemplary mouse Ttr gene are identified by UniProt ID P07309 and Entrez Gene ID 22139, respectively. Transthyretin (TTR) is a protein found in the serum and cerebrospinal fluid that carries thyroid hormone and retinol-binding protein to retinol. The liver secretes TTR into the blood, while the choroid plexus secretes it into the cerebrospinal fluid. TTR is also produced in the retinal pigmented epithelium and secreted into the vitreous. Misfolded and aggregated TTR accumulates in multiple tissues and organs in the amyloid diseases senile systemic amyloidosis (SSA), familial amyloid polyneuropathy (FAP), and familial amyloid cardiomyopathy (FAC). Transthyretin (TTR) is a 127-amino acid, 55 kDa serum and cerebrospinal fluid transport protein primarily synthesized by the liver but also produced by the choroid plexus. It has also been referred to as prealbumin, thyroxine binding prealbumin, ATTR, TBPA, CTS, CTS1, HEL111, HsT2651, and PALB. In its native state, TTR exists as a tetramer. In homozygotes, homo-tetramers comprise identical 127-amino-acid beta-sheet-rich subunits. In heterozygotes, TTR tetramers can be made up of variant and/or wild-type subunits, typically combined in a statistical fashion. TTR is responsible for carrying thyroxine (T4) and retinol-bound RBP (retinol-binding protein) in both the serum and the cerebrospinal fluid. Examples of guide RNA target sequences (not including PAM) in the mouse Ttr gene are set forth in SEQ ID NOS: 34, 35, and 36, respectively. SEQ ID NO: 34 is located −63 of the Ttr transcription start site (genomic coordinates: build mm10, chr18, + strand, 20665187-20665209), SEQ ID NO: 35 is located −134 of the Ttr transcription start site (genomic coordinates: build mm10, chr18, + strand, 20665116-20665138), and SEQ ID NO: 36 is located −112 of the Ttr transcription start site (genomic coordinates: build mm10, chr18, + strand, 20665138-20665160). Guide RNA DNA-targeting segments corresponding to the guide RNA target sequences set forth in SEQ ID NOS: 34, 35, and 36, respectively, are set forth in SEQ ID NOS: 41, 42, and 43, respectively. Examples of single guide RNAs comprising these DNA-targeting segments are set forth in SEQ ID NOS: 37, 38, and 39, respectively.

Other examples of target genes are proprotein convertase subtilisin/kexin type 9 (PCSK9) and low-density lipoprotein (LDL) receptor (LDLR). An exemplary human PCSK9 protein and an exemplary human PCSK9 gene are identified by UniProt ID Q8NBP7 and Entrez Gene ID 255738, respectively. An exemplary mouse PCSK9 protein and an exemplary mouse Pcsk9 gene are identified by UniProt ID Q80W65 and Entrez Gene ID 100102, respectively. An exemplary human LDLR protein and an exemplary human LDLR gene are identified by UniProt ID P01130 and Entrez Gene ID 3949, respectively. An exemplary mouse LDLR protein and an exemplary mouse Ldlr gene are identified by UniProt ID P35951 and Entrez Gene ID 16835, respectively.

LDLR mediates the endocytosis of cholesterol-rich LDL and thus maintains the plasma level of LDL. This occurs in all nucleated cells, but mainly in the liver, which removes ~70% of LDL from the circulation. The LDL receptor binds and initiates ingestion of LDL particles from extracellular fluid into cells, thus reducing LDL particle concentrations. When LDL binds to LDLR, it induces internalization of the LDLR-LDL complex within an endosome. The acidity of the endosomal environment induces LDLR to adopt a hairpin conformation. The conformational change causes LDLR to release its LDL ligand, and the receptor is recycled back to the plasma membrane. In humans, LDL is directly involved in the development of atherosclerosis, which is the process responsible for the majority of cardiovascular diseases, due to the accumulation of LDL-cholesterol in the blood.

When PCSK9 binds to the LDLR, PCSK9 prevents the conformational change of the receptor-ligand complex. This inhibition redirects the LDLR to the lysosome instead. PCSK9 plays a major regulatory role in cholesterol homeostasis, mainly by reducing LDLR levels on the plasma membrane. Reduced LDLR levels result in decreased metabolism of LDL particles, which can lead to hypercholesterolemia. If PCSK9 is blocked, more LDLRs are recycled and are present on the surface of cells to remove LDL particles from the extracellular fluid. Therefore, blocking PCSK9 can lower blood LDL particle concentrations, whereas increasing expression of PCSK9 can increase blood LDL particle concentrations. Thus, activating expression of Pcsk9 as described elsewhere herein can be used to model hypercholesterolemia (the presence of high levels of cholesterol in the blood), which can lead to atherosclerosis (hardening of arteries).

Examples of guide RNA target sequences (not including PAM) in the mouse Ldlr gene are set forth in SEQ ID NOS: 75, 76, and 77, respectively. Guide RNA DNA-targeting segments corresponding to the guide RNA target sequences set forth in SEQ ID NOS: 75, 76, and 77, respectively, are set forth in SEQ ID NOS: 81, 82, and 83, respectively. Examples of single guide RNAs comprising these DNA-targeting segments are set forth in SEQ ID NOS: 78, 79, and 80, respectively.

Examples of guide RNA target sequences (not including PAM) in the mouse Pcsk9 gene are set forth in SEQ ID NOS: 89, 90, and 91, respectively. Guide RNA DNA-targeting segments corresponding to the guide RNA target sequences set forth in SEQ ID NOS: 89, 90, and 91, respectively, are set forth in SEQ ID NOS: 95, 96, and 97, respectively. Examples of single guide RNAs comprising these DNA-targeting segments are set forth in SEQ ID NOS: 92, 93, and 94, respectively.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-CC$N_2$-3', where $N_2$ is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are G$N_{19}$NGG (SEQ ID NO: 17) or $N_{20}$NGG (SEQ ID NO: 18). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., GG$N_{20}$NGG; SEQ ID NO: 19) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 17-19, including the 5' G or GG and the 3' GG or NGG. Yet other guide RNA target sequences plus PAMs can have between 14 and 20 nucleotides in length of SEQ ID NOS: 17-19.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

D. Recombinases and Recombinase Deleter Non-Human Animals

Cells or non-human animals comprising a chimeric Cas protein expression cassette, a chimeric adaptor protein expression cassette, a SAM expression cassette, a guide RNA expression cassette, or a recombinase expression cassette in which the cassette is downstream of a polyadenylation signal or transcription terminator flanked by recombinase recognition sites recognized by a site-specific recombinase as disclosed herein can further comprise a recombinase expression cassette that drives expression of the site-specific recombinase. A nucleic acid encoding the recombinase can be genomically integrated, or the recombinase or nucleic acids can be introduced into such cells and non-human animals using methods disclosed elsewhere herein (e.g., LNP-mediated delivery or AAV-mediated delivery). The delivery method can be selected to provide tissue-specific delivery of the recombinase as disclosed elsewhere herein.

Site-specific recombinases include enzymes that can facilitate recombination between recombinase recognition sites, where the two recombination sites are physically separated within a single nucleic acid or on separate nucleic acids. Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

The recombinase expression cassette can be integrated at a different target genomic locus from other expression cassettes disclosed herein, or it can be genomically integrated at the same target locus (e.g., a Rosa26 locus, such as integrated in the first intron of the Rosa26 locus). For example, the cell or non-human animal can be heterozygous for each of a SAM expression cassette (or chimeric Cas protein expression cassette or chimeric adaptor protein expression cassette) and the recombinase expression cassette, with one allele of the target genomic locus comprising the SAM expression cassette, and a second allele of the target genomic locus comprising the recombinase expression cassette expression cassette. Likewise, the cell or non-human animal can be heterozygous for each of a guide RNA expression cassette (e.g., guide RNA array expression cassette) and the recombinase expression cassette, with one allele of the target genomic locus comprising the guide RNA expression cassette, and a second allele of the target genomic locus comprising the recombinase expression cassette expression cassette.

The recombinase gene in a recombinase expression cassette can be operably linked to any suitable promoter. Examples of promoters are disclosed elsewhere herein. For example, the promoter can be a tissue-specific promoter or a developmental-stage-specific promoter. Such promoters are advantageous because they can selectively activate transcription of a target gene in a desired tissue or only at a desired developmental stage. For example, in the case of Cas proteins, this can reduce the possibility of Cas-mediated toxicity in vivo. A non-limiting list of exemplary promoters for mouse recombinase delete strains is provided in Table 2.

TABLE 2

Exemplary Promoters Used in Mouse Recombinase Deleter Strains.

| Promoter (Species | Site of Expression |
|---|---|
| ACTA1 (human) | Adult striated muscle fibers and embryonic striated muscle cells of the somites and heart |
| Adipoq, adiponectin, C1Q and collagen domain containing (mouse) | White adipose tissue (WAT) and brown adipose tissue (BAT) |
| Agrp (mouse) | ArGP neurons in the hypothalamus |
| Alb, albumin (rat) | Liver |
| Alb1, albumin (mouse) | Liver |
| Amh (mouse) | Testis Sertoli cells |
| Aqp2 (mouse) | Kidney cells (collecting duct, left) and testes (sperm, right). |
| Calb2, calbindin 2 | Calretinin interneurons in the brain and cortex |
| Camk2a, calcium/calmodulin-dependent protein kinase II alpha (mouse) | Forebrain, specifically CA1 pyramidal cell layer in hippocampus |
| Cck, cholecystokinin (mouse) | Cholecystokinin positive neurons (interneurons) of the cortex and in adult spinal cord and embryonic day 15.5 spinal cord and heart |
| CD2, CD2 molecule (human) | T cells and B cells (all committed B cell and T cell progenitors) |
| Cd19 | B cells |
| Cdh5, cadherin 5 | Endothelium of developing and quiescent vessels, and a subset of hematopoietic cells |
| Chdl6 (mouse) | Renal tubules, especially collecting ducts, loops of Henle and distal tubules |
| Chat, choline acetyltransferase (mouse) | Cholinergic neurons |
| Ckmm (mouse) | Skeletal and cardiac muscle. |
| Cort, cortistatin | Cort-expressing cells (CST positive neurons) |
| Crh, corticotropin releasing hormone | CRH-positive neurons |
| Cspg4 (mouse) | NG2-expressing glia (polydendrocytes, oligodendrocyte progenitor cells) in central nervous system and NG2-expressing cells in other organs; Corpus Callosum; CNS and other tissues such as testes and blood vessels |
| Cyp39a1, cytochrome P450, family 39, subfamily a, polypeptide 1 (mouse) | Cerebral cortex, hippocampus, striatum, olfactory bulb, and cerebellum |
| dlx6a, distal-less homeobox gene 6a | GABAergic forebrain neurons |
| Ella, adenovirus (adenovirus) | Wide range of tissues, including the germ cells that transmit the genetic alteration to progeny |
| Emx1, empty spiracles homolog 1 (Drosophila) | Neurons of neocortex and hippocampus, and in glial cells of pallium |
| En1, engrailed 1 | Spinal cord V1 interneurons, the embryonic mesencephalon and rhombomere 1 by E9, as well as in the ventral ectoderm of the limbs, in a subset of somite cells, and some mesoderm-derived tissues |
| Fabp4, fatty acid binding protein 4 | Brown and white adipose tissue. |
| Foxdl (mouse) | Kidney development in metanephric mesenchyme in cells fated to become stromal cells of kidney, and multiple organs throughout body |
| Foxp3 (mouse) | Cd4 + Cd25<high>Cd127<low>T cells from the lymph nodes, spleen and thymus; ovary |
| Gad2, glutamic acid decarboxylase 2 | Gad2-positive neurons |

TABLE 2-continued

Exemplary Promoters Used in Mouse Recombinase Deleter Strains.

| Promoter (Species | Site of Expression |
|---|---|
| GFAP, glial fibrillary acidic protein (human) | Central nervous system, including astrocytes, oligodendroglia, ependyma and some neurons; also periportal cells of the liver |
| Gfap (mouse) | Astrocytes in the brain and spinal cord, as well as postnatal and adult GFAP-expressing neural stem cells and their progeny in the brain; cartilage primordium at e15.5; thymus, myocardium, eye lens, peripheral nerves embedded in bladder and intestinal muscle of adults |
| Gfap (mouse) | Most astrocytes throughout the healthy brain and spinal cord and to essentially all astrocytes after Central Nervous System (CNS) injury; subpopulation of the adult stems in the subventricular zone |
| Grik4, glutamate receptor, ionotropic, kainate 4 (mouse) | At 14 days old in area CA3 of the hippocampus, and at 8 weeks of age, recombination is observed in nearly 100% of pyramidal cells in area CA3; other brain areas |
| Hspa2, heat shock protein 2 (mouse) | Leptotene/zygotene spermatocytes |
| Ins2, insulin 2 (rat) | Pancreatic beta cells, as well as the hypothalamus |
| Itgax, integrin alpha X (mouse) | CD8−, CD8+ dendritic cells, tissue derived dendritic cells from lymph nodes, lung and epidermis and plasmacytoid dendritic cells |
| Kap (mouse) | Proximal tubule cells of the renal cortex in male mice; uterus and liver |
| KRT14, keratin 14 (human) | Skin, the oral ectoderm including the dental lamina at 11.75 d.p.c., and dental epithelium by 14.5 d.p.c. |
| Lck, lymphocyte protein tyrosine kinase (mouse) | Thymocytes |
| Lck (mouse) | Thymus |
| Lepr (mouse) | Hypothalamus (arcuate, dorsomedial, lateral, and ventromedial nuclei), limbic and cortical brain regions (basolateral amygdaloid nucleus, piriform cortex, and lateral entorhinal cortex), and retrosplenial cortex |
| Lyve1 (mouse) | Lymphatic endothelium |
| Lyz2, Lysozyme 2 (mouse) | Myeloid cells, including monocytes, mature macrophages and granulocytes |
| MMTV | Mammary gland, salivary gland, seminal vesicle, skin, erythrocytes, B cells and T cells; lower in lung, kidney, liver and brain tissues |
| Mnx1, motor neuron and pancreas homeobox 1 (mouse) | Motor neurons |
| Myf5, myogenic factor 5 | Skeletal muscle and the dermis, and in several ectopic locations |
| Myh6 (mouse) | Cardiac tissue |
| Nes, nestin (rat) | Central and peripheral nervous system; a few isolated kidney and heart cells |
| Neurog3, neurogenin 3, (rat) | Islets of the adult pancreas, small intestine enteroendocrine cells, endocrine portions of the stomach, all pancreatic endocrine cells, and some non-endocrine intestinal cells |
| Nkx2-1 | Cre recombinase activity is directed to brain interneuron progenitors, developing lung, thyroid, and pituitary by the Nkx2.1 promoter/enhancer regions |
| NPHS2 (human) | Podocytes during late capillary loop stage of glomerular development and podocytes of mature glomeruli |
| Nr5a1, Nuclear receptor subfamily 5 group A member 1 (mouse) | Ventromedial Hypothalamus, Cortex, Adrenal Gland, Pituitary Gland and Gonads |
| Omp, Olfactory Marker Protein (mouse) | Mature olfactory sensory neurons |
| Pax3, paired box gene 3 | Dorsal neural tube and somites of E9 to 11.5 embryos and cardiac neural crest cells and colonic epithelia of E11.5 embryos |
| Pf4, platelet factor 4 (mouse) | Megakaryocytes |
| Pomc1 (mouse) | POMC neurons in the arcuate nucleus of the hypothalamus and scattered in the dentate gyrus of the hippocampus |
| Prdm1 (mouse) | Primordial germ cells |
| Prm (mouse) | Male germ line |
| Pvalb, parvalbumin | Neurons that express parvalbumin, such as interneurons in the brain and proprioceptive afferent sensory neurons in the dorsal root ganglia |
| Scnn1a (mouse) | Cortex, thalamus, midbrain, and cerebellum |
| Shh, sonic hedgehog | Endogenous Shh expression patterns |
| Sim1, single-minded homolog 1 (Drosophila) (mouse) | Paraventricular hypothalamus and other parts of the brain |
| Slc6a3, solute carrier family 6 (neurotransmitter transporter, dopamine), member 3 | Dopaminergic cell groups (substantia nigra (SN) and ventral tegmental area (VTA), as well as in the retrorubral field) |
| Slc17a6 (mouse) | Excitatory glutamatergic neuron cell bodies |
| Sst, somatostatin | Somatostatin positive neurons (including dendritic inhibitory interneurons such as Martinotti cells and Oriens-Lacunosum-Moleculare cells) |
| Stra8 (mouse) | Postnatal, premeiotic, male germ cells |
| Syn1 (rat) | Neuronal cells, including brain, spinal cord and DRGs, as early as E12.5, as well as in neurons in adult |
| Tagln, transgelin (mouse) | Smooth muscle |
| Tagln (mouse) | Adult smooth muscle cells (such as arteries, veins, and visceral organs) and cardiac myocytes |
| Tek (mouse) | Endothelial cells during embryogenesis and adulthood |
| Thy1 (mouse) | Neurons of the cortex and hippocampus |

TABLE 2-continued

Exemplary Promoters Used in Mouse Recombinase Deleter Strains.

| Promoter (Species | Site of Expression |
|---|---|
| Twist2, twist basic helix-loop-helix transcription factor 2 | Mesoderm as early as embryonic day 9.5, in mesodermal tissues such as branchial arches and somites, and in condensed mesenchyme-derived chondrocytes and osteoblasts |
| Vav1 (mouse) | Variegated germline (testis and ovaries), and heart and gut |
| Vil1, villin 1 (mouse) | Villi and crypts of the small and large intestine |
| Vip, vasoactive intestinal polypeptide | Some GABAergic interneurons |
| Wnt1, wingless-related MMTV integration site 1 (mouse) | Embryonic neural tube, midbrain, dorsal and ventral midlines of the midbrain and caudal diencephalon, the mid-hindbrain junction and dorsal spinal cord |
| Wnt1 (mouse) | Developing neural crest and midbrain |
| Krt17, keratin 17 (mouse) | Endogenous keratin 17 expression patterns |
| Osr2, odd-skipped related 2 (Drosophila), mouse, laboratory | Developing palate and urogenital tract |
| Trp63, transformation related protein 63 (mouse) | Endogenous Trp63 expression patterns |
| Prrx1, paired related homeobox 1 (rat) | Early limb bud mesenchyme and in a subset of craniofacial mesenchyme, along with limited female germline expression |
| Tbx22, T-box transcription factor 22 (mouse) | Endogenous Tbx22 expression patterns |
| Tgfb3, transforming growth factor, beta 3 (mouse) | Heart, pharyngeal arches, otic vesicle, mid brain, limb buds, midline palatal epithelium, and whisker follicles during embryo and fetus development |
| Wnt1, wingless-related MMTV integration site 1 (mouse) | Embryonic neural tube, midbrain, caudal diencephalon, the mid-hindbrain junction, dorsal spinal cord, and neural crest cells |
| ACTB, actin, beta (chicken) | Most tissue types |
| Col2a1, collagen, type II, alpha 1 (mouse) | Cells of chondrogenic lineage (cartilage) during embryogenesis and postnatally. |
| Dlx5, distal-less homeobox 5 | Cortex |
| KRT14, keratin 14 (human) | Keratinocytes |
| Lgr5, leucine rich repeat containing G protein coupled receptor 5 | Crypt base columnar cells in small intestine (stem cells of the small intestine) and colon |
| Myh6, myosin, heavy polypeptide 6, (mouse) | Developing and adult heart |
| Plp1, proteolipid protein (myelin) 1 (mouse) | Oligodendrocytes and Schwann cells |
| UBC, ubiquitin C (human) | All tissue types |
| Wfs1, Wolfram syndrome 1 homolog (human) | Cortex, hippocampus, striatum, thalamus and cerebellum |
| Gt(ROSA)26Sor (mouse) | Most tissue types preimplantation onward, including cells of developing germline |
| Chicken beta-actin promoter and an hCMV immediate early enhancer | Ubiquitous |

E. Nucleic Acids Encoding Chimeric Cas Protein, Chimeric Adaptor Protein, Guide RNA, Synergistic Activation Mediator, or Recombinase Also provided are nucleic acids encoding a chimeric Cas protein, a chimeric adaptor protein, a guide RNA, a recombinase, or any combination thereof. Chimeric Cas proteins, chimeric adaptor proteins, guide RNAs, and recombinases are described in more detail elsewhere herein. For example, the nucleic acids can be chimeric Cas protein expression cassettes, chimeric adaptor protein expression cassettes, synergistic activation mediator (SAMN) expression cassettes comprising nucleic acids encoding both a chimeric Cas protein and a chimeric adaptor protein, guide RNA or guide RNA array expression cassettes, recombinase expression cassettes, or any combination thereof. Such nucleic acids can be RNA (e.g., messenger RNA (mRNA)) or DNA, can be single-stranded or double-stranded, and can be linear or circular. DNA can be part of a vector, such as an expression vector or a targeting vector. The vector can also be a viral vector such as adenoviral, adeno-associated viral, lentiviral, and retroviral vectors. When any of the nucleic acids disclosed herein is introduced into a cell, the encoded chimeric DNA-targeting protein, chimeric adaptor protein, or guide RNA can be transiently, conditionally, or constitutively expressed in the cell.

Optionally, the nucleic acids can be codon optimized for efficient translation into protein in a particular cell or organism. For example, the nucleic acid can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence.

The nucleic acids or expression cassettes can be stably integrated into the genome (i.e., into a chromosome) of the cell or non-human animal or it can be located outside of a chromosome (e.g., extrachromosomally replicating DNA). The stably integrated expression cassettes or nucleic acids can be randomly integrated into the genome of the non-human animal (i.e., transgenic), or they can be integrated into a predetermined region of the genome of the non-human animal (i.e., knock in). In one example, a nucleic acid or expression cassette is stably integrated into a safe harbor locus as described elsewhere herein. The target genomic locus at which a nucleic acid or expression cassette is stably integrated can be heterozygous for the nucleic acid or expression cassette or homozygous for the nucleic acid or expression cassette. For example, a target genomic locus or a cell or non-human animal can be heterozygous for a SAM expression cassette and heterozygous for a guide RNA expression cassette, optionally with each being at the same target genomic locus on different alleles.

A nucleic acid or expression cassette described herein can be operably linked to any suitable promoter for expression in vivo within a non-human animal or ex vivo within a cell. The non-human animal can be any suitable non-human animal as described elsewhere herein. As one example, a nucleic acid or expression cassette (e.g., a chimeric Cas protein expression cassette, a chimeric adaptor protein expression cassette, or a SAM cassette comprising nucleic acids encoding both a chimeric Cas protein and a chimeric adaptor protein) can be operably linked to an endogenous promoter at a target genomic locus, such as a Rosa26 promoter. Alternatively, cassette nucleic acid or expression cassette can be operably linked to an exogenous promoter, such as a constitutively active promoter (e.g., a CAG promoter or a U6 promoter), a conditional promoter, an inducible promoter, a temporally restricted promoter (e.g., a developmentally regulated promoter), or a spatially restricted promoter (e.g., a cell-specific or tissue-specific promoter). Such promoters are well-known and are discussed elsewhere herein. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters.

For example, a nucleic acid encoding a guide RNA can be operably linked to a U6 promoter, such as a human U6 promoter or a mouse U6 promoter. Specific examples of suitable promoters (e.g., for expressing a guide RNA) include an RNA polymerase III promoter, such as a human U6 promoter, a rat U6 polymerase III promoter, or a mouse U6 polymerase III promoter.

Optionally, the promoter can be a bidirectional promoter driving expression of one gene (e.g., a gene encoding a chimeric DNA-targeting protein) and a second gene (e.g., a gene encoding a guide RNA or a chimeric adaptor protein) in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express two genes simultaneously allows for the generation of compact expression cassettes to facilitate delivery.

One or more of the nucleic acids can be together in a multicistronic expression construct. For example, a nucleic acid encoding a chimeric Cas protein and a nucleic acid encoding a chimeric adaptor protein can be together in a bicistronic expression construct. See, e.g., FIGS. 1A and 1B. Multicistronic expression vectors simultaneously express two or more separate proteins from the same mRNA (i.e., a transcript produced from the same promoter). Suitable strategies for multicistronic expression of proteins include, for example, the use of a 2A peptide and the use of an internal ribosome entry site (IRES). For example, such constructs can comprise: (1) nucleic acids encoding one or more chimeric Cas proteins and one or more chimeric adaptor proteins; (2) nucleic acids encoding two or more chimeric adaptor proteins; (3) nucleic acids encoding two or more chimeric Cas proteins; (4) nucleic acids encoding two or more guide RNAs or two or more guide RNA arrays; (5) nucleic acids encoding one or more chimeric Cas proteins and one or more guide RNAs or guide RNA arrays; (6) nucleic acids encoding one or more chimeric adaptor proteins and one or more guide RNAs or guide RNA arrays; or (7) nucleic acids encoding one or more chimeric Cas proteins, one or more chimeric adaptor proteins, and one or more guide RNAs or guide RNA arrays. As one example, such multicistronic vectors can use one or more internal ribosome entry sites (TRES) to allow for initiation of translation from an internal region of an mRNA. As another example, such multicistronic vectors can use one or more 2A peptides. These peptides are small “self-cleaving” peptides, generally having a length of 18-22 amino acids and produce equimolar levels of multiple genes from the same mRNA. Ribosomes skip the synthesis of a glycyl-prolyl peptide bond at the C-terminus of a 2A peptide, leading to the “cleavage” between a 2A peptide and its immediate downstream peptide. See, e.g., Kim et al. (2011) *PLoS One* 6(4): e18556, herein incorporated by reference in its entirety for all purposes. The “cleavage” occurs between the glycine and proline residues found on the C-terminus, meaning the upstream cistron will have a few additional residues added to the end, while the downstream cistron will start with the proline. As a result, the “cleaved-off” downstream peptide has proline at its N-terminus. 2A-mediated cleavage is a universal phenomenon in all eukaryotic cells. 2A peptides have been identified from picornaviruses, insect viruses and type C rotaviruses. See, e.g., Szymczak et al. (2005) *Expert Opin Biol Ther* 5:627-638, herein incorporated by reference in its entirety for all purposes. Examples of 2A peptides that can be used include Thoseaasigna virus 2A (T2A); porcine teschovirus-1 2A (P2A); equine rhinitis A virus (ERAV) 2A (E2A); and FMDV 2A (F2A). Exemplary T2A, P2A, E2A, and F2A sequences include the following: T2A (EGRGSLLTCGDVEENPGP; SEQ ID NO: 20); P2A (ATNFSLLKQAGDVEENPGP; SEQ ID NO: 21); E2A (QCTNYALLKLAGDVESNPGP; SEQ ID NO: 22); and F2A (VKQTLNFDLLKLAGDVESNPGP; SEQ ID NO: 23). GSG residues can be added to the 5' end of any of these peptides to improve cleavage efficiency.

Any of the nucleic acids or expression cassettes can also comprise a polyadenylation signal or transcription terminator upstream of a coding sequence. For example, a chimeric Cas protein expression cassette, a chimeric adaptor protein expression cassette, a SAM expression cassette, a guide RNA expression cassette, or a recombinase expression cassette can comprise a polyadenylation signal or transcription terminator upstream of the coding sequence(s) in the expression cassette. The polyadenylation signal or transcription terminator can be flanked by recombinase recognition sites recognized by a site-specific recombinase. Optionally, the recombinase recognition sites also flank a selection cassette comprising, for example, the coding sequence for a drug resistance protein. Optionally the recombinase recognition sites do not flank a selection cassette. The polyadenylation signal or transcription terminator prevents transcription and expression of the protein or RNA encoded by the coding sequence (e.g., chimeric Cas protein, chimeric adaptor protein, guide RNA, or recombinase). However, upon exposure to the site-specific recombinase, the polyadenylation signal or transcription terminator will be excised, and the protein or RNA can be expressed.

Such a configuration for an expression cassette (e.g., a chimeric Cas protein expression cassette or a SAM expression cassette) can enable tissue-specific expression or developmental-stage-specific expression in non-human animals comprising the expression cassette if the polyadenylation signal or transcription terminator is excised in a tissue-specific or developmental-stage-specific manner. For example, in the case of the chimeric Cas protein, this may reduce toxicity due to prolonged expression of the chimeric Cas protein in a cell or non-human animal or expression of the chimeric Cas protein at undesired developmental stages or in undesired cell or tissue types within an a non-human animal. See, e.g., Parikh et al. (2015) *PLoS One* 10(1): e0116484, herein incorporated by reference in its entirety for all purposes. Excision of the polyadenylation signal or transcription terminator in a tissue-specific or developmental-stage-specific manner can be achieved if a non-human animal comprising the expression cassette further comprises a coding sequence for the site-specific recombinase operably linked to a tissue-specific or developmental-stage-specific promoter. The polyadenylation signal or transcription terminator will then be excised only in those tissues or at those developmental stages, enabling tissue-specific expression or developmental-stage-specific expression. In one example, a chimeric Cas protein, a chimeric adaptor protein, a chimeric Cas protein and a chimeric adaptor protein, or a guide RNA can be expressed in a liver-specific manner. Examples of such promoters that have been used to develop such "recombinase deleter" strains of non-human animals are disclosed elsewhere herein.

Any transcription terminator or polyadenylation signal can be used. A "transcription terminator" as used herein refers to a DNA sequence that causes termination of transcription. In eukaryotes, transcription terminators are recognized by protein factors, and termination is followed by polyadenylation, a process of adding a poly(A) tail to the mRNA transcripts in presence of the poly(A) polymerase. The mammalian poly(A) signal typically consists of a core sequence, about 45 nucleotides long, that may be flanked by diverse auxiliary sequences that serve to enhance cleavage and polyadenylation efficiency. The core sequence consists of a highly conserved upstream element (AATAAA or AAUAAA) in the mRNA, referred to as a poly A recognition motif or poly A recognition sequence), recognized by cleavage and polyadenylation-specificity factor (CPSF), and a poorly defined downstream region (rich in Us or Gs and Us), bound by cleavage stimulation factor (CstF). Examples of transcription terminators that can be used include, for example, the human growth hormone (HGH) polyadenylation signal, the simian virus 40 (SV40) late polyadenylation signal, the rabbit beta-globin polyadenylation signal, the bovine growth hormone (BGH) polyadenylation signal, the phosphoglycerate kinase (PGK) polyadenylation signal, an AOX1 transcription termination sequence, a CYC1 transcription termination sequence, or any transcription termination sequence known to be suitable for regulating gene expression in eukaryotic cells.

Site-specific recombinases include enzymes that can facilitate recombination between recombinase recognition sites, where the two recombination sites are physically separated within a single nucleic acid or on separate nucleic acids. Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

The expression cassettes disclosed herein can comprise other components as well. Such expression cassettes (e.g., chimeric Cas protein expression cassette, chimeric adaptor protein expression cassette, SAM expression cassette, guide RNA expression cassette, or recombinase expression cassette) can further comprise a 3' splicing sequence at the 5' end of the expression cassette and/or a second polyadenylation signal following the coding sequence (e.g., encoding the chimeric Cas protein, the chimeric adaptor protein, the guide RNA, or the recombinase). The term 3' splicing sequence refers to a nucleic acid sequence at a 3' intron/exon boundary that can be recognized and bound by splicing machinery. An expression cassette can further comprise a selection cassette comprising, for example, the coding sequence for a drug resistance protein. Examples of suitable selection markers include neomycin phosphotransferase ($neo^r$), hygromycin B phosphotransferase (hygr), puromycin-N-acetyltransferase ($puro^r$), blasticidin S deaminase (bsrr), xanthine/guanine phosphoribosyl transferase (gpt), and herpes simplex virus thymidine kinase (HSV-k). Optionally, the selection cassette can be flanked by recombinase recognition sites for a site-specific recombinase. If the expression cassette also comprises recombinase recognition sites flanking a polyadenylation signal upstream of the coding sequence as described above, the selection cassette can be flanked by the same recombinase recognition sites or can be flanked by a different set of recombinase recognition sites recognized by a different recombinase.

An expression cassette can also comprise a nucleic acid encoding one or more reporter proteins, such as a fluorescent protein (e.g., a green fluorescent protein). Any suitable reporter protein can be used. For example, a fluorescent reporter protein as defined elsewhere herein can be used, or a non-fluorescent reporter protein can be used. Examples of fluorescent reporter proteins are provided elsewhere herein. Non-fluorescent reporter proteins include, for example, reporter proteins that can be used in histochemical or bioluminescent assays, such as beta-galactosidase, luciferase (e.g., *Renilla* luciferase, firefly luciferase, and NanoLuc luciferase), and beta-glucuronidase. An expression cassette can include a reporter protein that can be detected in a flow cytometry assay (e.g., a fluorescent reporter protein such as a green fluorescent protein) and/or a reporter protein that can be detected in a histochemical assay (e.g., beta-galactosidase protein). One example of such a histochemical assay is visualization of in situ beta-galactosidase expression histochemically through hydrolysis of X-Gal (5-bromo-4-chloro-3-indoyl-b-D-galactopyranoside), which yields a blue precipitate, or using fluorogenic substrates such as beta-methyl umbelliferyl galactoside (MUG) and fluorescein digalactoside (FDG).

The expression cassettes described herein can be in any form. For example, an expression cassette can be in a vector or plasmid, such as a viral vector. The expression cassette can be operably linked to a promoter in an expression construct capable of directing expression of a protein or RNA (e.g., upon removal of an upstream polyadenylation signal). Alternatively, an expression cassette can be in a targeting vector. For example, the targeting vector can comprise homology arms flanking the expression cassette, wherein the homology arms are suitable for directing recombination with a desired target genomic locus to facilitate genomic integration and/or replacement of endogenous sequence.

The expression cassettes described herein can be in vitro, they can be within a cell (e.g., an embryonic stem cell) ex vivo (e.g., genomically integrated or extrachromosomal), or they can be in an organism (e.g., a non-human animal) in vivo (e.g., genomically integrated or extrachromosomal). If ex vivo, the expression cassette(s) can be in any type of cell from any organism, such as a totipotent cell such as an embryonic stem cell (e.g., a mouse or a rat embryonic stem cell) or an induced pluripotent stem cell (e.g., a human induced pluripotent stem cell). If in vivo, the expression cassette(s) can be in any type of organism (e.g., a non-human animal as described further elsewhere herein).

A specific example of a nucleic acid encoding a catalytically inactive Cas protein can comprise, consist essentially of, or consist of a nucleic acid encoding an amino acid sequence at least 85%, 90%, 91%, 92%, 93%, 94%, 95%, 96%, 97%, 98%, 99%, or 100% identical to the dCas9 protein sequence set forth in SEQ ID NO: 2. Optionally, the nucleic acid can comprise, consist essentially of, or consist of a nucleic acid encoding an amino acid sequence at least 85%, 90%, 91%, 92%, 93%, 94%, 95%, 96%, 97%, 98%, 99%, or 100% identical to the sequence set forth in SEQ ID NO: 24 (optionally wherein the sequence encodes a protein at least 85%, 90%, 91%, 92%, 93%, 94%, 95%, 96%, 97%, 98%, 99%, or 100% identical to the dCas9 protein sequence set forth in SEQ ID NO: 2).

A specific example of a nucleic acid encoding a chimeric Cas protein can comprise, consist essentially of, or consist of a nucleic acid encoding an amino acid sequence at least 85%, 90%, 91%, 92%, 93%, 94%, 95%, 96%, 97%, 98%, 99%, or 100% identical to the chimeric Cas protein sequence set forth in SEQ ID NO: 1. Optionally, the nucleic acid can comprise, consist essentially of, or consist of a nucleic acid encoding an amino acid sequence at least 85%, 90%, 91%, 92%, 93%, 94%, 95%, 96%, 97%, 98%, 99%, or 100% identical to the sequence set forth in SEQ ID NO: 25 (optionally wherein the sequence encodes a protein at least 85%, 90%, 91%, 92%, 93%, 94%, 95%, 96%, 97%, 98%, 99%, or 100% identical to the chimeric Cas protein sequence set forth in SEQ ID NO: 1).

A specific example of a nucleic acid encoding an adaptor can comprise, consist essentially of, or consist of a nucleic acid encoding an amino acid sequence at least 85%, 90%, 91%, 92%, 93%, 94%, 95%, 96%, 97%, 98%, 99%, or 100% identical to MCP sequence set forth in SEQ ID NO: 7. Optionally, the nucleic acid can comprise, consist essentially of, or consist of a nucleic acid encoding an amino acid sequence at least 85%, 90%, 91%, 92%, 93%, 94%, 95%, 96%, 97%, 98%, 99%, or 100% identical to the sequence set forth in SEQ ID NO: 26 (optionally wherein the sequence encodes a protein at least 85%, 90%, 91%, 92%, 93%, 94%, 95%, 96%, 97%, 98%, 99%, or 100% identical to the MCP sequence set forth in SEQ ID NO: 7).

A specific example of a nucleic acid encoding a chimeric adaptor protein can comprise, consist essentially of, or consist of a nucleic acid encoding an amino acid sequence at least 85%, 90%, 91%, 92%, 93%, 94%, 95%, 96%, 97%, 98%, 99%, or 100% identical to the chimeric adaptor protein sequence set forth in SEQ ID NO: 6. Optionally, the nucleic acid can comprise, consist essentially of, or consist of a nucleic acid encoding an amino acid sequence at least 85%, 90%, 91%, 92%, 93%, 94%, 95%, 96%, 97%, 98%, 99%, or 100% identical to the sequence set forth in SEQ ID NO: 27 (optionally wherein the sequence encodes a protein at least 85%, 90%, 91%, 92%, 93%, 94%, 95%, 96%, 97%, 98%, 99%, or 100% identical to the chimeric adaptor protein sequence set forth in SEQ ID NO: 6).

Specific examples of nucleic acids encoding transcriptional activation domains can comprise, consist essentially of, or consist of a nucleic acid encoding an amino acid sequence at least 85%, 90%, 91%, 92%, 93%, 94%, 95%, 96%, 97%, 98%, 99%, or 100% identical to the VP64, p65, or HSF1 sequences set forth in SEQ ID NO: 3, 8, or 9, respectively. Optionally, the nucleic acid can comprise, consist essentially of, or consist of a nucleic acid encoding an amino acid sequence at least 85%, 90%, 91%, 92%, 93%, 94%, 95%, 96%, 97%, 98%, 99%, or 100% identical to the sequence set forth in SEQ ID NO: 28, 29, or 30, respectively (optionally wherein the sequence encodes a protein at least 85%, 90%, 91%, 92%, 93%, 94%, 95%, 96%, 97%, 98%, 99%, or 100% identical to the VP64, p65, or HSF1 sequences set forth in SEQ ID NO: 3, 8, or 9, respectively).

One exemplary synergistic activation mediator (SAM) expression cassette comprises from 5' to 3': (a) a 3' splicing sequence; (b) a first recombinase recognition site (e.g., loxP site); (c) a coding sequence for a drug resistance gene (e.g., neomycin phosphotransferase ($neo^r$) coding sequence); (d) a polyadenylation signal; (e) a second recombinase recognition site (e.g., loxP site); (f) a chimeric Cas protein coding sequence (e.g., dCas9-NLS-VP64 fusion protein); (g) a 2A protein coding sequence (e.g., a T2A coding sequence); and (e) a chimeric adaptor protein coding sequence (e.g., MCP-NLS-p65-HSF1). See, e.g., FIG. 1A and SEQ ID NO: 31 (coding sequence set forth in SEQ ID NO: 64 and encoding protein set forth in SEQ ID NO: 44).

One exemplary generic guide RNA array expression cassette comprises from 5' to 3': (a) a 3' splicing sequence; (b) a first recombinase recognition site (e.g., rox site); (c) a coding sequence for a drug resistance gene (e.g., puromycin-N-acetyltransferase ($puro^r$) coding sequence); (d) a polyadenylation signal; (e) a second recombinase recognition site (e.g., rox site); (f) a guide RNA comprising one or more guide RNA genes (e.g., a first U6 promoter followed by a first guide RNA coding sequence, a second U6 promoter followed by a second guide RNA coding sequence, and a third U6 promoter followed by a third guide RNA coding sequence). See, e.g., FIG. 5 and SEQ ID NO: 32. The region of SEQ ID NO: 32 comprising the promoters and guide RNA coding sequences is set forth in SEQ ID NO: 65. The recombinase recognition sites in the guide RNA array expression cassette can be the same or different from the recombinase recognition sites in the SAM expression cassette (e.g., can be recognized by the same recombinase or a different recombinase). Such an exemplary guide RNA array expression cassette encoding guide RNAs targeting mouse Ttr is set forth in SEQ ID NO: 33. The region of SEQ ID NO: 33 comprising the promoters and guide RNA coding sequences is set forth in SEQ ID NO: 66.

Another exemplary generic guide RNA array expression cassette comprises one or more guide RNA genes (e.g., a first U6 promoter followed by a first guide RNA coding sequence, a second U6 promoter followed by a second guide RNA coding sequence, and a third U6 promoter followed by a third guide RNA coding sequence). Such an exemplary generic guide RNA array expression cassette is set forth iN SEQ ID NO: 66. Examples of such guide RNA array expression cassettes for specific genes are set forth, e.g., in SEQ ID NOS: 33, 66, 67, 71, 84, 85, and 98.

F. Genomic Loci for Integration

The nucleic acids and expression cassettes described herein can be genomically integrated at a target genomic locus in a cell or a non-human animal. Any target genomic locus capable of expressing a gene can be used.

An example of a target genomic locus into which the nucleic acids or cassettes described herein can be stably integrated is a safe harbor locus in the genome of the non-human animal. Interactions between integrated exogenous DNA and a host genome can limit the reliability and safety of integration and can lead to overt phenotypic effects that are not due to the targeted genetic modification but are instead due to unintended effects of the integration on surrounding endogenous genes. For example, randomly inserted transgenes can be subject to position effects and silencing, making their expression unreliable and unpredictable. Likewise, integration of exogenous DNA into a chromosomal locus can affect surrounding endogenous genes and chromatin, thereby altering cell behavior and phenotypes. Safe harbor loci include chromosomal loci where transgenes or other exogenous nucleic acid inserts can be stably and reliably expressed in all tissues of interest without overtly altering cell behavior or phenotype (i.e., without any deleterious effects on the host cell). See, e.g., Sadelain et al. (2012) *Nat. Rev. Cancer* 12:51-58, herein incorporated by reference in its entirety for all purposes. For example, the safe harbor locus can be one in which expression of the inserted gene sequence is not perturbed by any read-through expression from neighboring genes. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

Figure 2:
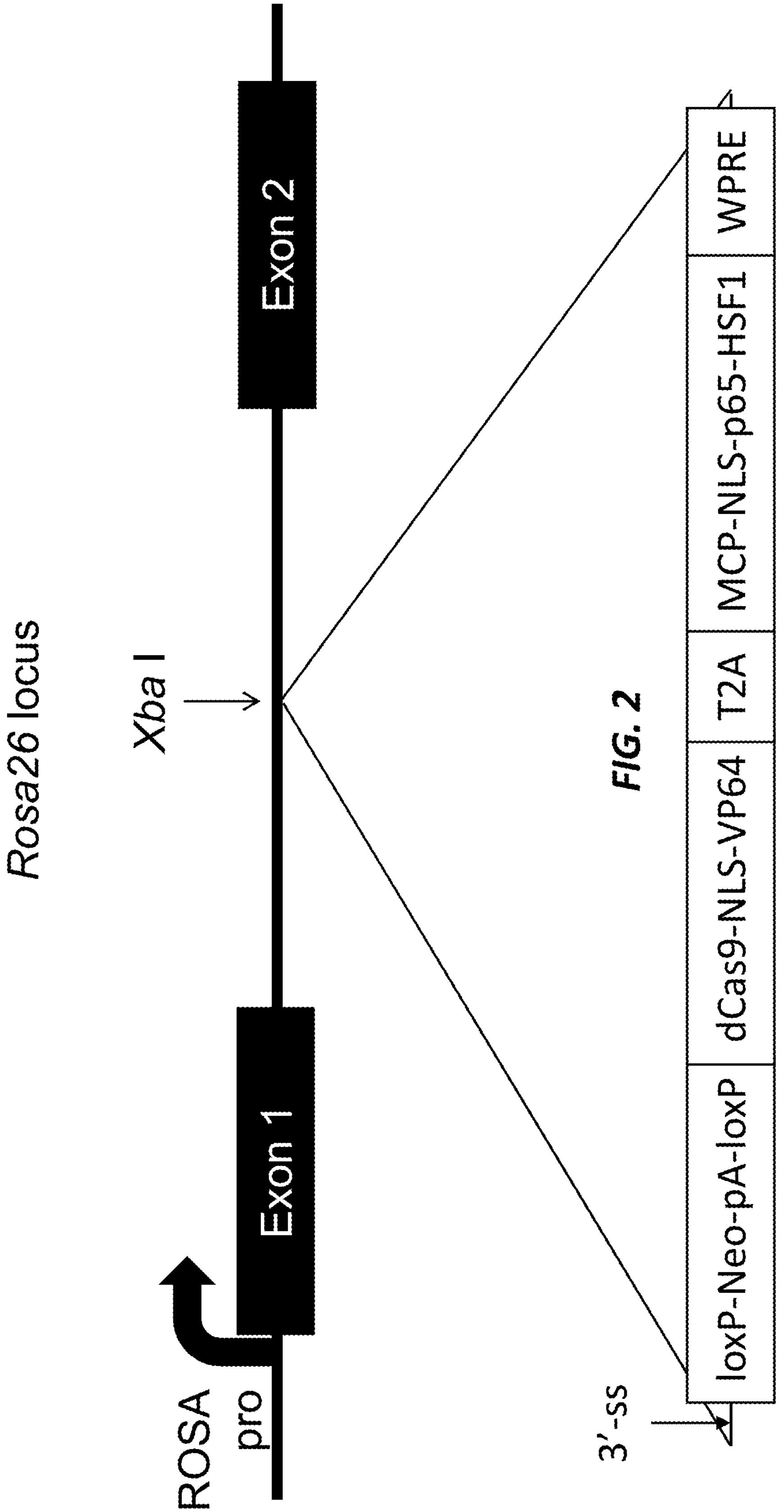
FIG. 2 shows a general schematic for targeting the dCas9 SAM allele from FIG. 1A into the first intron of the Rosa26 locus.

For example, the Rosa26 locus and its equivalent in humans offer an open chromatin configuration in all tissues and is ubiquitously expressed during embryonic development and in adults. See, e.g., Zambrowicz et al. (1997) *Proc. Natl. Acad. Sci. USA* 94:3789-3794, herein incorporated by reference in its entirety for all purposes. In addition, the Rosa26 locus can be targeted with high efficiency, and disruption of the Rosa26 gene produces no overt phenotype. Other examples of safe harbor loci include CCR5, HPRT, AAVS1, and albumin. See, e.g., U.S. Pat. Nos. 7,888,121; 7,972,854; 7,914,796; 7,951,925; 8,110,379; 8,409,861; 8,586,526; and US Patent Publication Nos. 2003/0232410; 2005/0208489; 2005/0026157; 2006/0063231; 2008/0159996; 2010/00218264; 2012/0017290; 2011/0265198; 2013/0137104; 2013/0122591; 2013/0177983; 2013/0177960; and 2013/0122591, each of which is herein incorporated by reference in its entirety for all purposes. Biallelic targeting of safe harbor loci such as the Rosa26 locus has no negative consequences, so different genes or reporters can be targeted to the two Rosa26 alleles. In one example, an expression cassette is integrated into an intron of the Rosa26 locus, such as the first intron of the Rosa26 locus. See, e.g., FIG. 2.

Expression cassettes integrated into a target genomic locus can be operably linked to an endogenous promoter at the target genomic locus or can be operably linked to an exogenous promoter that is heterologous to the target genomic locus. In one example, a chimeric Cas protein expression cassette, chimeric adaptor protein expression cassette, or synergistic activation mediator (SAM) expression cassette is integrated into a target genomic locus (e.g., the Rosa26 locus) and is operably linked to the endogenous promoter at the target genomic locus (e.g., the Rosa26 promoter). In another example, a guide RNA expression cassette is integrated into a target genomic locus (e.g., the Rosa26 locus) and is operably linked to one or more heterologous promoters (e.g., U6 promoter(s), such as a different U6 promoter upstream of each guide RNA coding sequence).

G. Non-Human Animal Genomes, Non-Human Animal Cells, and Non-Human Animals

Non-human animal genomes, non-human animal cells, and non-human animals comprising the nucleic acids or expression cassettes described herein are also provided. The genomes, cells, or non-human animals can be male or female. The nucleic acids or expression cassettes can be stably integrated into the genome (i.e., into a chromosome) of the cell or non-human animal or it can be located outside of a chromosome (e.g., extrachromosomally replicating DNA). The nucleic acids or expression cassettes can be randomly integrated into the genome of the non-human animal (i.e., transgenic), or it can be integrated into a predetermined region (e.g., a safe harbor locus) of the genome of the non-human animal (i.e., knock in). The target genomic locus at which a nucleic acid or expression cassette is stably integrated can be heterozygous for the nucleic acid or expression cassette or homozygous for the nucleic acid or expression cassette. A diploid organism has two alleles at each genetic locus. Each pair of alleles represents the genotype of a specific genetic locus. Genotypes are described as homozygous if there are two identical alleles at a particular locus and as heterozygous if the two alleles differ. A non-human animal comprising a stably integrated nucleic acid or expression cassette described herein can comprise the nucleic acid or expression cassette in its germline.

For example, a non-human animal genome, non-human animal cell, or non-human animal can comprise a chimeric Cas protein expression cassette, a chimeric adaptor protein expression cassette, or a synergistic activation mediator (SAM) expression cassette (comprising both a chimeric Cas protein coding sequence and a chimeric adaptor protein sequence) as disclosed herein. In one example, the genome, cell or non-human animal comprises a SAM expression cassette comprising both a chimeric Cas protein coding sequence and a chimeric adaptor protein coding sequence. In one example, the SAM expression cassette (or chimeric Cas protein expression cassette or chimeric adaptor protein expression cassette) is stably integrated into the genome. The stably integrated SAM expression cassette (or chimeric Cas protein expression cassette or chimeric adaptor protein expression cassette) can be randomly integrated into the genome of the non-human animal (i.e., transgenic), or it can be integrated into a predetermined region of the genome of the non-human animal (i.e., knock in). In one example, the SAM expression cassette (or chimeric Cas protein expression cassette or chimeric adaptor protein expression cassette) is stably integrated into a predetermined region of the genome, such as a safe harbor locus (e.g., Rosa26). The target genomic locus at which the SAM expression cassette (or chimeric Cas protein expression cassette or chimeric adaptor protein expression cassette) is stably integrated can be heterozygous or homozygous for the SAM expression cassette (or chimeric Cas protein expression cassette or chimeric adaptor protein expression cassette).

Optionally, the genome, cell, or non-human animal described above can further comprise a guide RNA expression cassette (e.g., guide RNA array expression cassette). The guide RNA expression cassette can be stably integrated into the genome (i.e., into a chromosome) of the cell or non-human animal or it can be located outside of a chromosome (e.g., extrachromosomally replicating DNA or introduced into the cell or non-human animal via AAV, LNP, or any other means disclosed herein). The guide RNA expression cassette can be randomly integrated into the genome of the non-human animal (i.e., transgenic), or it can be integrated into a predetermined region (e.g., a safe harbor locus) of the genome of the non-human animal (i.e., knock in). The target genomic locus at which the guide RNA expression cassette is stably integrated can be heterozygous or homozygous for the guide RNA expression cassette. In one example, a genome, cell, or non-human animal comprises both a SAM expression cassette (or chimeric Cas protein expression cassette or chimeric adaptor protein expression cassette) and a guide RNA expression cassette. In one example, both cassettes are genomically integrated. The guide RNA expression cassette can be integrated at a different target genomic locus from the SAM expression cassette (or chimeric Cas protein expression cassette or chimeric adaptor protein expression cassette), or it can be genomically integrated at the same target locus (e.g., a Rosa26 locus, such as integrated in the first intron of the Rosa26 locus). For example, the genome, cell, or non-human animal can be heterozygous for each of a SAM expression cassette (or chimeric Cas protein expression cassette or chimeric adaptor protein expression cassette) and the guide RNA expression cassette, with one allele of the target genomic locus (e.g., Rosa26) comprising the SAM expression cassette (or chimeric Cas protein expression cassette or chimeric adaptor protein expression cassette), and a second allele of the target genomic locus comprising the guide RNA expression cassette expression cassette.

Optionally, any of the genomes, cells, or non-human animals described above can further comprise a recombinase expression cassette. The recombinase expression cassette can be stably integrated into the genome (i.e., into a chromosome) of the cell or non-human animal or it can be located outside of a chromosome (e.g., extrachromosomally replicating DNA or introduced into the cell or non-human animal via AAV, LNP, HDD, or any other means disclosed herein). The recombinase expression cassette can be randomly integrated into the genome of the non-human animal (i.e., transgenic), or it can be integrated into a predetermined region (e.g., a safe harbor locus) of the genome of the non-human animal (i.e., knock in). The target genomic locus at which the recombinase expression cassette is stably integrated can be heterozygous or homozygous for the recombinase expression cassette. The recombinase expression cassette can be integrated at a different target genomic locus from any of the other expression cassettes disclosed herein, or it can be genomically integrated at the same target locus (e.g., a Rosa26 locus, such as integrated in the first intron of the Rosa26 locus).

The genomes or cells provided herein can be, for example, eukaryotic genomes or cells, which include, for example, fungal cells (e.g., yeast), plant cells, animal cells, mammalian cells, non-human mammalian cells, and human cells. The term "animal" includes mammals, fishes, and birds. A mammalian genome or cell can be, for example, a non-human mammalian cell, a human cell, a rodent cell, a rat cell, a mouse cell, or a hamster cell. Other non-human mammals include, for example, non-human primates, monkeys, apes, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

Examples of human pluripotent cells include human ES cells, human adult stem cells, developmentally restricted human progenitor cells, and human induced pluripotent stem (iPS) cells, such as primed human iPS cells and naïve human iPS cells. Induced pluripotent stem cells include pluripotent stem cells that can be derived directly from a differentiated adult cell. Human iPS cells can be generated by introducing specific sets of reprogramming factors into a cell which can include, for example, Oct3/4, Sox family transcription factors (e.g., Sox1, Sox2, Sox3, Sox15), Myc family transcription factors (e.g., c-Myc, 1-Myc, n-Myc), Kruppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, e.g., Takahashi and Yamanaka (2006) *Cell* 126:663-676, herein incorporated by reference in its entirety for all purposes. Primed human ES cells and primed human iPS cells include cells that express characteristics similar to those of post-implantation epiblast cells and are committed for lineage specification and differentiation. Naïve human ES cells and naïve human iPS cells include cells that express characteristics similar to those of ES cells of the inner cell mass of a pre-implantation embryo and are not committed for lineage specification. See, e.g., Nichols and Smith (2009) *Cell Stem Cell* 4:487-492, herein incorporated by reference in its entirety for all purposes.

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, kidney cells, hematopoietic cells, endothelial cells, epithelial cells, fibroblasts, mesenchymal cells, keratinocytes, blood cells, melanocytes, monocytes, mononuclear cells, monocytic precursors, B cells, erythroid-megakaryocytic cells, eosinophils, macrophages, T cells, islet beta cells, exocrine cells, pancreatic progenitors, endocrine progenitors, adipocytes, preadipocytes, neurons, glial cells, neural stem cells, neurons, hepatoblasts, hepatocytes, cardiomyocytes, skeletal myoblasts, smooth muscle cells, ductal cells, acinar cells, alpha cells, beta cells, delta cells, PP cells, cholangiocytes, white or brown adipocytes, or ocular cells (e.g., trabecular meshwork cells, retinal pigment epithelial cells, retinal microvascular endothelial cells, retinal pericyte cells, conjunctival epithelial cells, conjunctival fibroblasts, iris pigment epithelial cells, keratocytes, lens epithelial cells, non-pigment ciliary epithelial cells, ocular choroid fibroblasts, photoreceptor cells, ganglion cells, bipolar cells, horizontal cells, or amacrine cells).

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK 293 cells or 293T cells), and mouse embryonic fibroblast cells (e.g., 3T3 cells). Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a nucleic acid or expression cassette as described herein can be made by the methods described elsewhere herein. The term “animal” includes mammals, fishes, and birds. Mammals include, for example, humans, non-human primates, monkeys, apes, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term “non-human animal” excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 12952, 12954, 12955, 12959/SvEvH, 12956 (129/SvEvTac), 12957, 12958, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. In some cases, suitable rats can be from an inbred rat strain. See, e.g., US 2014/0235933, herein incorporated by reference in its entirety for all purposes.

III. Methods of Increasing Transcription/Expression of Target Genes and for Assessing CRISPR/Cas Activity In Vivo Various methods are provided for using the synergistic activation mediator systems and the cells and non-human animals described herein for activating transcription of one or more target genes in vivo or for assessing CRISPR/Cas delivery to and for assessing CRISPR/Cas activity in tissues and organs of a live animal. Such methods make use of non-human animals comprising expression cassettes as described elsewhere herein.

A. Methods of Increasing Expression of a Target Gene or Testing Ability of CRISPR/Cas to Activate Transcription of a Target Gene In Vivo or Ex Vivo Various methods are provided for increasing/activating expression/transcription of a target gene or assessing the ability of a CRISPR/Cas synergistic activation mediator (SAM) system described herein to increase/activate expression/transcription of a target gene in vivo using the non-human animals described herein. Such non-human animals, for example, can comprise a SAM expression cassette (comprising a chimeric Cas protein coding sequence and a chimeric adaptor protein coding sequence) or can comprise a chimeric Cas protein expression cassette or a chimeric adaptor protein expression cassette. Such methods can comprise introducing into the non-human animal one or more guide RNAs each comprising one or more adaptor-binding elements to which a chimeric adaptor protein disclosed herein can specifically bind. The one or more guide RNAs can form complexes with the chimeric Cas protein and chimeric adaptor protein and guide them to target sequences within one or more target genes, thereby increasing expression of the one or more target genes. Such methods can further comprise assessing expression or transcription of the one or more target genes.

Optionally, two or more guide RNAs can be introduced, each designed to target a different guide RNA target sequence within a target gene. For example, 2 or more, 3 or more, 4 or more, or 5 or more guide RNAs can be designed to target a single target gene. Alternatively or additionally, two or more guide RNAs can be introduced, each designed to target different guide RNA target sequences in two or more different target genes (i.e., multiplexing).

Optionally, in methods in which the chimeric Cas protein expression cassette, chimeric adaptor protein expression cassette, or synergistic activation mediator expression cassette (comprising chimeric Cas protein coding sequence and chimeric adaptor protein coding sequence) comprises a polyadenylation signal or transcription terminator upstream of the coding sequence(s), and the polyadenylation signal or transcription terminator is flanked by recombinase recognition sites recognized by a site-specific recombinase, the method can further comprise introducing a recombinase into the non-human animal. The recombinase can excise the polyadenylation signal or transcription terminator, thereby permitting expression of the downstream coding sequence(s).

In some methods in which the non-human animal already comprises a guide RNA expression cassette as described elsewhere herein, the method may simply comprise introducing a recombinase into the non-human animal, wherein the recombinase excises the upstream polyadenylation signal or transcription terminator, thereby allowing expression of the chimeric Cas protein and/or chimeric adaptor protein, whereby expression/transcription of the target gene is increased/activated.

Optionally, in methods in which the non-human animal comprises a chimeric Cas protein expression cassette but not a chimeric adaptor protein expression cassette, the chimeric adaptor protein can be introduced into the non-human animal. Likewise, in methods in which the non-human animal comprises a chimeric adaptor protein expression cassette but not a chimeric Cas protein expression cassette, the chimeric Cas protein expression cassette can be introduced into the non-human animal.

The various methods provided above for assessing CRISPR/Cas activity in vivo can also be used to assess CRISPR/Cas activity ex vivo using cells comprising a Cas expression cassette as described elsewhere herein.

Guide RNAs and, optionally, recombinases can be introduced into the cell or non-human animal in any form (DNA or RNA for guide RNA; DNA, RNA, or protein for recombinases) via any delivery method (e.g., AAV, LNP, or HDD) and any route of administration as disclosed elsewhere herein. The guide RNAs or recombinases can be introduced in a tissue-specific manner in some methods. In particular methods, the delivery is via AAV-mediated delivery. For example, AAV8 can be used if the liver is being targeted. Similarly, if a the non-human animal or cell comprises a chimeric Cas protein expression cassette but not a chimeric adaptor protein expression cassette, the chimeric adaptor protein can be introduced into the cell or non-human animal in any form (DNA, RNA, or protein) via any delivery method (e.g., AAV, LNP, or HDD) and any route of administration as disclosed elsewhere herein. Alternatively, if the non-human animal or cell comprises a chimeric adaptor protein expression cassette but not a chimeric Cas protein expression cassette, the chimeric Cas protein can be introduced into the cell or non-human animal in any form (DNA, RNA, or protein) via any delivery method (e.g., AAV, LNP, or HDD) and any route of administration as disclosed elsewhere herein.

Methods for assessing increased transcription or expression of a target genomic locus are provided elsewhere herein and are well known. Assessment can be in any cell type, any tissue type, or any organ type as disclosed elsewhere herein. In some methods, expression of the target gene in liver cells is assessed, e.g., by assessing serum levels of a secreted protein expressed by the target genomic locus in liver cells. If the target gene encodes a protein with a particular enzymatic activity, assessment can comprise measuring expression of the target gene and/or activity of the protein encoded by the target gene. Alternatively or additionally, assessment can comprise assessing expression in one or more cells isolated from the non-human animal. Assessment can comprise isolating a target organ or tissue from the non-human animal and assessing expression of the target gene in the target organ or tissue. Assessment can also comprise assessing expression of the target gene in two or more different cell types within the target organ or tissue. Similarly, assessment can comprise isolating a non-target organ or tissue (e.g., two or more non-target organs or tissues) from the non-human animal and assessing expression of the target gene in the non-target organ or tissue.

In some methods, the target gene can be a disease-associated gene as described elsewhere herein. For example, the target gene can be a gene associated with a protein aggregation disease or disorder. As a specific example, the target gene can be a gene (e.g., Ttr) associated with a protein aggregation disease or disorder, and the method can comprise increasing expression of that target gene to model the protein aggregation disease or disorder. In some specific methods, the target gene can be Ttr. Optionally, the Ttr gene can comprise a pathogenic mutation (e.g., a mutation causing amyloidosis) or a combination of pathogenic mutations. Examples of such mutations are provided, e.g., in WO 2018/007871, herein incorporated by reference in its entirety for all purposes.

In other methods, the target gene can be one involved in pathways related to a disease or condition, such as hypercholesterolemia or atherosclerosis. In some specific methods, the target gene can be Pcsk9 or Ldlr. In other methods, the target gene can be a gene that when overexpressed can model such diseases or conditions. For example, the target gene can be Pcsk9, and the method can comprise increasing expression of Pcsk9 to model hypercholesterolemia.

B. Methods of Optimizing Ability of CRISPR/Cas to Increase Expression of a Target Gene In Vivo or Ex Vivo Various methods are provided for optimizing delivery of CRISPR/Cas to a cell or non-human animal or optimizing CRISPR/Cas transcriptional activation activity in vivo. Such methods can comprise, for example: (a) performing the method of testing the ability of CRISPR/Cas to modify a target genomic locus as described above a first time in a first non-human animal or first cell; (b) changing a variable and performing the method a second time in a second non-human animal (i.e., of the same species) or a second cell with the changed variable; and (c) comparing expression/transcription of the target gene in step (a) with the expression/transcription of the target gene in step (b), and selecting the method resulting in the highest expression/transcription of the target gene.

Alternatively or additionally, the method resulting in the highest efficacy, highest consistency, or highest specificity can be chosen. Higher efficacy refers to higher levels of expression/transcription of the target gene (e.g., a higher percentage of cells is targeted within a particular target cell type, within a particular target tissue, or within a particular target organ). Higher consistency refers to more consistent increases in expression/transcription of the target gene among different types of targeted cells, tissues, or organs if more than one type of cell, tissue, or organ is being targeted (e.g., increased expression/transcription of a greater number of cell types within a target organ). If a particular organ is being targeted, higher consistency can also refer to more consistent increases in expression/transcription throughout all locations within the organ. Higher specificity can refer to higher specificity with respect to the target gene or genes being targeted, higher specificity with respect to the cell type targeted, higher specificity with respect to the tissue type targeted, or higher specificity with respect to the organ targeted. For example, increased target specificity refers to fewer off-target effects on other genes (e.g., a lower percentage of targeted cells having increased transcription at unintended, off-target genomic loci (e.g., neighboring genomic loci) instead of or in addition to modification of the target genomic locus). Likewise, increased cell type, tissue, or organ type specificity refers to fewer effects (i.e., increased expression/transcription) in off-target cell types, tissue types, or organ types if a particular cell type, tissue type, or organ type is being targeted (e.g., when a particular organ is targeted (e.g., the liver), there are fewer effects (i.e., increased expression/transcription) in cells in organs or tissues that are not intended targets).

The variable that is changed can be any parameter. As one example, the changed variable can be the packaging or the delivery method by which the guide RNA (or optionally recombinase or other component) is introduced into the cell or non-human animal. Examples of delivery methods, such as LNP, HDD, and AAV, are disclosed elsewhere herein. For example, the changed variable can be the AAV serotype. As another example, the changed variable can be the route of administration for introduction of the guide RNA (or optionally recombinase or other component) into the cell or non-human animal. Examples of routes of administration, such as intravenous, intravitreal, intraparenchymal, and nasal instillation, are disclosed elsewhere herein.

As another example, the changed variable can be the concentration or amount of the guide RNA (or optionally recombinase or other component) introduced. As another example, the changed variable can be the number of times or frequency with which the guide RNA (or optionally recombinase or other component) are introduced. As another example, the changed variable can be the form in which the guide RNA (or optionally recombinase or other component) are introduced. For example, the guide RNA can be introduced in the form of DNA or in the form of RNA. Similarly, the guide RNA (or optionally recombinase or other component) can comprise various combinations of modifications for stability, to reduce off-target effects, to facilitate delivery, and so forth. As another example, the changed variable can be the sequence of the guide RNA that is introduced (e.g., introducing a different guide RNA with a different sequence).

C. Introducing Guide RNAs and Other Components into Cells and Non-Human Animals

The methods disclosed herein comprise introducing into a cell or non-human animal one or more guide RNAs, guide RNA arrays, recombinases, or other components as described elsewhere herein. "Introducing" includes presenting to the cell or non-human animal the nucleic acid or protein in such a manner that the nucleic acid or protein gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a first guide RNA can be introduced into a cell or non-human animal before introduction of a second guide RNA. In addition, two or more of the components can be introduced into the cell or non-human animal by the same delivery method or different delivery methods. Similarly, two or more of the components can be introduced into a non-human animal by the same route of administration or different routes of administration.

A guide RNA can be introduced into the cell in the form of an RNA (e.g., in vitro transcribed RNA) or in the form of a DNA encoding the guide RNA. Likewise, protein components such as recombinases can be introduced into the cell in the form of DNA, RNA, or protein. When introduced in the form of a DNA, the DNA encoding a guide RNA can be operably linked to a promoter active in the cell. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Nucleic acids encoding guide RNAs or recombinases (or other components) can be operably linked to a promoter in an expression construct. Expression constructs include any nucleic acid constructs capable of directing expression of a gene or other nucleic acid sequence of interest and which can transfer such a nucleic acid sequence of interest to a target cell. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a guide RNA in one direction and another component in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a guide RNA and another component simultaneously allows for the generation of compact expression cassettes to facilitate delivery.

Guide RNAs or nucleic acids encoding guide RNAs (or other components) can be provided in compositions comprising a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a nucleic acid or protein into a cell or non-human animal. Methods for introducing nucleic acids into various cell types are known in the art and include, for example, stable transfection methods, transient transfection methods, and virus-mediated methods.

Transfection protocols as well as protocols for introducing nucleic acid sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediated AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a guide RNA in the form of RNA. Delivery through such methods results in transient presence of the guide RNA, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1 and WO 2017/173054 A1, each of which is herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) *Cell Reports* 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. See, e.g., Finn et al. (2018) *Cell Reports* 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis(oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino)propoxy)carbonyl)oxy)hexadecanoyl)oxy)propane-1,3-diyl (9Z,9'Z,12Z,12'Z)-bis(octadeca-9,12-dienoate). Another example of a suitable lipid is Lipid D, which is 3-(((3-(dimethylamino)propoxy)carbonyl)oxy)-13-(octanoyloxy)tridecyl 3-octylundecanoate.

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-distearoylglycerol (PEG-DSPE), PEG-dilaurylglycamide, PEG-dimyristylglycamide, PEG-dipalmitoylglycamide, and PEG-distearoylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. See, e.g., Finn et al. (2018) *Cell Reports* 22:1-9, herein incorporated by reference in its entirety for all purposes. Another example of a suitable lipid is Lipid B, which is ((5-((dimethylamino)methyl)-1,3-phenylene)bis(oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino)propoxy)carbonyl)oxy)hexadecanoyl)oxy)propane-1,3-diyl(9Z,9'Z,12Z,12'Z)-bis(octadeca-9,12-dienoate). Another example of a suitable lipid is Lipid D, which is 3-(((3-(dimethylamino)propoxy)carbonyl)oxy)-13-(octanoyloxy)tridecyl 3-octylundecanoate. Other suitable lipids include heptatriaconta-6,9,28,31-tetraen-19-yl 4-(dimethylamino)butanoate (also known as Dlin-MC3-DMA (MC3))).

Another specific example of a suitable LNP has a nitrogen-to-phosphate (N/P) ratio of 6 and contains biodegradable cationic lipid, cholesterol, DSPC, and PEG2k-DMG in a 50:38:9:3 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate.

The mode of delivery can be selected to decrease immunogenicity. For example, a different components may be delivered by different modes (e.g., bi-modal delivery). These different modes may confer different pharmacodynamics or pharmacokinetic properties on the subject delivered molecule. For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of components in a more transient manner, for example as RNA, can ensure that the Cas/gRNA complex is only present and active for a short period of time and can reduce immunogenicity. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Local modes of administration include, for example, intrathecal, intracerebroventricular, intraparenchymal (e.g., localized intraparenchymal delivery to the striatum (e.g., into the caudate or into the putamen), cerebral cortex, precentral gyrus, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Nasal instillation and intravitreal injection are other specific examples. Compositions comprising the guide RNAs (or nucleic acids encoding the guide RNAs) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the exogenous donor nucleic acids or guide RNAs (or nucleic acids encoding the guide RNAs) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

D. Measuring CRISPR/Cas Activity In Vivo and Assessing Expression of a Target Gene The methods disclosed herein can further comprise assessing expression of the target gene. The methods for measuring expression or activity will depend on the target gene being modified.

For example, if the target gene comprises a gene encoding an RNA or protein, the method of assessing expression can comprise measuring expression or activity of the encoded RNA and/or protein. For example, if the encoded protein is a protein released into the serum, serum levels of the encoded protein can be measured. Assays for measuring levels and activity of RNA and proteins are well known.

Assessing expression of the target gene in a non-human animal can be in any cell type from any tissue or organ. For example, expression of the target gene can be assessed in multiple cell types from the same tissue or organ or in cells from multiple locations within the tissue or organ. This can provide information about which cell types within a target tissue or organ are being targeted or which sections of a tissue or organ are being reached by the CRISPR/Cas and modified. As another example, expression of the target gene can be assessed in multiple types of tissue or in multiple organs. In methods in which a particular tissue or organ is being targeted, this can provide information about how effectively that tissue or organ is being targeted and whether there are off-target effects in other tissues or organs.

IV. Methods of Making Non-Human Animals Comprising a Cas Expression Cassette and/or a Recombinase Expression Cassette Various methods are provided for making a non-human animal comprising one or more or all of a synergistic activation mediator (SAM) expression cassette (comprising a chimeric Cas protein coding sequence and a chimeric adaptor protein expression coding sequence), a guide RNA expression cassette, and a recombinase expression as disclosed elsewhere herein. Likewise, various methods are provided for making a non-human animal comprising one or more or all of a chimeric Cas protein expression cassette, a chimeric adaptor protein expression cassette, a guide RNA expression cassette, and a recombinase expression as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted locus (e.g., a safe harbor locus such as Rosa26) or through use of a randomly integrating transgene. See, e.g., WO 2014/093622 and WO 2013/176772, each of which is herein incorporated by reference in its entirety for all purposes. Methods of targeting a construct to the Rosa26 locus are described, for example, in US 2012/0017290, US 2011/0265198, and US 2013/0236946, each of which is herein incorporated by reference in its entirety for all purposes.

For example, the method of producing a non-human animal comprising one or more or all of the expression cassettes disclosed elsewhere herein can comprise: (1) modifying the genome of a pluripotent cell to comprise one or more or all of the expression cassettes; (2) identifying or selecting the genetically modified pluripotent cell comprising the one or more or all of the expression cassettes; (3) introducing the genetically modified pluripotent cell into a non-human animal host embryo; and (4) implanting and gestating the host embryo in a surrogate mother. For example, the method of producing a non-human animal comprising one or more or all of the expression cassettes disclosed elsewhere herein can comprise: (1) modifying the genome of a pluripotent cell to comprise one or more or all of the expression cassettes; (2) identifying or selecting the genetically modified pluripotent cell comprising the one or more or all of the expression cassettes; (3) introducing the genetically modified pluripotent cell into a non-human animal host embryo; and (4) gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising one or more or all of the expression cassettes.

The methods can further comprise identifying a cell or animal having a modified target genomic locus. Various methods can be used to identify cells and animals having a targeted genetic modification.

The step of modifying the genome can, for example, utilize exogenous donor nucleic acids (e.g., targeting vectors) to modify a target genomic locus to comprise one or more or all of the expression cassettes disclosed elsewhere herein. As one example, the targeting vector can comprise a 5' homology arm targeting a 5' target sequence at the target genomic locus and a 3' homology arm targeting a 3' target sequence at the target genomic locus. Exogenous donor nucleic acids can also comprise nucleic acid inserts including segments of DNA to be integrated in the target genomic locus. Integration of a nucleic acid insert in the target genomic locus can result in addition of a nucleic acid sequence of interest in the target genomic locus, deletion of a nucleic acid sequence of interest in the target genomic locus, or replacement of a nucleic acid sequence of interest in the target genomic locus (i.e., deletion and insertion). The homology arms can flank an insert nucleic acid comprising one or more or all of the expression cassettes disclosed elsewhere herein to generate the targeted genomic locus.

The exogenous donor nucleic acids can be for non-homologous-end-joining-mediated insertion or homologous recombination. Exogenous donor nucleic acids can comprise deoxyribonucleic acid (DNA) or ribonucleic acid (RNA), they can be single-stranded or double-stranded, and they can be in linear or circular form. For example, a repair template can be a single-stranded oligodeoxynucleotide (ssODN).

Exogenous donor nucleic acids can also comprise a heterologous sequence that is not present at an untargeted endogenous target genomic locus. For example, an exogenous donor nucleic acids can comprise a selection cassette, such as a selection cassette flanked by recombinase recognition sites.

Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the target genomic locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. In some targeting vectors, the intended mutation in the target genomic locus is included in an insert nucleic acid flanked by the homology arms.

In cells other than one-cell stage embryos, the exogenous donor nucleic acid can be a "large targeting vector" or "LTVEC," which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). LTVECs can be of any length and are typically at least 10 kb in length. The sum total of the 5' homology arm and the 3' homology arm in an LTVEC is typically at least 10 kb.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, by (a) introducing into the cell one or more targeting vectors comprising an insert nucleic acid flanked by 5' and 3' homology arms corresponding to 5' and 3' target sites, wherein the insert nucleic acid comprises one or more or all of the expression cassettes disclosed herein; and (b) identifying at least one cell comprising in its genome the insert nucleic acid integrated at the target genomic locus. Alternatively, the modified pluripotent cell can be generated by (a) introducing into the cell: (i) a nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises one or more or all of the expression cassettes; and (c) identifying at least one cell comprising a modification (e.g., integration of the insert nucleic acid) at the target genomic locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the one or more or all of the expression cassettes using the methods described above for modifying pluripotent cells; (2) selecting the genetically modified embryo; and (3) implanting and gestating the genetically modified embryo into a surrogate mother. Alternatively, the method of producing the non-human animals described elsewhere herein can comprise: (1) modifying the genome of a one-cell stage embryo to comprise the one or more or all of the expression cassettes using the methods described above for modifying pluripotent cells; (2) selecting the genetically modified embryo; and (3) gestating the genetically modified embryo into a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the one or more or all of the expression cassettes. It is recognized that depending on the method used to generate the F0 animal, the number of cells within the F0 animal that have the one or more or all of the expression cassettes will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for one or more or all of the expression cassettes disclosed herein or can be homozygous for one or more or all of the expression cassettes disclosed herein.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 3

Description of Sequences.

| SEQ ID NO | Type | Description |
|---|---|---|
| 1 | Protein | dCas9-VP64 chimeric Cas protein |
| 2 | Protein | dCas9 protein |
| 3 | Protein | VP64 transcriptional activation domain |
| 4 | Protein | Linker v1 |
| 5 | Protein | Linker v2 |
| 6 | Protein | MCP-p65-HSF1 chimeric adaptor protein |
| 7 | Protein | MS2 coat protein (MCP) |
| 8 | Protein | p65 transcriptional activation domain |
| 9 | Protein | HSF1 transcriptional activation domain |
| 10 | RNA | crRNA tail |
| 11 | RNA | tracrRNA |
| 12 | RNA | gRNA scaffold v1 |
| 13 | RNA | gRNA scaffold v2 |
| 14 | RNA | gRNA scaffold v3 |
| 15 | RNA | gRNA scaffold v4 |
| 16 | RNA | MS2-binding loop |
| 17 | DNA | Guide RNA target sequence plus PAM v1 |
| 18 | DNA | Guide RNA target sequence plus PAM v2 |
| 19 | DNA | Guide RNA target sequence plus PAM v3 |
| 20 | Protein | T2A |
| 21 | Protein | P2A |
| 22 | Protein | E2A |
| 23 | Protein | F2A |
| 24 | DNA | Nucleic acid encoding dCas9 protein |
| 25 | DNA | Nucleic acid encoding dCas9-VP64 chimeric Cas protein |
| 26 | DNA | Nucleic acid encoding MCP |
| 27 | DNA | Nucleic acid encoding MCP-p65-HSF1 chimeric adaptor protein |
| 28 | DNA | Nucleic acid encoding VP64 transcriptional activation domain |
| 29 | DNA | Nucleic acid encoding p65 transcriptional activation domain |
| 30 | DNA | Nucleic acid encoding HSF1 transcriptional activation domain |
| 31 | DNA | Synergistic activation mediator (SAM) bicistronic expression cassette (dCas9-VP64-T2A-MCP-p65-HSF1) |
| 32 | DNA | Generic guide RNA array expression cassette |
| 33 | DNA | Ttr guide RNA array expression cassette |

TABLE 3-continued

Description of Sequences.

| SEQ ID NO | Type | Description |
|---|---|---|
| 34 | DNA | Mouse Ttr guide RNA target sequence v1 |
| 35 | DNA | Mouse Ttr guide RNA target sequence v2 |
| 36 | DNA | Mouse Ttr guide RNA target sequence v3 |
| 37 | RNA | Mouse Ttr single guide RNA v1 |
| 38 | RNA | Mouse Ttr single guide RNA v2 |
| 39 | RNA | Mouse Ttr single guide RNA v3 |
| 40 | RNA | gRNA scaffold with MS2 binding loops |
| 41 | RNA | Mouse Ttr guide RNA DNA-targeting segment v1 |
| 42 | RNA | Mouse Ttr guide RNA DNA-targeting segment v2 |
| 43 | RNA | Mouse Ttr guide RNA DNA-targeting segment v3 |
| 44 | Protein | Synergistic activation mediator (SAM) (dCas9-VP64-T2A-MCP-p65-HSF1) |
| 45 | DNA | XBA-TDP fw |
| 46 | DNA | XBA-TDP probe |
| 47 | DNA | XBA-TDP rev |
| 48 | DNA | Neo fw |
| 49 | DNA | Neo probe |
| 50 | DNA | Neo rev |
| 51 | DNA | SAM TD fw |
| 52 | DNA | SAM TD probe |
| 53 | DNA | SAM TD rev |
| 54 | DNA | MS2_T fw |
| 55 | DNA | MS2_T probe |
| 56 | DNA | MS2_T rev |
| 57 | DNA | P65_T fw |
| 58 | DNA | P65_T probe |
| 59 | DNA | P65_T rev |
| 60 | DNA | WPRE_TP fw |
| 61 | DNA | WPRE_TP probe |
| 62 | DNA | WPRE_TP rev |
| 63 | RNA | Generic single gRNA with MS2 binding loops |
| 64 | DNA | Synergistic activation mediator (SAM) coding sequence (dCas9-VP64-T2A-MCP-P65-HSF1) |
| 65 | DNA | Generic guide RNA array promoters and guide RNA coding sequences |
| 66 | DNA | Ttr guide RNA array promoters and guide RNA coding sequences |
| 67 | DNA | pscAAV Ttr array |
| 68 | DNA | pAAV Ttr g1 |
| 69 | DNA | pAAV Ttr g2 |
| 70 | DNA | pAAV Ttr g3 |
| 71 | DNA | pcsAAV Ldlr array |
| 72 | DNA | pAAV Ldlr g1 |
| 73 | DNA | pAAV Ldlr g2 |
| 74 | DNA | pAAV Ldlr g3 |
| 75 | DNA | Mouse Ldlr guide RNA target sequence v1 |
| 76 | DNA | Mouse Ldlr guide RNA target sequence v2 |
| 77 | DNA | Mouse Ldlr guide RNA target sequence v3 |
| 78 | RNA | Mouse Ldlr single guide RNA v1 |
| 79 | RNA | Mouse Ldlr single guide RNA v2 |
| 80 | RNA | Mouse Ldlr single guide RNA v3 |
| 81 | RNA | Mouse Ldlr guide RNA DNA-targeting segment v1 |
| 82 | RNA | Mouse Ldlr guide RNA DNA-targeting segment v2 |
| 83 | RNA | Mouse Ldlr guide RNA DNA-targeting segment v3 |
| 84 | DNA | Ldlr guide RNA array promoters and guide RNA coding sequences |
| 85 | DNA | pcsAAV Pcsk9 array |
| 86 | DNA | pAAV Pcsk9 g1 |
| 87 | DNA | pAAV Pcsk9 g2 |
| 88 | DNA | pAAV Pcsk9 g3 |
| 89 | DNA | Mouse Pcsk9 guide RNA target sequence v1 |
| 90 | DNA | Mouse Pcsk9 guide RNA target sequence v2 |
| 91 | DNA | Mouse Pcsk9 guide RNA target sequence v3 |
| 92 | RNA | Mouse Pcsk9 single guide RNA v1 |
| 93 | RNA | Mouse Pcsk9 single guide RNA v2 |
| 94 | RNA | Mouse Pcsk9 single guide RNA v3 |
| 95 | RNA | Mouse Pcsk9 guide RNA DNA-targeting segment v1 |
| 96 | RNA | Mouse Pcsk9 guide RNA DNA-targeting segment v2 |
| 97 | RNA | Mouse Pcsk9 guide RNA DNA-targeting segment v3 |
| 98 | DNA | Pcsk9 guide RNA array promoters and guide RNA coding sequences |

EXAMPLES

Example 1. Generation of SAM-Ready Mice

To use the dCas9 Synergistic Activation Mediator (SAM) system, typically three components need to be introduced: (1) dCas9 directly fused to a VP64 domain; (2) an MS2 coat protein (MCP) fused to two additional activating transcription factors (heat-shock factor 1 (HSF1) and transcription factor 65 (p65)); and (3) MS2-loop-containing sgRNA. Each component typically needs to be introduced in a separate lentivirus. While the three-component system described allows for some flexibility in cell culture, this setup is less desirable in an animal model. Instead, we chose to introduce the dCas9 SAM components (dCas9-VP64 and MCP-p65-HSF1) as one transcript driven by the endogenous Rosa26 promoter. Initially, expression of the dCas9 SAM system is blocked by the presence of a floxed neomycin stop cassette. Upon introduction of Cre recombinase, the stop cassette is deleted and dCas9 SAM expression is turned on. Guide RNAs or guide RNA arrays (e.g., expressed from a U6 promoter) are then be introduced by integrating them into the other Rosa26 allele or by AAV introduction. By pairing the dCas9 SAM allele with various Cre delivery methods, the timing and tissue specificity of gene modulation are controlled. As shown below, the system can be used to induce expression of genes in vivo and can be used for applications such as disease modeling.

A large targeting vector (LTVEC) comprising homology arms targeting the mouse Rosa26 locus was generated to introduce the dCas9 SAM expression cassette into the first intron of the Rosa26 locus. Generation and use of LTVECs derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

Figure 1B:
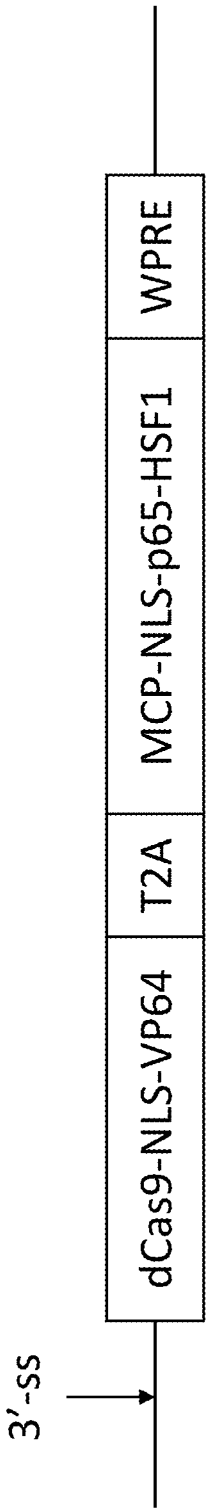
FIG. 1B (not to scale) shows the allele from FIG. 1A with the floxed neomycin resistance gene and polyadenylation signal removed.

The *S. pyogenes* dCas9 coding sequence (CDS) in the expression cassette was codon-optimized for expression in mice. The encoded dCas9 includes the following mutations to render the Cas9 nuclease-inactive: D10A and N863A. The dCas9-NLS-VP64-T2A-MCP-NLS-p65-HSF1-WPRE expression cassette is depicted in FIG. 1A and SEQ ID NO: 31. The synergistic activation mediator (SAM) coding sequence (dCas9-VP64-T2A-MCP-p65-HSF1) is set forth in SEQ ID NO: 64 and encodes the protein set forth in SEQ ID NO: 44. The expression cassette was targeted to the first intron of the Rosa26 locus (see FIG. 2) to take advantage of the strong universal expression of the Rosa26 locus and the ease of targeting the Rosa26 locus. The expression cassette was preceded by a floxed neomycin resistance cassette (neo cassette) with appropriate splicing signals and a strong polyadenylation (polyA) signal. The components of the dCas9 SAM expression cassette from 5' to 3' are shown in Table 4 below.

TABLE 4 dCas9 SAM Expression Cassette Components.

| Component | Nucleotide Region Within SEQ ID NO: 31 |
|---|---|
| First loxP site | 1-34 |
| Sequence encoding neomycin phosphotransferase for resistance to neomycin family antibiotics (e.g. G418) | 125-928 |
| Polyadenylation signal | 937-2190 |
| Second loxP site | 2218-2251 |
| Codon-optimized dCas9 coding sequence | 2306-6457 |
| NLS | 2309-2356 |
| NLS | 6512-6532 |
| VP64 | 6533-6719 |
| T2A with 5' GSG | 6719-6781 |
| MCP | 6782-7171 |
| NLS | 7226-7246 |
| p65 | 7262-7804 |
| HSF1 | 7829-8200 |
| Woodchuck hepatitis virus posttranscriptional regulatory element (WPRE) | 8224-8820 |

To generate the targeted Rosa26 allele, the LTVEC was introduced into F1H4 mouse embryonic stem cells. Following antibiotic selection, colonies were picked, expanded, and screened by TAQMAN®. Modification-of-allele assays were performed to confirm correct targeting. Modification-of-allele (MOA) assays including loss-of-allele (LOA) and gain-of-allele (GOA) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample. The primers and probes used for screening are provided in Table 5.

TABLE 5

Primers and Probes.

| Primer/Probe | Sequence | SEQ ID NO |
|---|---|---|
| XBA-TDP fw | CGTGATCTGCAACTCCAGTCTT | 45 |
| XBA-TDP probe | AGATGGGCGGGAGTCTTCTGGGC | 46 |
| XBA-TDP rev | CACACCAGGTTAGCCTTTAAGCC | 47 |
| Neo fw | GGTGGAGAGGCTATTCGGC | 48 |
| Neo probe | TGGGCACAACAGACAATCGGCTG | 49 |
| Neo rev | GAACACGGCGGCATCAG | 50 |
| SAM TD fw | ACCGGCTGTCCGACTACGAT | 51 |
| SAM TD probe | TGGACCACATCGTGCCTCAGA | 52 |
| SAM TD rev | CGGGCCTTGTCGCTTCTG | 53 |
| MS2_T fw | GGCTCCTTCTAATTTCGCTAATGG | 54 |

TABLE 5-continued

Primers and Probes.

| Primer/Probe | Sequence | SEQ ID NO |
|---|---|---|
| MS2_T probe | TGGCAGAGTGGATCAGCTCCA | 55 |
| MS2_T rev | CTGACGCTGCATGTCACCTT | 56 |
| P65_T fw | AGGGCGTGTCCATGTCTCATAG | 57 |
| P65_T probe | ACAGCCGAACCAATGCTGATGGA | 58 |
| P65_T rev | CCAGCCGGGTAATGGCTTC | 59 |
| WPRE_TP fw | TGTGTTGCCACCTGGATTCTG | 60 |
| WPRE_TP probe | CGCGGGACGTCCTTCTGCTAC | 61 |
| WPRE_TP rev | GGAAGGTCCGCTGGATTGAG | 62 |

F0 mice were generated using the VELOCIMOUSE® method. See, e.g., U.S. Pat. Nos. 7,576,259; 7,659,442; 7,294,754; US 2008/0078000; and Poueymirou et al. (2007) *Nat. Biotechnol.* 25(1):91-99, each of which is herein incorporated by reference in its entirety for all purposes. In the VELOCIMOUSE® method, targeted mouse embryonic stem (ES) cells are injected through laser-assisted injection into pre-morula stage embryos, e.g., eight-cell-stage embryos, which efficiently yields F0 generation mice that are fully ES-cell-derived.

Figure 3B:
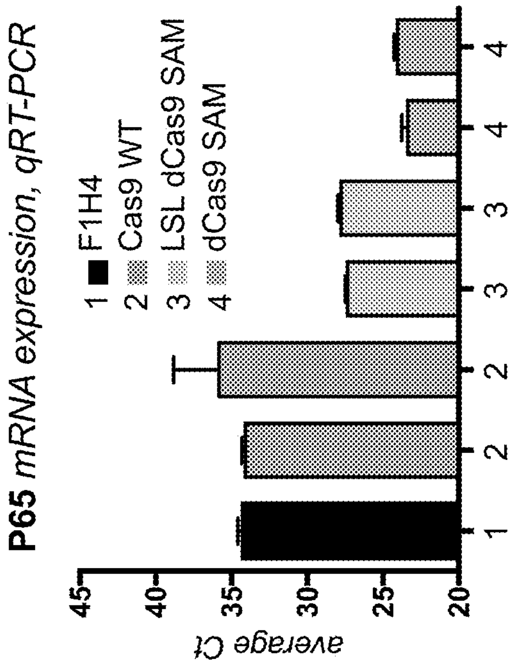
FIG. 3B shows p65 mRNA expression levels in F1H4 wild type (WT) mouse embryonic stem cells (mESCs), Cas9 WT mESCs, LSL dCas9 SAM mESCs (see FIG. 1A), and dCas9 SAM mESCs (see FIG. 1B).
Figure 3A:
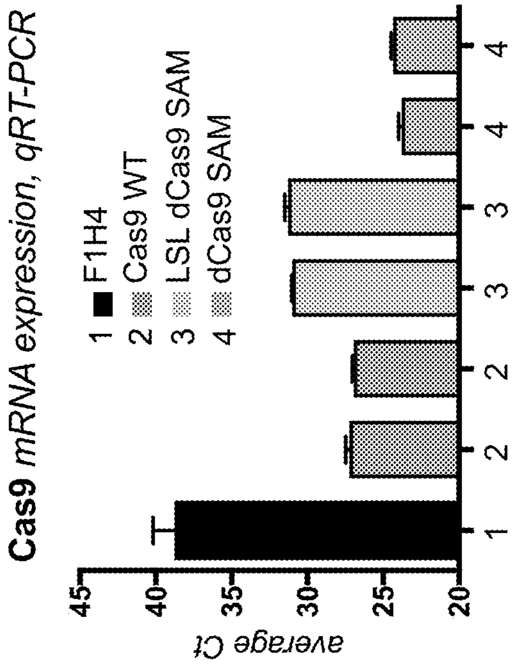
FIG. 3A shows Cas9 mRNA expression levels in F1H4 wild type (WT) mouse embryonic stem cells (mESCs), Cas9 WT mESCs, lox-stop-lox (LSL) dCas9 SAM mESCs (mESCs with the dCas9 SAM allele downstream of a floxed polyadenylation signal as in FIG. 1A), and dCas9 SAM mESCs (mESCs with the dCas9 SAM allele in which the floxed polyadenylation signal has been excised by Cre recombinase as in FIG. 1B).
Figure 4:
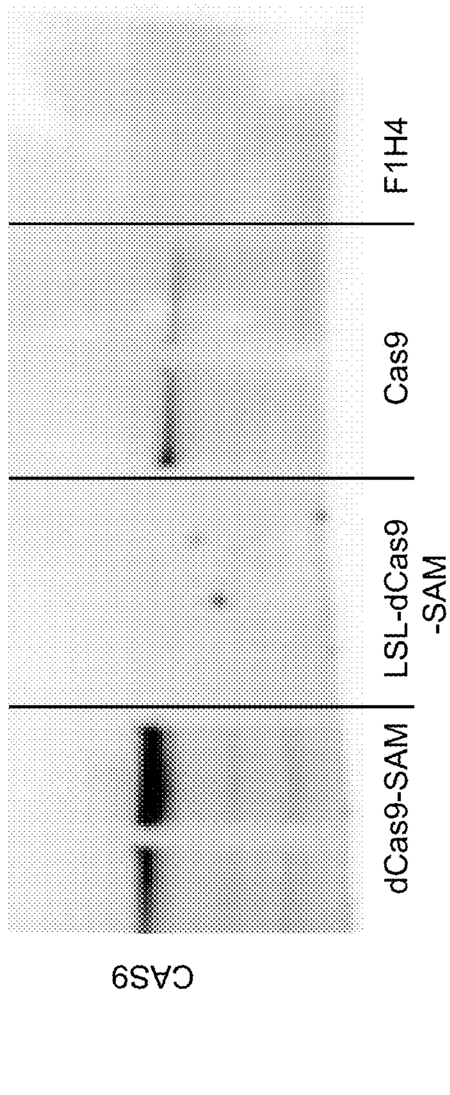
FIG. 4 shows Cas9 protein expression levels in F1H4 wild type (WT) mouse embryonic stem cells (mESCs), Cas9 WT mESCs, LSL dCas9 SAM mESCs (see FIG. 1A), and dCas9 SAM mESCs (see FIG. 1B).

Prior to removal of the floxed neomycin resistance cassette (neo cassette) by the action of Cre recombinase, the neomycin resistance gene is transcribed and translated; however, the dCas9-NLS-VP64 CDS and MCP-NLS-p65-HSF1 CDS are not expressed due to the presence of the strong poly(A) region, which effectively blocks run-through transcription. See FIG. 1A. Upon removal of the neo cassette by the action of Cre recombinase, however, the hybrid mRNA for the dCas9 and MCP fusion proteins is constitutively expressed by the Rosa26 promoter. See FIG. 1B. dCas9 and MCP expression were validated by extracting total RNA from targeted mESCs in which the floxed neomycin resistance cassette (neo cassette) had been removed, followed by reverse transcription to generate cDNA and TAQMAN® qPCR to detect the reverse transcribed cDNA (RT-qPCR). Cas9 and p65 mRNA levels were measured. See FIGS. 3A and 3B, respectively. dCas9 expression was also confirmed by western blot. See FIG. 4. Taken together, the system that was created is capable of expressing consistent levels of dCas9 fusion protein and MCP fusion protein continuously or conditionally (by requiring the removal of a neomycin resistance cassette) in mESCs and mice derived from them.

Example 2. Validation of SAM-Ready Mice with Ttr Guide RNAs

Figure 5:
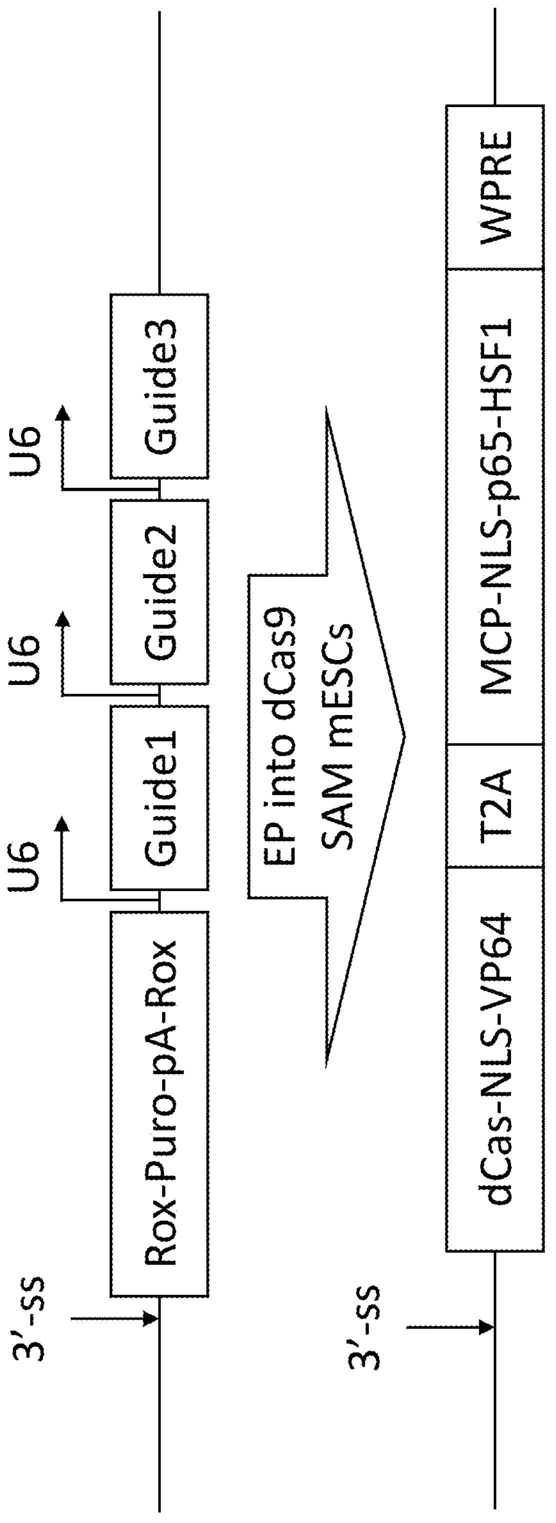
FIG. 5 (not to scale) shows a schematic for introducing a guide RNA array allele into dCas9 SAM mouse embryonic stem cells. The guide RNA array allele comprises from 5' to 3': a 3' splicing sequence; a first rox site; a puromycin resistance gene; a polyadenylation signal; a second rox site; a first U6 promoter; a first guide RNA coding sequence; a second U6 promoter; a second guide RNA coding sequence; a third U6 promoter; and a third guide RNA coding sequence.
Figure 6:
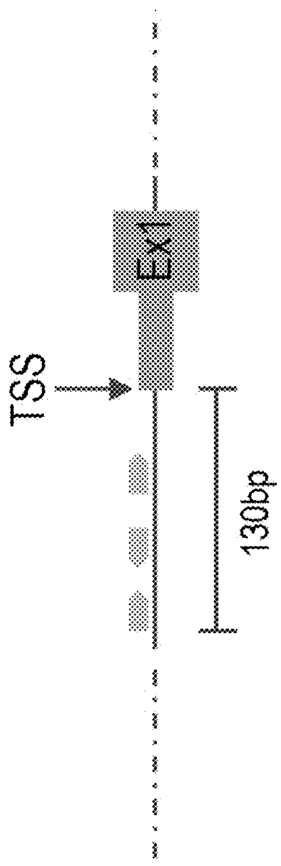
FIG. 6 (not to scale) shows a schematic for designing three guide RNAs that target upstream of the transcription start site of Ttr.
Figure 7:
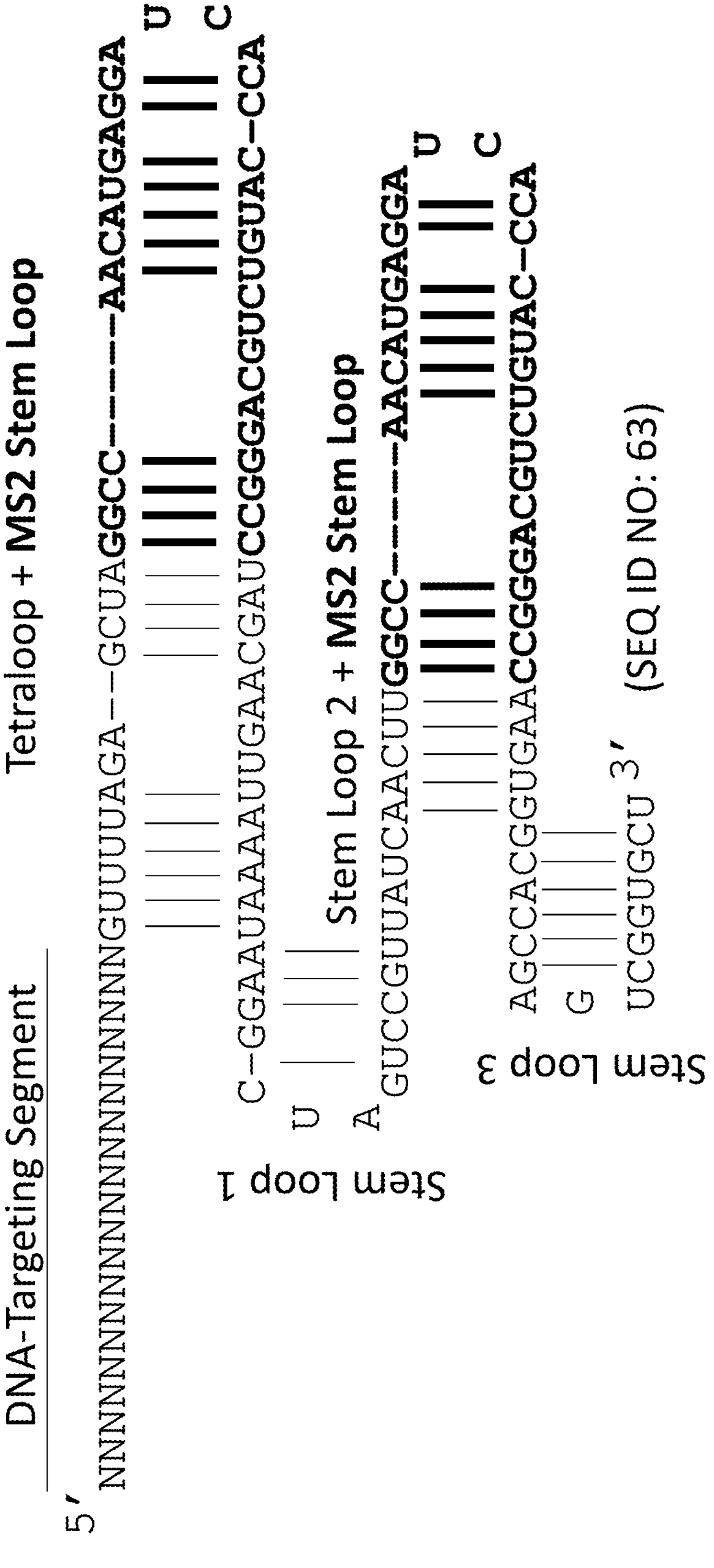
FIG. 7 shows a schematic of a generic single guide RNA (SEQ ID NO: 63) in which the tetraloop and stem loop 2 have been replaced with MS2-binding aptamers to facilitate recruitment of chimeric MS2 coat protein (MCP) fused to transcriptional activation domains.

To validate this system in vivo, heterozygous dCas9 SAM mESCs were targeted with a Ttr guide RNA array targeting vector comprising homology arms targeting the first intron of the mouse Rosa26 locus. The Ttr guide RNA array is depicted in FIG. 5 and in SEQ ID NO: 33. The region including the promoters and guide RNA coding sequences is set forth in SEQ ID NO: 66. The guide RNA target sequences (not including PAM) in the mouse Ttr gene that are targeted by the guide RNAs in the array are set forth in SEQ ID NO: 34 (ACGGTTGCCCTCTTTCCCAA), SEQ ID NO: 35 (ACTGTCAGACTCAAAGGTGC), and SEQ ID NO: 36 (GACAATAAGTAGTCTTACTC), respectively. SEQ ID NO: 34 is located −63 of the Ttr transcription start site, SEQ ID NO: 35 is located −134 of the Ttr transcription start site, and SEQ ID NO: 36 is located −112 of the Ttr transcription start site. The single guide RNAs targeting these guide RNA target sequences are set forth in SEQ ID NOS: 37, 38, and 39, respectively. The homology arms flanked a Ttr guide RNA array comprising three MS2-stem-loop-containing guide RNAs targeting the Ttr locus. The Ttr guide RNA array was integrated at the Rosa26 locus with a roxed puromycin stop cassette. This cassette prevents Rosa26 run-through transcripts from interfering with U6 promoter activity. After the stop cassette, the three sgRNA sequences containing MS2 stem loops were expressed by the U6 promoter in tandem with an extended PolIII termination sequence separating them. The guides were designed to direct the dCas9 SAM components to the 100-200 bp region upstream of the Ttr transcriptional start site (TSS). See FIG. 6. The components of the Ttr guide RNA array expression cassette from 5' to 3' are shown in Table 6 below. A general schematic of the structure of each guide RNA, including the MS2 stem loops, is shown in FIG. 7.

TABLE 6

Ttr Guide RNA Array Expression Cassette Components.

| Component | Nucleotide Region Within SEQ ID NO: 33 |
|---|---|
| First rox site | 1-32 |
| Sequence encoding puromycin-N-acetyltransferase for resistance to puromycin family antibiotics | 111-710 |
| Polyadenylation signal | 797-2338 |
| Second rox site | 2363-2394 |
| First U6 promoter | 2401-2640 |
| First Ttr guide RNA coding sequence | 2642-2798 |
| Second U6 promoter | 2884-3123 |
| Second Ttr guide RNA coding sequence | 3125-3281 |
| Third U6 promoter | 3366-3605 |
| Third Ttr guide RNA coding sequence | 3606-3762 |

Figure 8A:
FIGS. 8A to 8C show Ttr, Dsg2, and B4galt6 mRNA expression levels, respectively, in heterozygous dCas9 SAM mouse embryonic stem cell (mESC) clones targeted with a Ttr guide RNA array. Expression levels were determined by RT-qPCR. The y-axis shows the cycle threshold (ct) values. F1H4 wild type mESCs, LSL dCas9 SAM (see FIG. 1A), and dCas9 SAM (see FIG. 1B) mESC clones were used as controls.
Figure 8C:
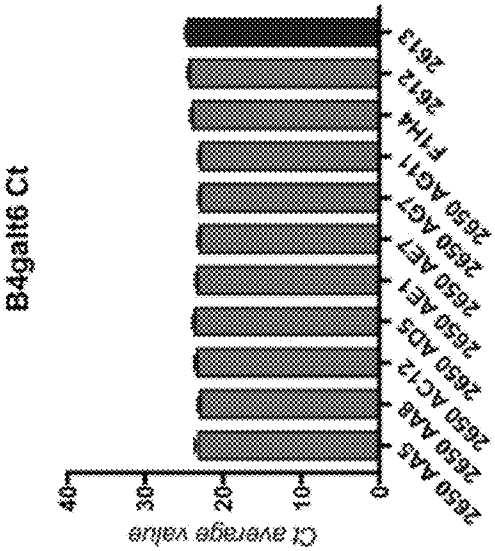
Figure 8B:
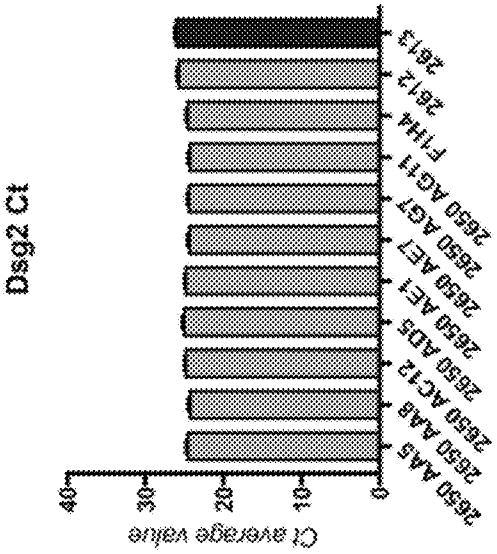
Figure 9A:
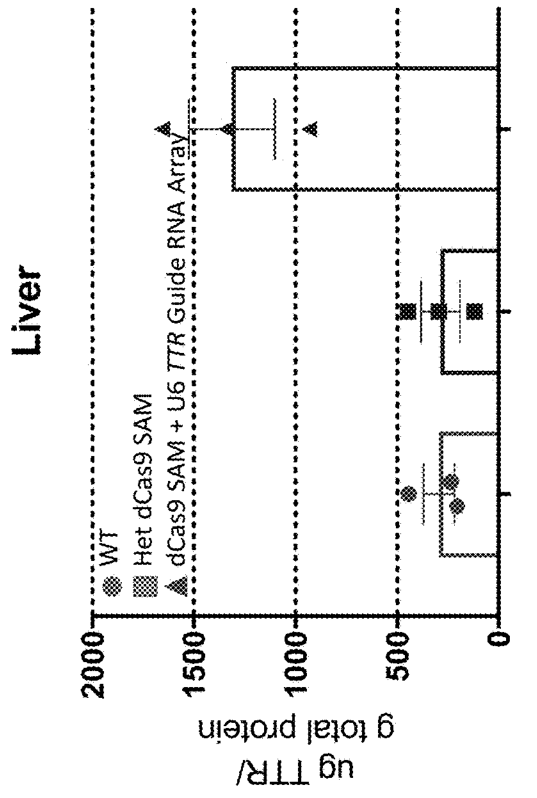
FIGS. 9A-9L show TTR protein expression in various tissues isolated from wild-type mice, heterozygous dCas9 SAM mice, and heterozygous dCas9 SAM mice that are also heterozygous for a Ttr guide RNA array.
Figure 9B:
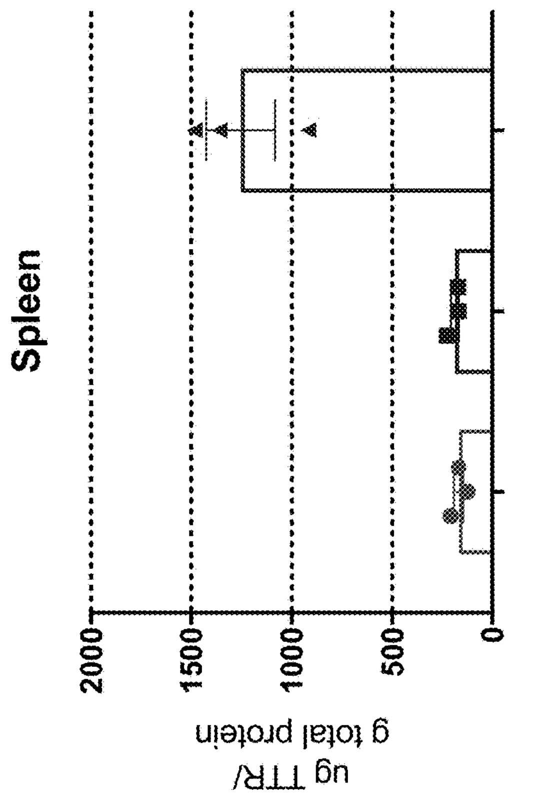
Figure 9C:
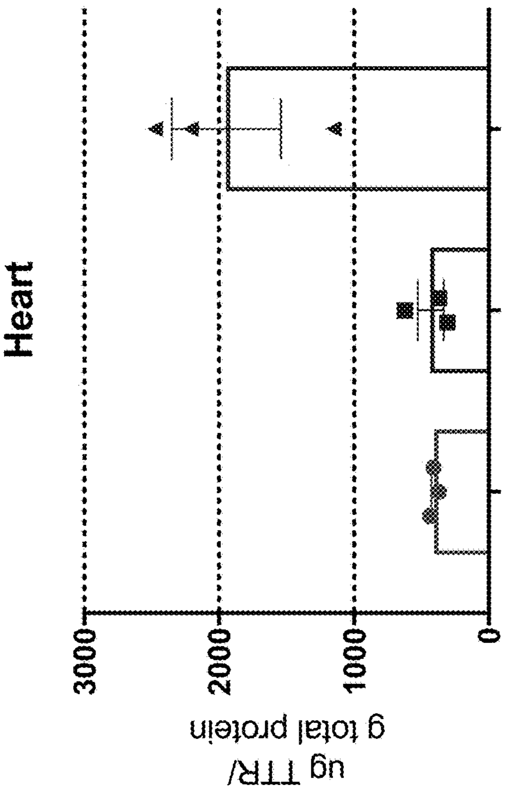
Figure 9D:
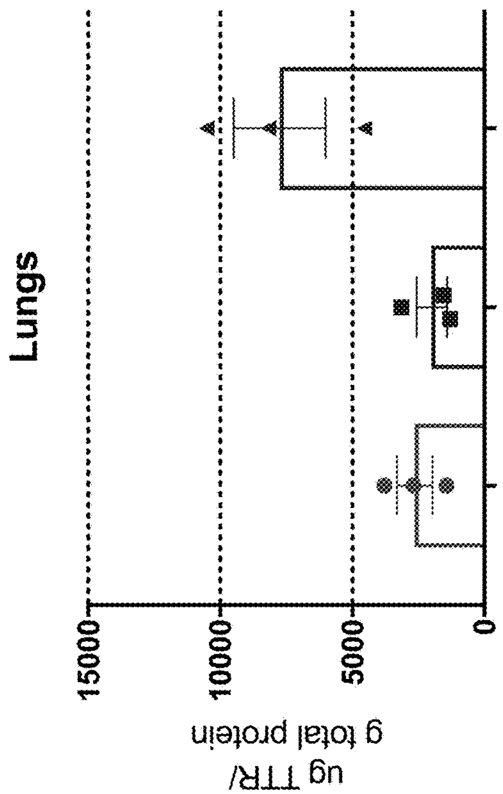
Figure 9E:
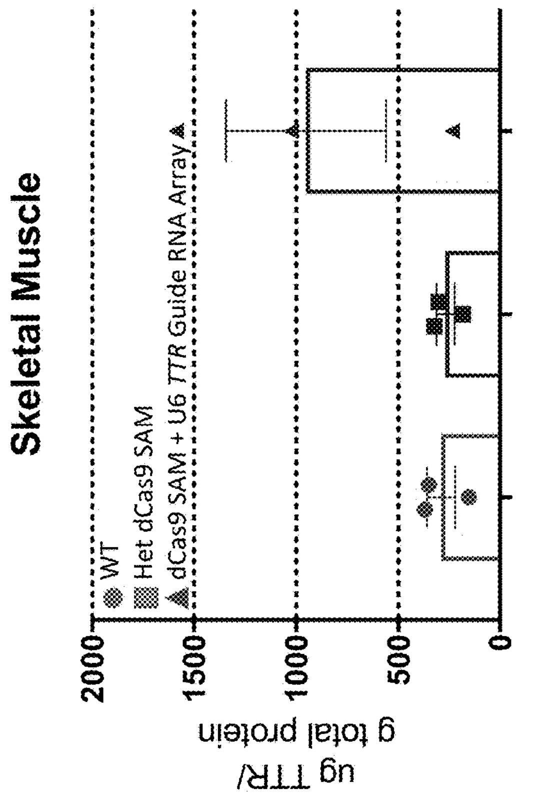
Figure 9F:
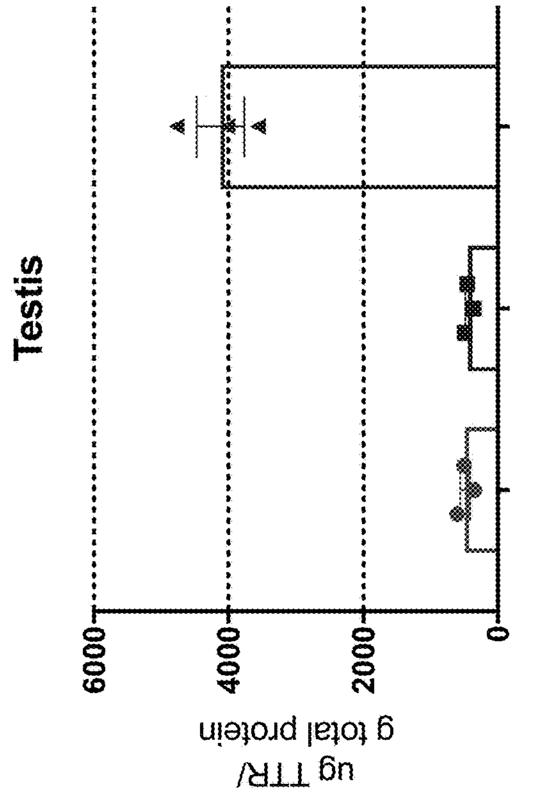
Figure 9G:
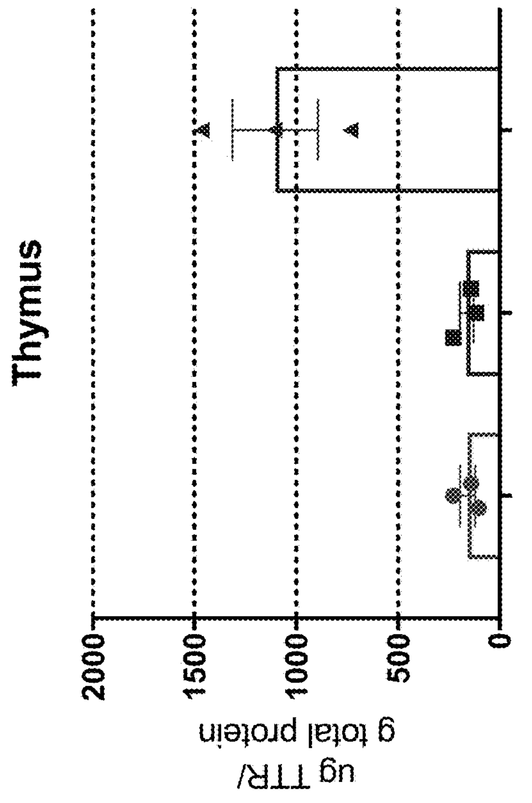
Figure 9H:
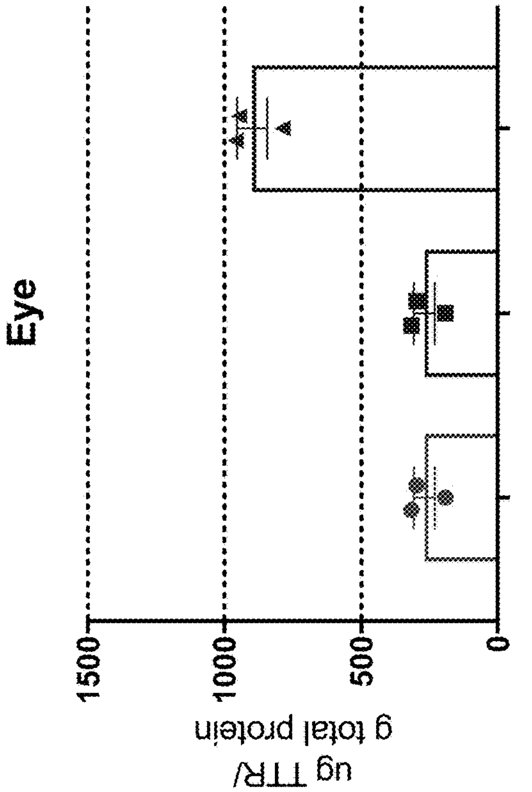
Figure 9I:
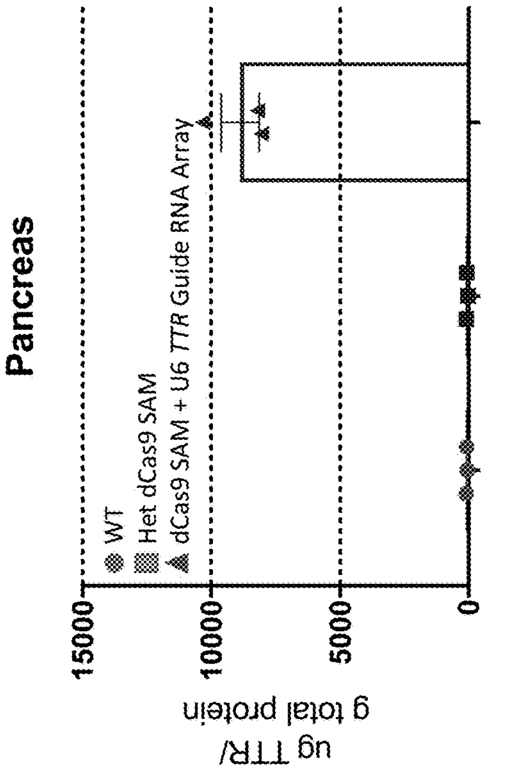
Figure 9J:
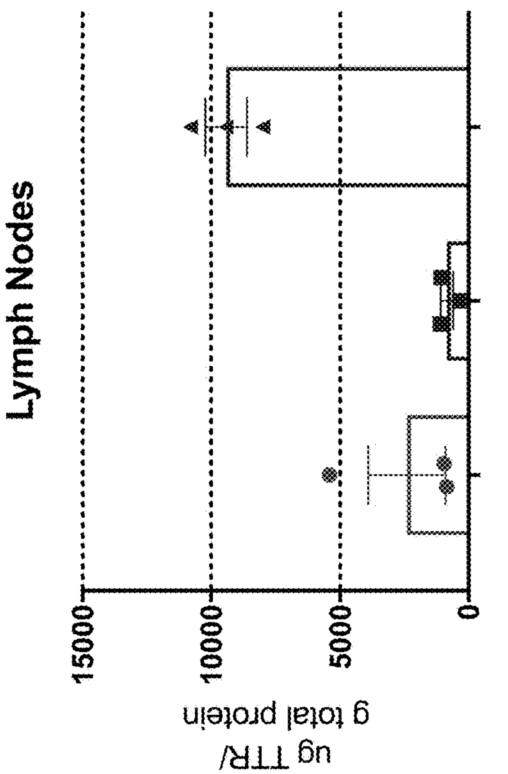
Figure 9K:
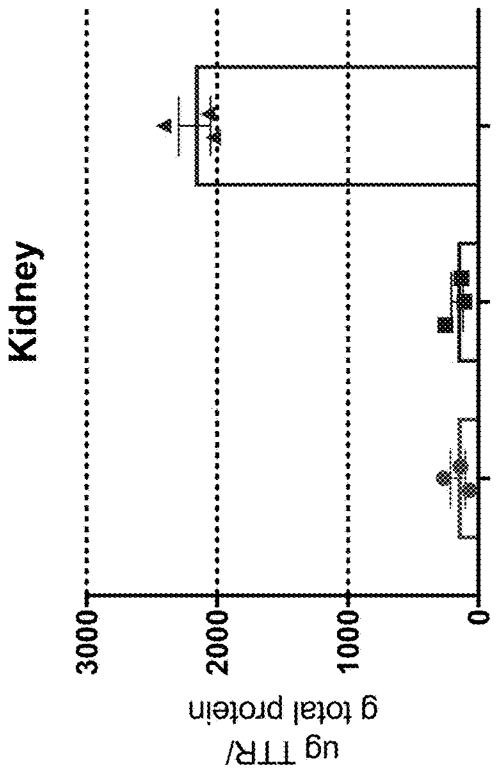
Figure 9L:
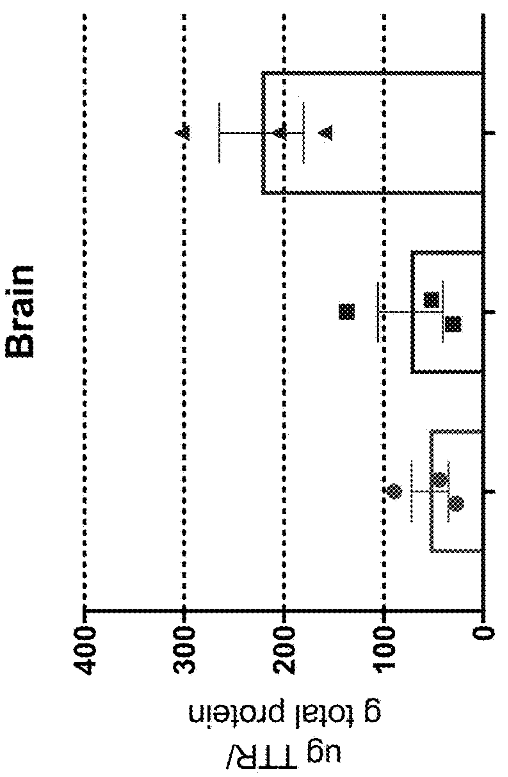

After confirming that the targeted mESC clones were heterozygous for the dCas9 SAM expression cassette and heterozygous for the guide RNA array expression cassette, we used RT-qPCR to determine the relative gene expression. In the case of Ttr, RT-qPCR reached a ct value of 35 in our WT mESCs, mESCs containing the dCas9 SAM components blocked by a stop cassette, and mESCs with the actively expressed dCas9 SAM allele (stop cassette removed). However, after targeting the U6 SAM Ttr guide array to each cell line, only the line containing the active dCas9 SAM system plus guide expression saw a reduction in ct value to 20. See FIG. 8A. This drop of 15 ct values translates to 2500-fold increase in relative gene expression. With such a significant increase in Ttr expression, we wanted to ensure neighboring genes were not impacted by the close proximity of dCas9 SAM activation components. To this end, Dsg2 and B4galt6 (the genes on each side of Ttr) were evaluated by RT-qPCR and determined to have no significant increase of expression in any of the lines mentioned above. See FIGS. 8B and 8C, respectively.

To validate that this gene upregulation is stable and can translate to a mouse model, the targeted clones were microinjected into 8-cell mouse embryos to derive a mouse line. Specifically, a small hole was created in the zona pellucida to facilitate the injection of the targeted mESCs. These injected 8-cell embryos were transferred to surrogate mothers to produce live pups carrying the transgene. Upon gestation in a surrogate mother, the injected embryos produced F0 mice that carried no detectable host embryo contribution. The fully ES-cell-derived mice were normal, healthy, and fertile (with germline transmission).

Figure 10A:
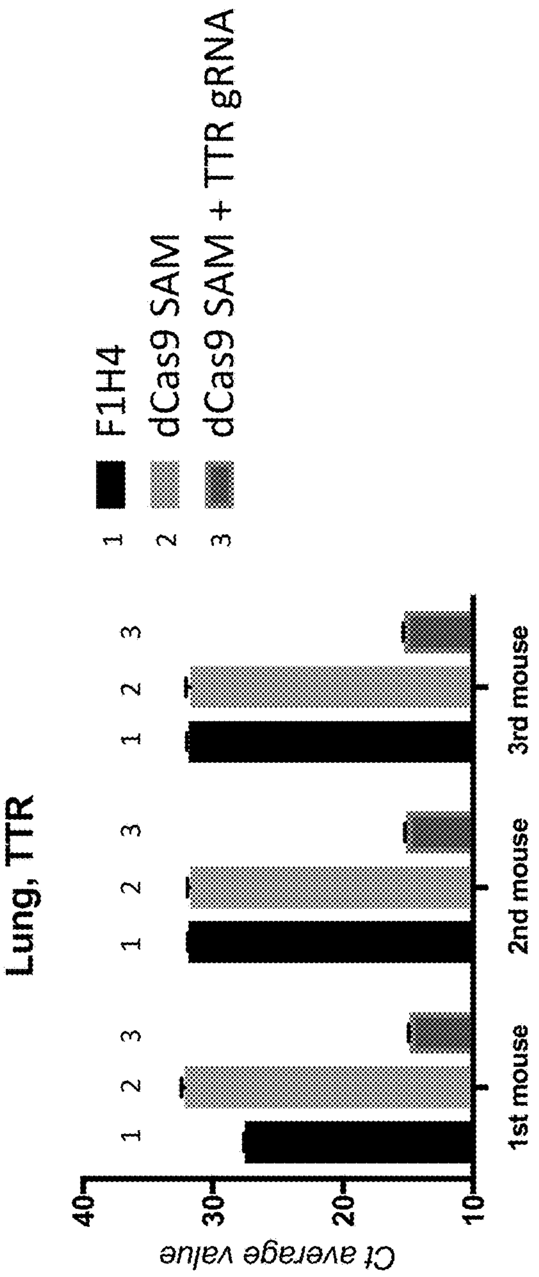
FIGS. 10A and 10B show Ttr mRNA expression levels in lung and spleen, respectively, isolated from wild-type mice, heterozygous dCas9 SAM mice, and heterozygous dCas9 SAM mice that are also heterozygous for a Ttr guide RNA array. Expression levels were determined by RT-qPCR. The y-axis shows the cycle threshold (ct) values.
Figure 10B:
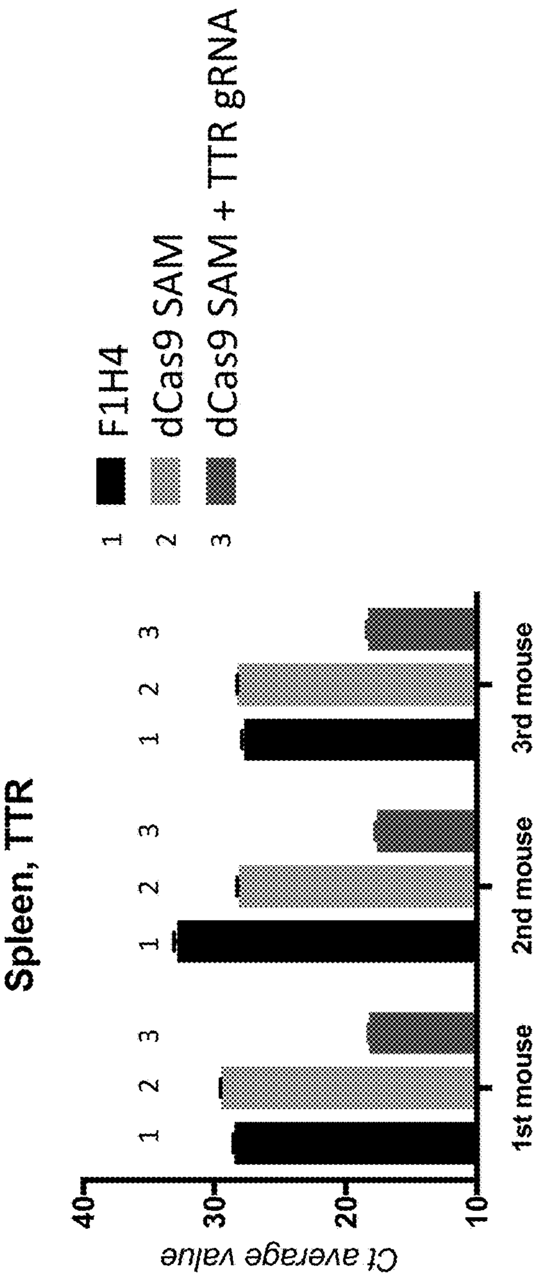
Figure 10C:
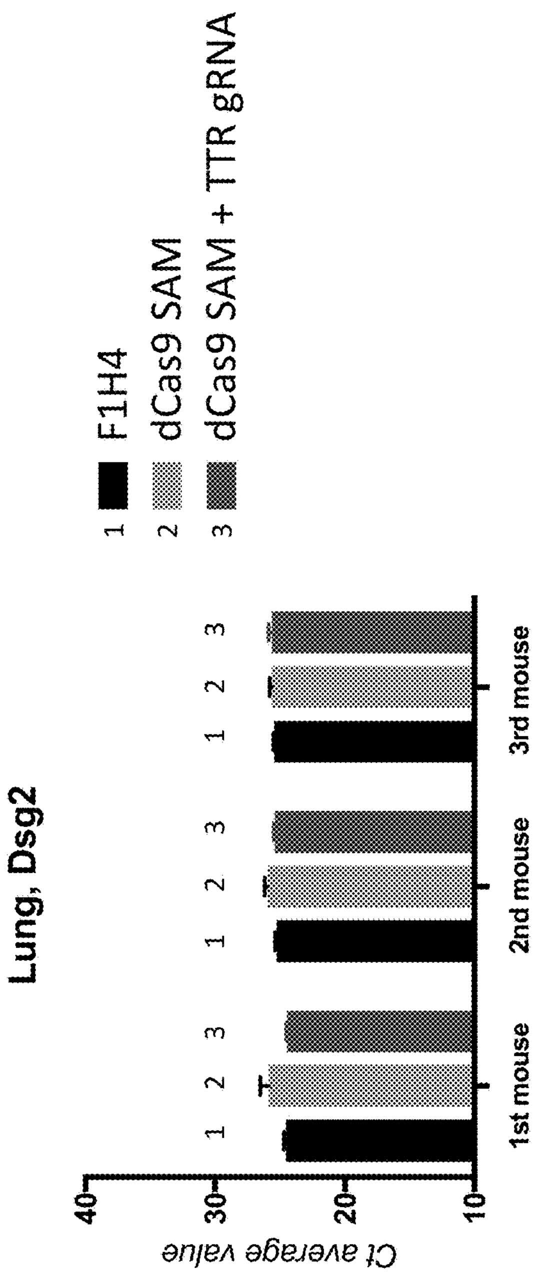
FIGS. 10C and 10D show Dsg2 mRNA expression levels in lung and spleen, respectively, isolated from wild-type mice, heterozygous dCas9 SAM mice, and heterozygous dCas9 SAM mice that are also heterozygous for a Ttr guide RNA array. Expression levels were determined by RT-qPCR. The y-axis shows the cycle threshold (ct) values.
Figure 10D:
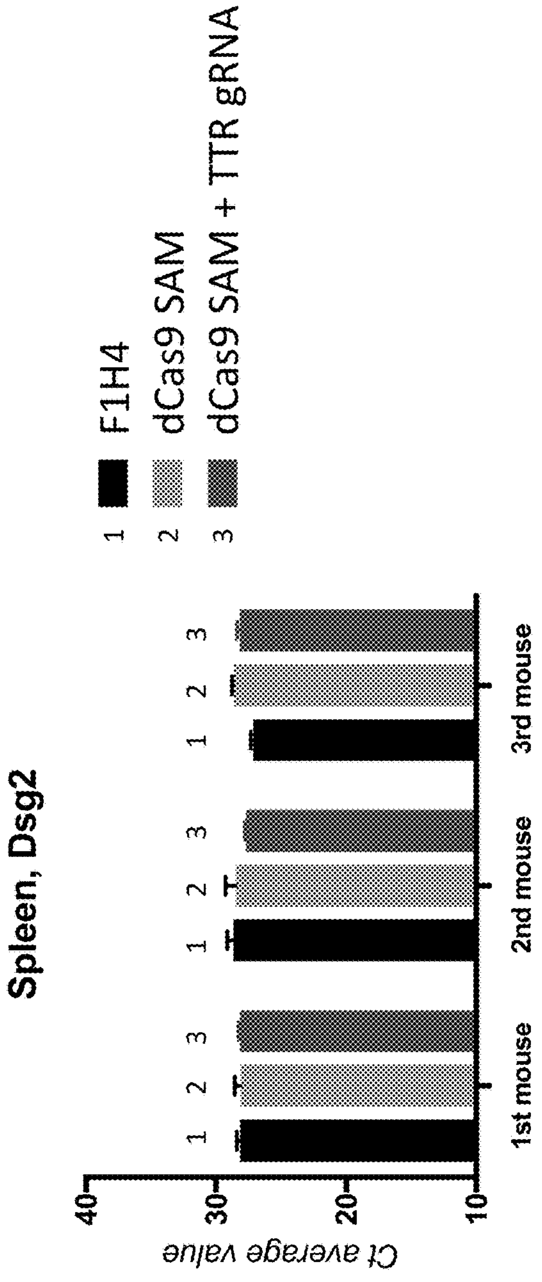
Figure 10E:
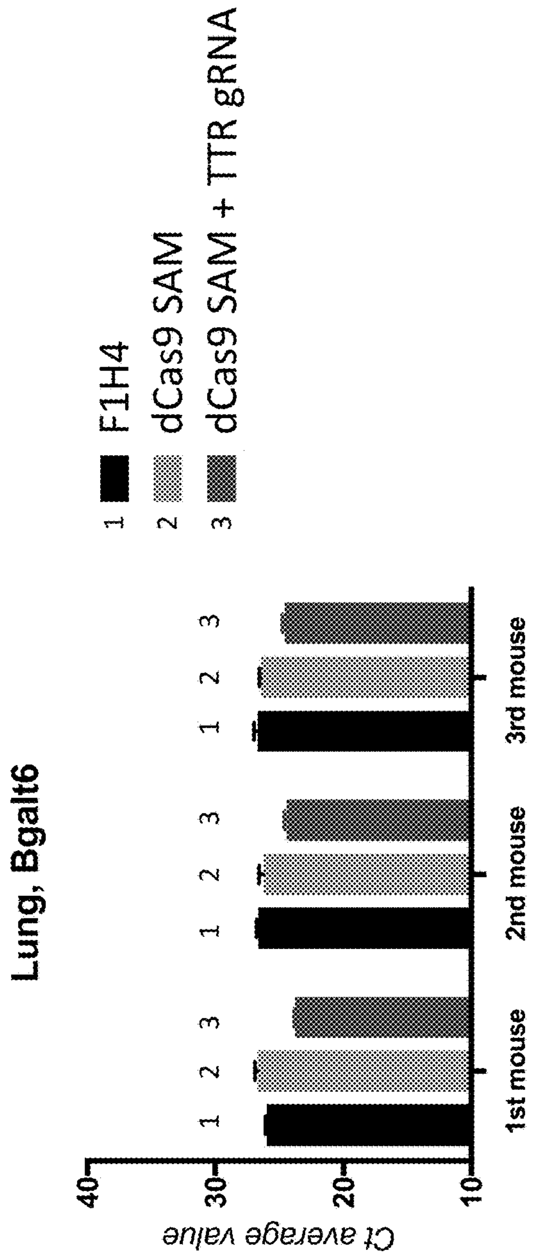
FIGS. 10E and 10F show Bgalt6 mRNA expression levels in lung and spleen, respectively, isolated from wild-type mice, heterozygous dCas9 SAM mice, and heterozygous dCas9 SAM mice that are also heterozygous for a Ttr guide RNA array. Expression levels were determined by RT-qPCR. The y-axis shows the cycle threshold (ct) values.
Figure 10F:
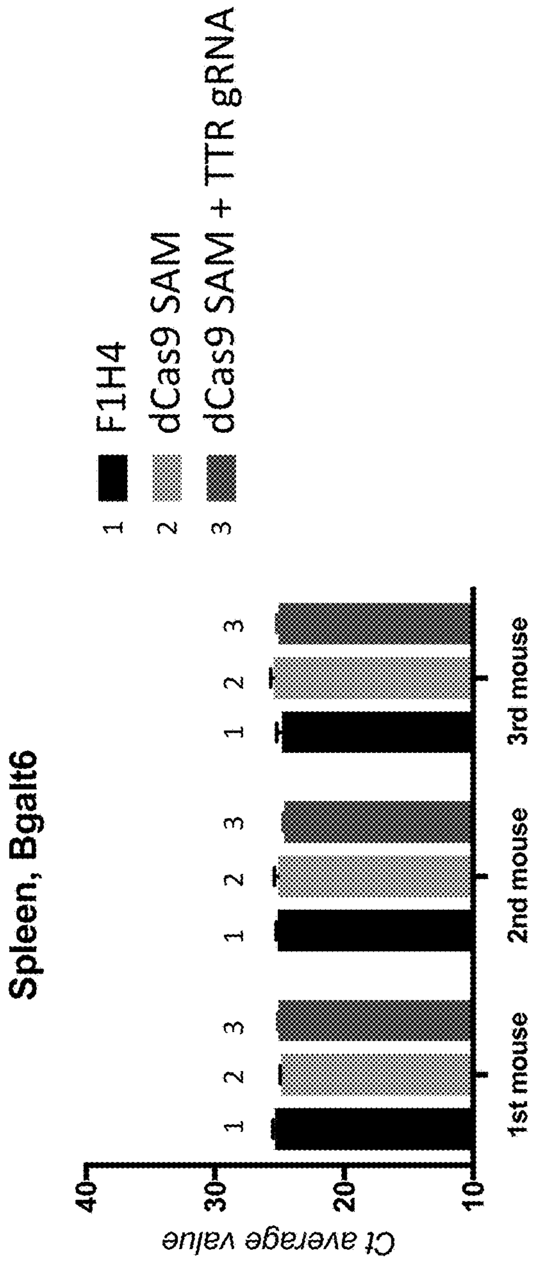

Ttr mRNA expression, assayed by RT-qPCR, was observed in various tissues harvested from wild-type mice, dCas9 SAM mice, and dCas9 SAM mice with genomically integrated Ttr guide RNA arrays. Each of these tissues had the RNA extracted. The genomic DNA was degraded so that it would not count towards the qPCR reaction. The RNA was reverse transcribed and then an assay specific to Ttr was used to detect Ttr transcripts. In the experiments, equal mass amounts of RNA from each tissue were assayed by RT-qPCR. The data show that the level of Ttr expression was elevated in all tissues, including some organs in which it would not normally be expected for TTR to appear. See Table 7. TTR protein expression was also elevated in all tissues examined, including liver, spleen, heart, lung, skeletal muscle, testis, thymus, eye, pancreas, lymph node, kidney, and brain. See FIGS. 9A-9L, respectively. However, the relative of expression was influenced by the tissue. Overall, low Ttr expression in tissues from control mice correlated with higher upregulation by the SAM system. Ttr mRNA expression levels as determined by cycle threshold in lung and spleen are shown in FIGS. 10A and 10B, respectfully. In RT-qPCR, a positive reaction is detected by accumulation of a fluorescent signal. The cycle threshold (ct) is defined as the number of cycles required for the fluorescent signal to exceed background level—a lower ct value indicates higher expression. Moreover, as with the screening in the mESC clones, Dsg2 and B4galt6 (the genes on each side of Ttr) were evaluated by RT-qPCR and determined to have no significant increase of expression. See, e.g., FIGS. 10C, 10D, 10E, and 10F.

TABLE 7

Increases in TTR Expression Relative to Control.

| Tissue | WT TTR (avg Ct) | R26SAM TTR (avg CT) | R26TTR:R26SAM TTR (avg CT) | Relative Expression |
|---|---|---|---|---|
| Liver | 14.11 | 14.45 | 13.01 | 2.9 |
| Brain | 17.89 | 18.04 | 16.29 | 3.19 |
| Eye | 18.84 | 19.38 | 16.78 | 6.89 |
| Kidney | 19.49 | 20.25 | 13.05 | 110.13 |
| Pancreas | 22.72 | 23.04 | 14.29 | 238.68 |
| Thymus | 27.28 | 27.93 | 20.29 | 247.99 |
| Testis | 27.47 | 27.60 | 17.64 | 1935.15 |
| Heart | 28.36 | 29.56 | 17.71 | 1015.33 |
| Spleen | 29.70 | 28.63 | 18.08 | 3323.59 |
| Lung | 30.43 | 31.90 | 15.17 | 79415.55 |
| Skeletal muscle | 32.32 | 29.89 | 19.86 | 5918.21 |

Figure 11:
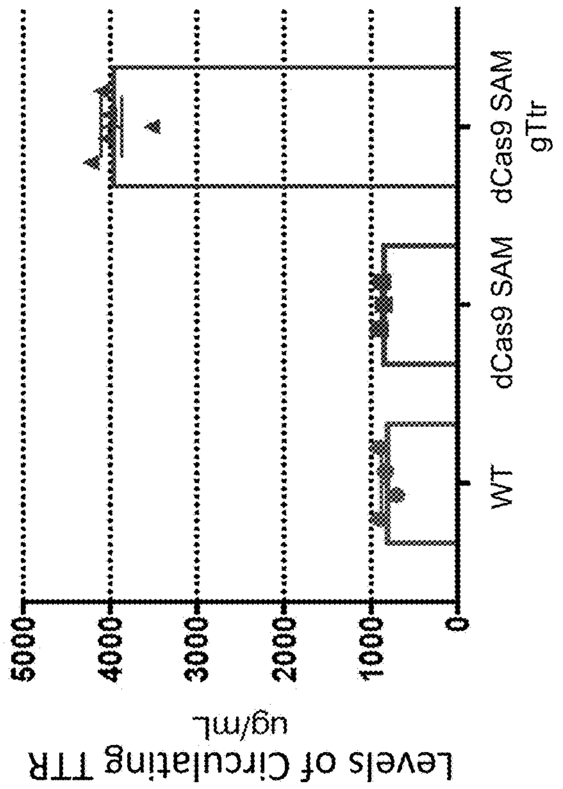
FIG. 11 shows serum levels of TTR in wild-type mice, heterozygous dCas9 SAM mice, and heterozygous dCas9 SAM mice that are also heterozygous for a Ttr guide RNA array as assayed by ELISA.

F0 mice heterozygous for the dCas9 SAM components and the SAM guide RNA arrays targeting Ttr showed an increase from 1000 μg/mL circulating TTR detected in serum by ELISA to 4000 μg/mL when compared to wild type mice or mice expressing the dCas9 SAM components alone. See FIG. 11.

Figure 13:
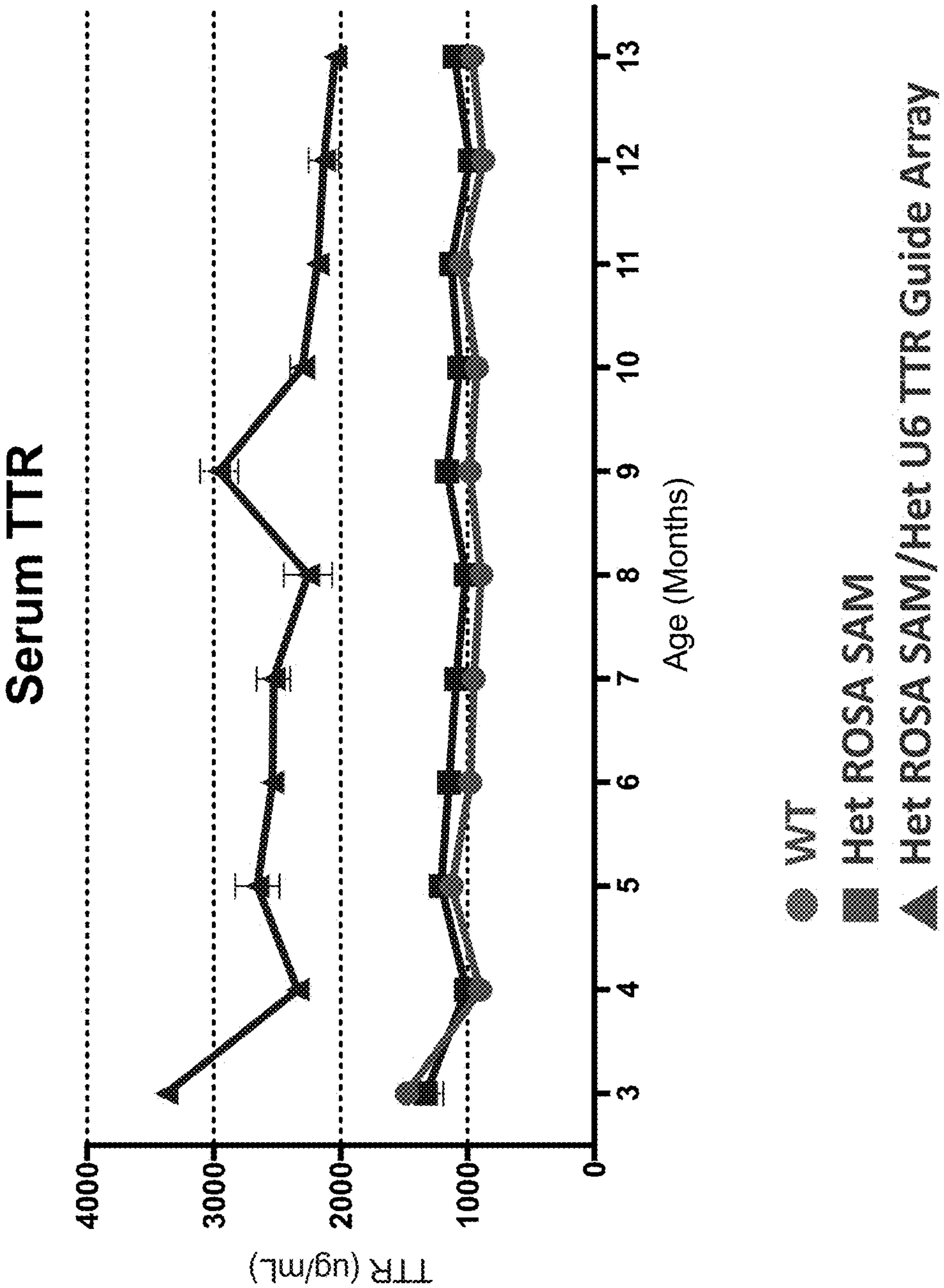
FIG. 13 shows circulating serum levels of TTR in wild-type mice, heterozygous dCas9 SAM mice, and heterozygous dCas9 SAM mice that are also heterozygous for a Ttr guide RNA array as assayed by ELISA. Results from 3-13 months post-injection are shown.

We next assessed whether the increases in TTR levels are stable in mice expressing guide RNAs targeting Ttr from the Rosa26 locus. Three groups of mice were used: (1) F1H4 (WT); (2) heterozygous Rosa26-dCas9-SAM; and (3) Rosa26-dCas9-SAM:Rosa26-U6-TTR guide array (3 guides targeting Ttr)). These mice were generated from mESC as described above, and the F0 generation was aged out to a year. The serum quantity of TTR was measure by ELISA monthly, and animals were observed for any pathological changes. While no pathological changes were observed in these animals at one year, they maintained a 2× to 2.5× increase in circulating TTR. See FIG. 13. These data show that Ttr expression and circulating TTR levels are stable in mice expressing guides targeted to Ttr from the Rosa26 locus for at least one year.

Figure 12:
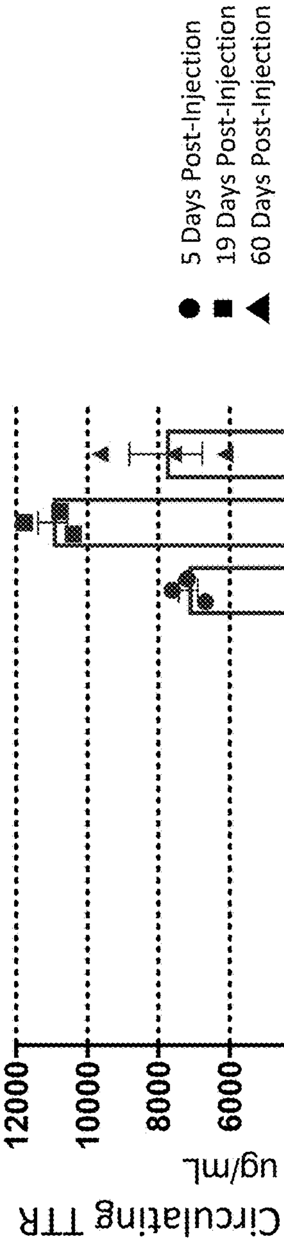
FIG. 12 shows serum levels of TTR in untreated heterozygous dCas9 SAM mice, heterozygous dCas9 SAM mice treated with AAV8-GFP, and heterozygous dCas9 SAM mice treated with AAV8 comprising a Ttr guide RNA array as assayed by ELISA. Results from 5 days, 19 days, and 60 days post-injection are shown.

The system in which expression constructs for both dCas9 SAM components and guide RNA arrays are genomically integrated is a great system for producing very high gene expression throughout the lifespan of the mouse. However, we also wanted to be able to mimic an acute increase of expression. To do this, we introduced an AAV harboring the same Ttr guide arrays into an adult mouse heterozygous for the dCas9 SAM components expressed by Rosa26. The AAV (serotype 8) was introduced via tail vein injection to target liver cells. We analyzed circulating TTR by ELISA at 5, 19, and 60 days post-injection to determine the success of the injection. Surprisingly, the level of TTR circulating in the mouse jumped from 1000 μg/mL in an untreated mouse or a control mouse treated with AAV expressing GFP to 7000 μg/mL in the AAV treated mouse by day 5. By day 19, the serum levels continued to increase to 11,000 g/mL. By day 60, the serum levels were still approximately 8000 μg/mL. See FIG. 12.

Figure 14:
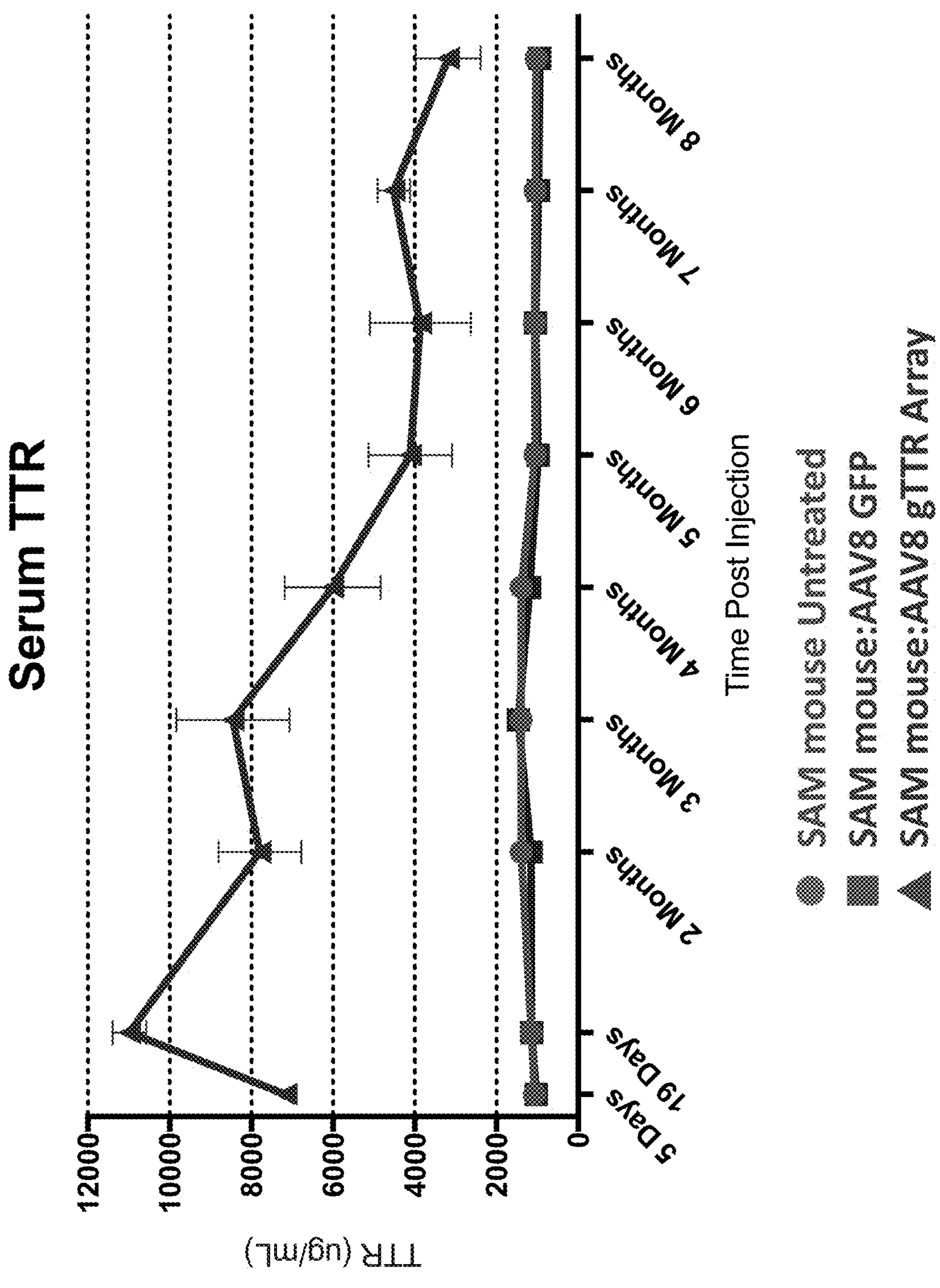
FIG. 14 shows circulating serum levels of TTR in untreated heterozygous dCas9 SAM mice, heterozygous dCas9 SAM mice treated with AAV8-GFP, and heterozygous dCas9 SAM mice treated with AAV8 comprising a Ttr guide RNA array as assayed by ELISA. Results from 5 days, 19 days, 2 months, 3 months, 4 months, 5 months, 6 months, 7 months, and 8 months post-injection are shown.

We next carried out this experiment to 8-months post-injection. As above, three groups of mice were assessed: (1) homozygous Rosa26-dCas9-SAM (untreated); (2) homozygous Rosa26-dCas9-SAM (AAV8-GFP); and (3) homozygous Rosa26-dCas9-SAM (AAV8-gTTR array (3 guides targeting TTR))). These mice were injected with AAV8-GFP or AAV8-gTTR array at 8 weeks of age and were followed out to 8 months post injection. The serum quantity of TTR was measured by ELISA at various early time points and then monthly, and these animals were observed for any pathological changes. While no pathologic changes were observed in these animals at 8 months post-injection, they had an initial increase in circulating TTR of 11× by Day 19, with levels finding a steady state of elevated TTR of ~4× by five months post-injection. See FIG. 14.

Figure 15:
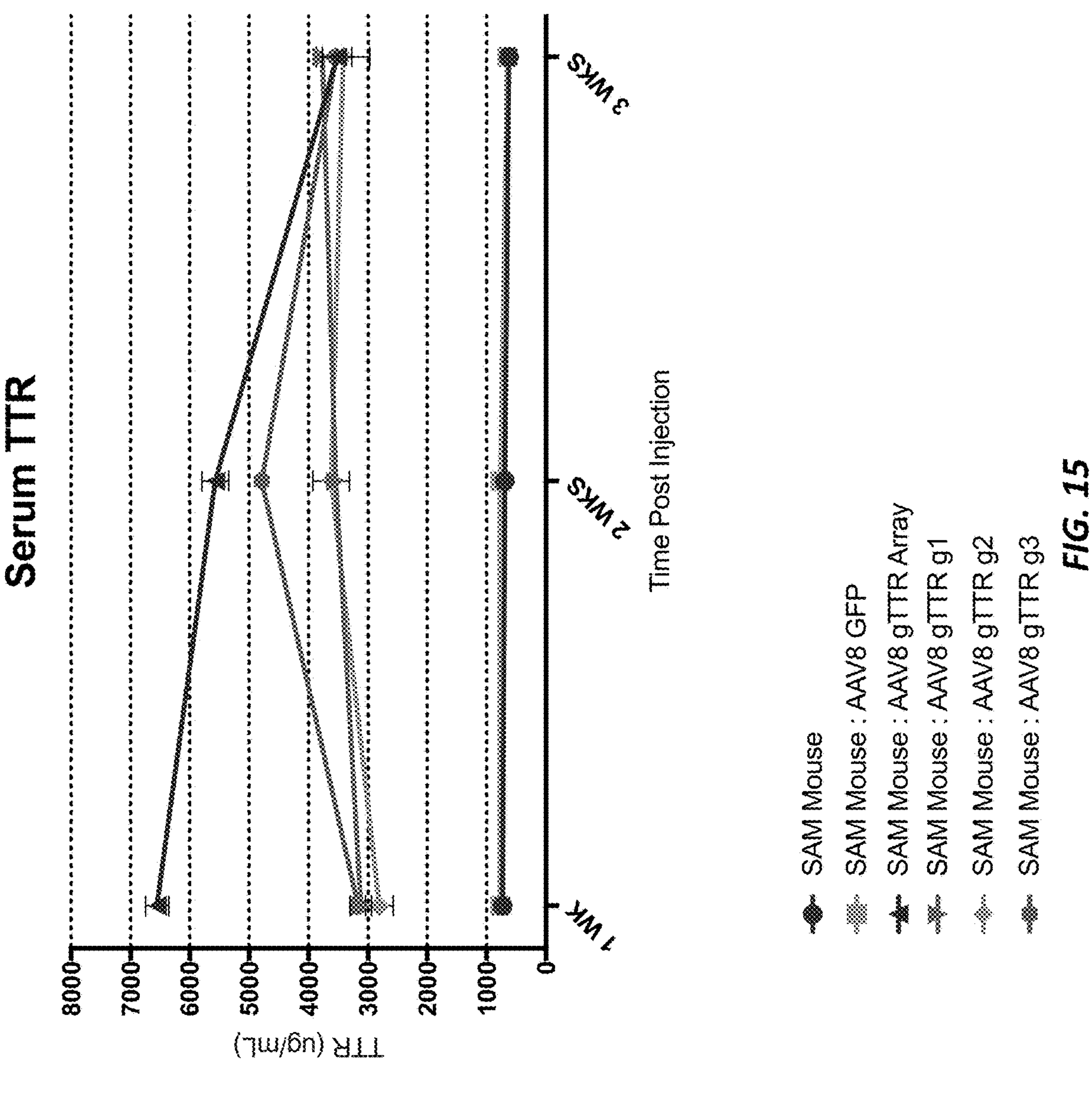
FIG. 15 shows circulating serum levels of TTR in untreated homozygous dCas9 SAM mice, homozygous dCas9 SAM mice treated with AAV8-GFP, and homozygous dCas9 SAM mice treated with AAV8 comprising a Ttr guide RNA array or individual guide RNAs 1, 2, or 3 as assayed by ELISA. Results from 1 week, 2 weeks, and 3 weeks post-injection are shown.

To follow up on whether multiple guide RNAs are needed to allow for upregulation in vivo or if a single guide RNA is sufficient, we took each of the guide RNAs from the guide RNA array and packaged them individually into AAV8. Six groups of mice were assessed in this experiment: (1) homozygous Rosa26-dCas9-SAM (untreated); (2) homozygous Rosa26-dCas9-SAM (AAV8-GFP); (3) homozygous Rosa26-dCas9-SAM (AAV8-gTTR array (3 guides targeting TTR)); (4) homozygous Rosa26-dCas9-SAM (AAV8-gTTR #1); (5) homozygous Rosa26-dCas9-SAM (AAV8-gTTR #2); and (6) homozygous Rosa26-dCas9-SAM (AAV8-gTTR #3)). Sequences for the guide RNA expression cassettes in groups (3)-(6) are set forth in SEQ ID NOS: 67-70, respectively. These mice were injected with AAV8 containing guide RNAs or GFP at 8 weeks of age and were followed out to 8 months post injection. The serum quantity of TTR was measured by ELISA at various early time points to 3 weeks. The results are shown in FIG. 15. At 1 week post-injection, the gTTR guide array exhibited an increase of 6.5× of circulating TTR over the control groups, while each of the single guide RNAs had a 3× increase of circulating TTR in the serum. At 2 weeks post-injection, the gTTR guide array decreased to 5.5× of circulating TTR over the control groups, while two of the single guides maintained a 3.5× amount of circulating TTR in the serum, and gRNA #3 jumped to an almost 5× increase in circulating TTR in the serum. At 3 weeks post-injection, all gRNAs had a level of ~3.5× increase in circulating TTR in the serum over the WT controls. These results suggested that the guide RNA array can provide an initial high burst of protein, but over time single gRNAs can perform equally well at gene upregulation resulting in circulating TTR protein.

Figure 19:
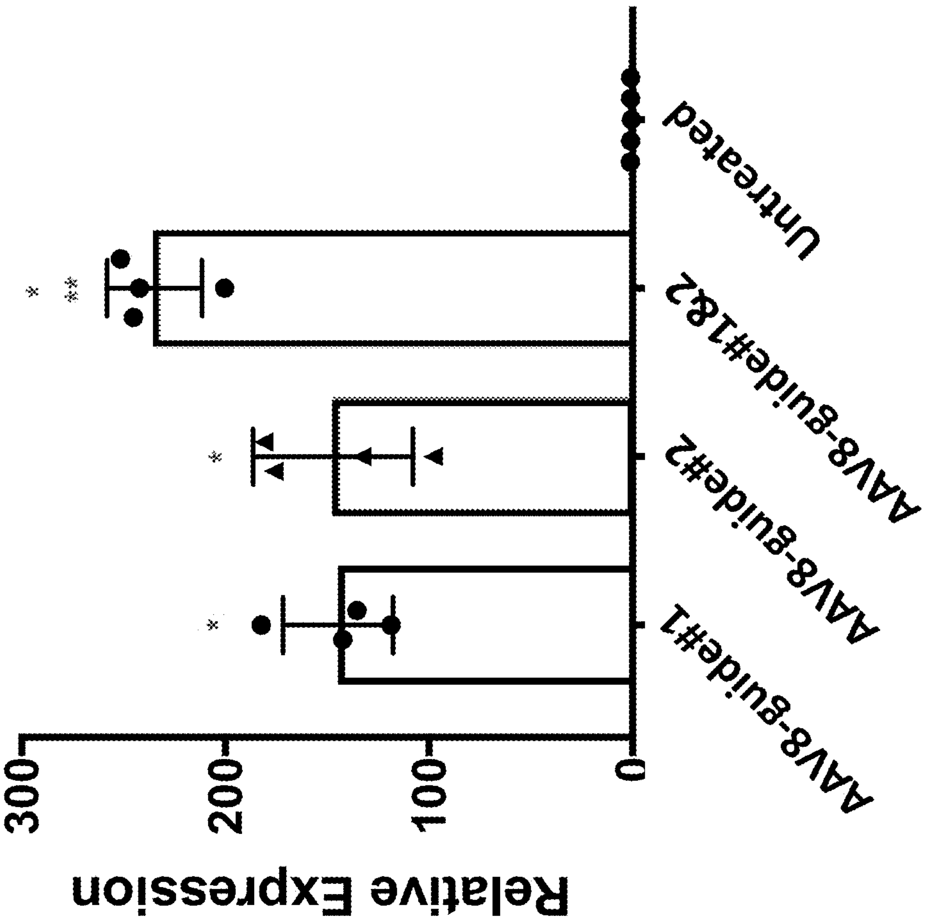
FIG. 19 shows relative mRNA expression levels of Target Gene 1 in livers isolated from untreated mice, homozygous dCas9 SAM mice treated with AAV8 comprising Target Gene 1 guide RNA #1, homozygous dCas9 SAM mice treated with AAV8 comprising Target Gene 1 guide RNA #2, or homozygous dCas9 SAM mice treated with AAV8 comprising Target Gene 1 guide RNAs #1&2. Expression levels were determined by RT-qPCR. The y-axis shows expression relative to the untreated samples. * indicates $p<0.0001$ compared to untreated. ** indicates $p<0.001$ compared to guide RNA #1 or guide RNA #2.

To continue to evaluate if single guides or multiple guides integrated into the AAV were more successful at gene upregulation in Rosa26-dCas9-SAM mice, we evaluated Target Gene 1 expression in liver using either one guide RNA or two guide RNAs. RNA expression was assessed through TAQMAN at three weeks post-injection. We observed a significant upregulation of Target Gene 1 in all three groups ((1) homozygous Rosa26-dCas9-SAM(AAV8-Target Gene 1 guide RNA #1), (2) homozygous Rosa26-dCas9-SAM(AAV8-Target Gene 1 guide RNA #2), and (3) homozygous Rosa26-dCas9-SAM(AAV8-Target Gene 1 guide RNAs #1&2)) compared to untreated homozygous Rosa26-dCas9-SAM. There was a significant increase in RNA expression in the two guide RNA group when compared to the one guide RNA groups at this 3 week post-injection time point. Use of the AAV8 with two guide RNAs resulted in over a 200-fold increase in liver expression over untreated, whereas use of AAV8 with one guide RNA resulted in over a 100-fold increase in liver expression over untreated. See FIG. 19.

Though the experiments described above have primarily focused on upregulation of the mouse Ttr gene, similarly increased expression was also observed when targeting other genes (data not shown). Further, by using different serotypes or controlling dCas9 SAM expression using tissue-specific Cre treatment, we can control the gene upregulation timing and tissue specificity to generate robust, reliable disease models.

Example 3. Validation of SAM-Ready Mice with Pcsk9 and Ldlr Guide RNAs

As further validation of this system in vivo, two genes (Pcsk9 and Ldlr) involved in the cholesterol pathway were chosen as targets for up-regulation, and the physiological effects on cholesterol levels were observed over a five week time course. Three groups of mice were assessed: (1) homozygous Rosa26-dCas9-SAM(AAV8-Pcsk9 guide array); (2) homozygous Rosa26-dCas9-SAM(AAV8-Ldlr guide array); and (3) homozygous Rosa26-dCas9-SAM(Untreated).

The sequence for the Pcsk9 guide RNA array is set forth in SEQ ID NO: 85. The guide RNA array encodes three guide RNAs. The region including the promoters and guide RNA coding sequences is set forth in SEQ ID NO: 98. The guide RNA target sequence (not including PAM) in the mouse Pcsk9 gene that are targeted by the guide RNAs in the array are set forth in SEQ ID NOS: 89-91. The single guide RNAs targeting these guide RNA target sequences are set forth in SEQ ID NOS: 92-94, respectively.

The sequence for the Ldlr guide RNA array is set forth in SEQ ID NO: 71. The guide RNA array encodes three guide RNAs. The region including the promoters and guide RNA coding sequences is set forth in SEQ ID NO: 84. The guide RNA target sequence (not including PAM) in the mouse Ldlr gene that are targeted by the guide RNAs in the array are set forth in SEQ ID NOS: 75-77. The single guide RNAs targeting these guide RNA target sequences are set forth in SEQ ID NOS: 78-80, respectively.

Figure 16A:
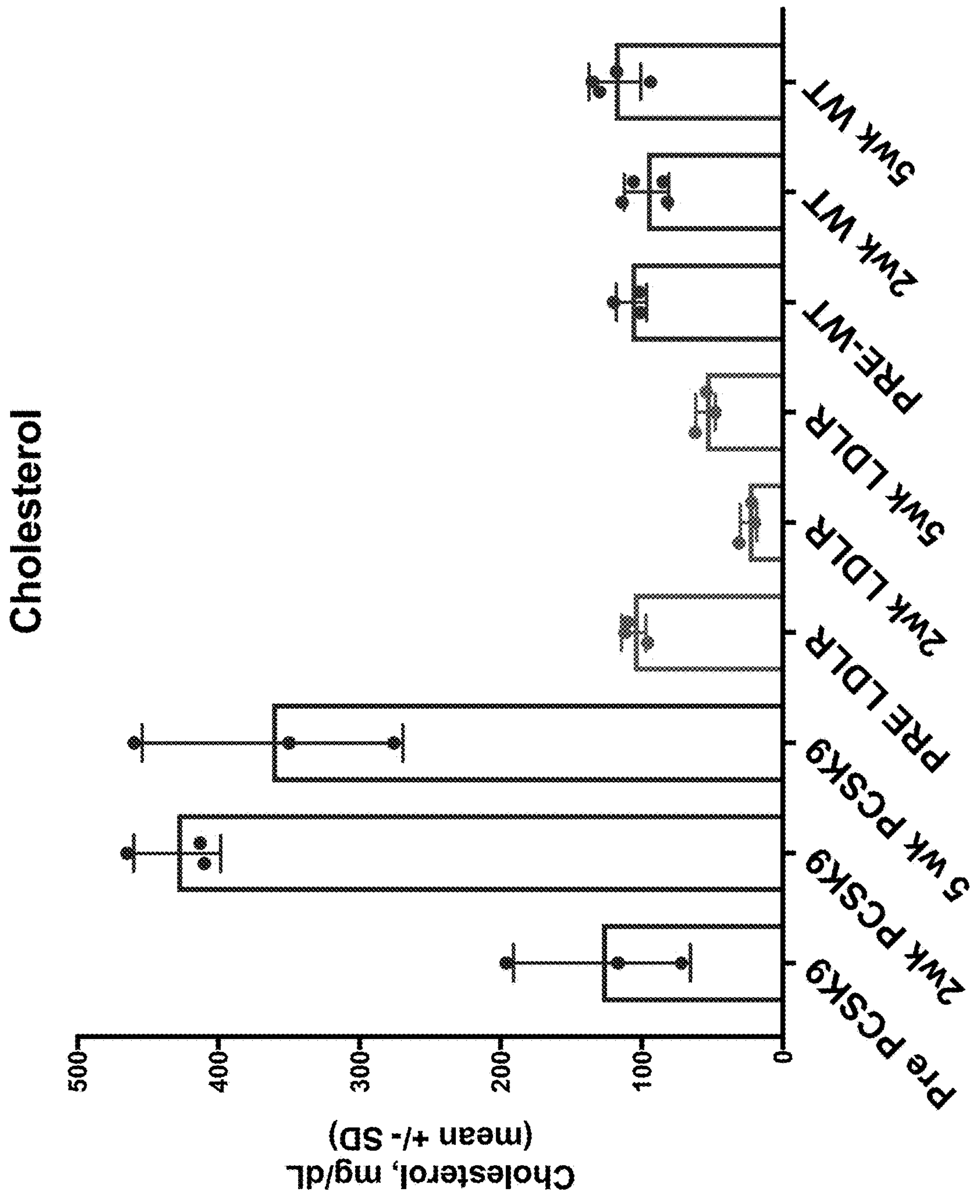
FIGS. 16A and 16B show cholesterol and LDL levels, respectively, in untreated homozygous dCas9 SAM mice (Pre PCSK9, Pre LDLR, Pre-WT, 2 wk WT, or 5 wk WT), homozygous dCas9 SAM mice treated with AAV8 comprising a Pcsk9 guide RNA array, or homozygous dCas9 SAM mice treated with AAV8 comprising an Ldlr guide RNA array.
Figure 16B:
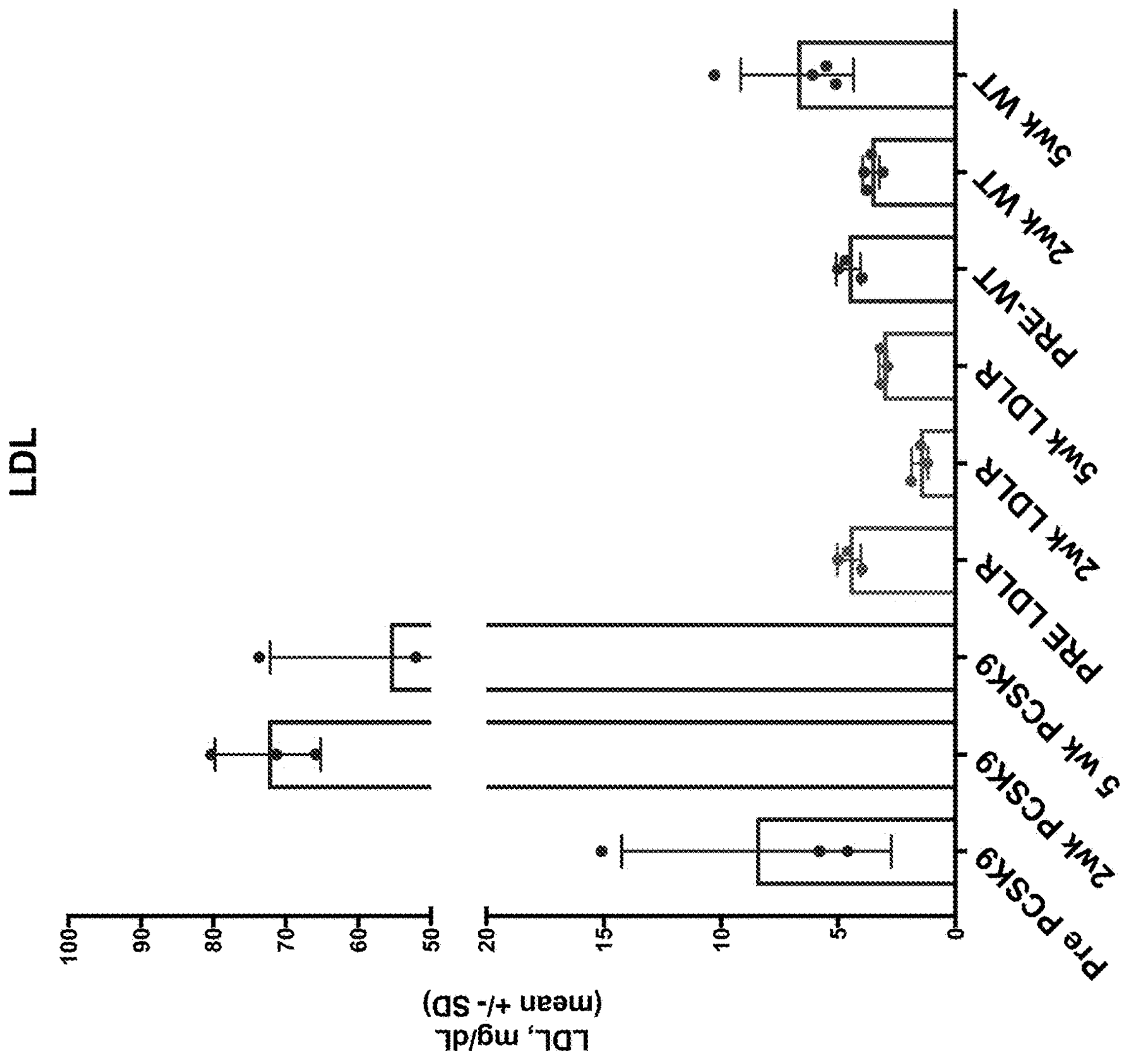

The results are shown in FIG. 16A. At two weeks post-injection, Rosa26-dCas9-SAM(AAV8-Pcsk9 guide array) exhibited an increase of 3.5× in cholesterol levels over cholesterol levels pre-injection. In contrast, Rosa26-dCas9-SAM(AAV8-Ldlr guide array) showed a decrease in total cholesterol levels by 75% over pre-injection levels. Untreated animals maintained their cholesterol. At 5 weeks post-injection, Rosa26-dCas9-SAM(AAV8-Pcsk9 guide array) exhibited a 3× increased in cholesterol levels over cholesterol levels pre-injection. In contrast, Rosa26-dCas9-SAM(AAV8—Ldlr guide array) showed a decrease in total cholesterol levels by 50% over pre-injection levels. Untreated animals maintained their cholesterol. Similar effects were observed with LDL levels. See FIG. 16B.

Figure 17B:
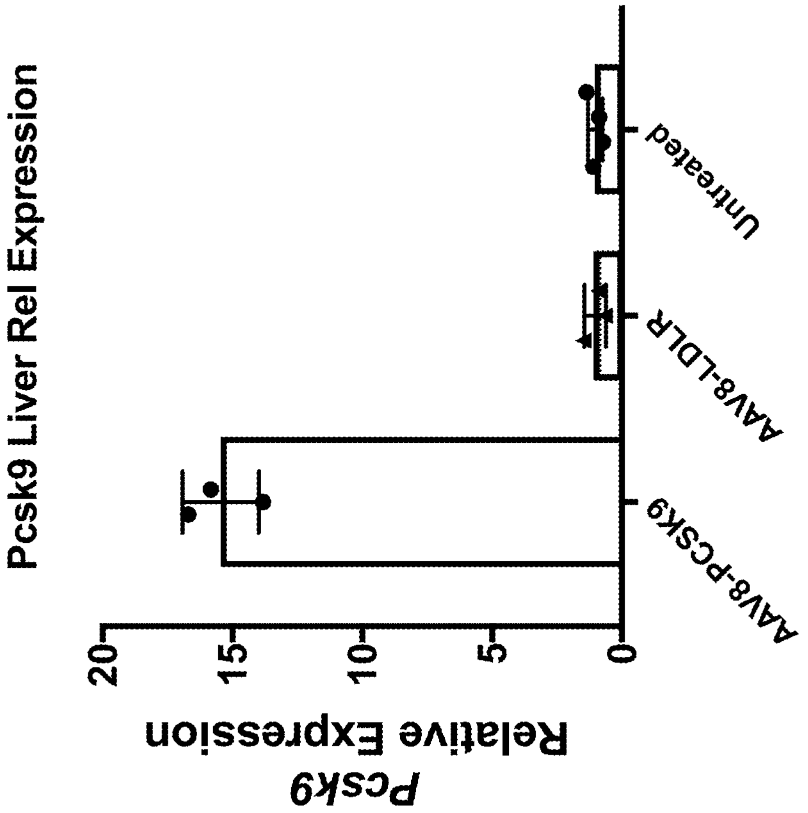
FIGS. 17A and 17B show relative Ldlr and Pcsk9 mRNA expression levels in livers isolated from untreated homozygous dCas9 SAM mice, homozygous dCas9 SAM mice treated with AAV8 comprising a Pcsk9 guide RNA array, and homozygous dCas9 SAM mice treated with AAV8 comprising an Ldlr guide RNA array.
Figure 17A:
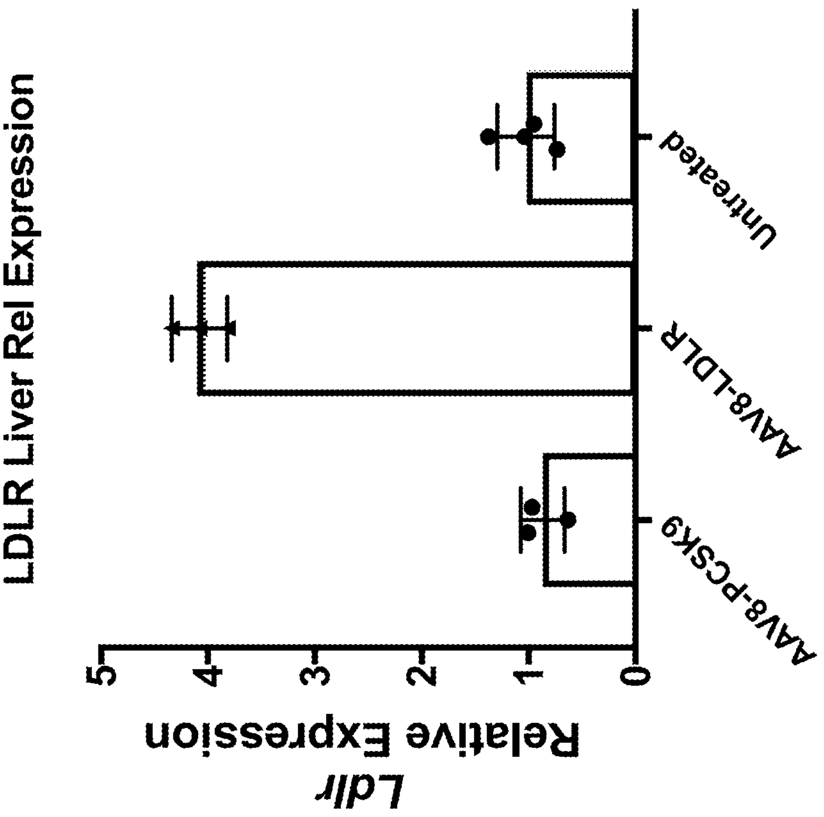

Next, expression of Ldlr and Pcsk9 was assessed. TAQMAN expression levels of Ldlr and Pcsk9 in the livers of the mice in the above experiment at 5 weeks post-injection are shown in FIGS. 17A and 17B, respectively.

Figure 18A:
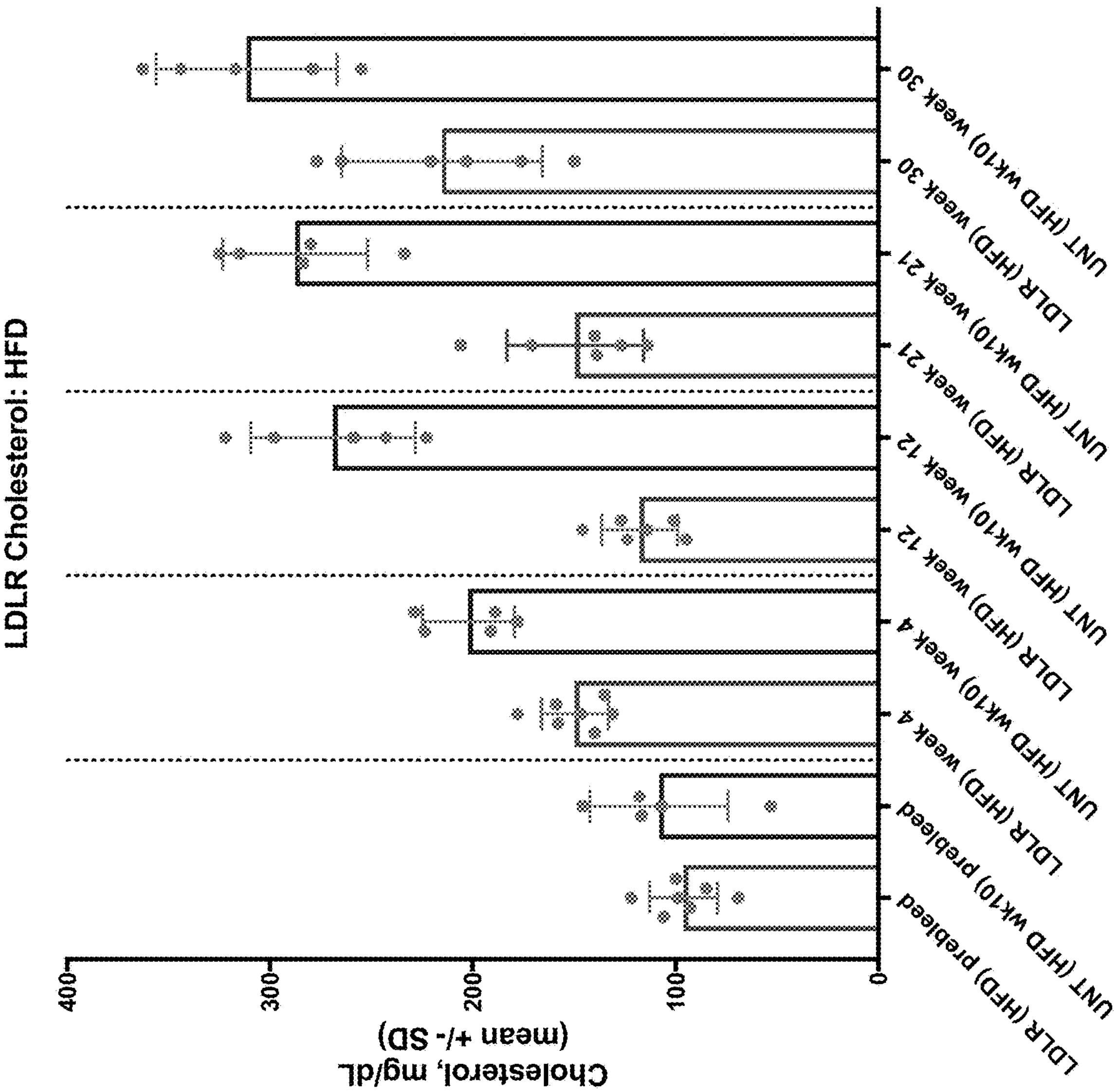
FIGS. 18A and 18B show cholesterol and LDL levels, respectively, in untreated homozygous dCas9 SAM mice (UNT) or homozygous dCas9 SAM mice treated with AAV8 comprising an Ldlr guide RNA array (LDLR (HFD)).
Figure 18B:
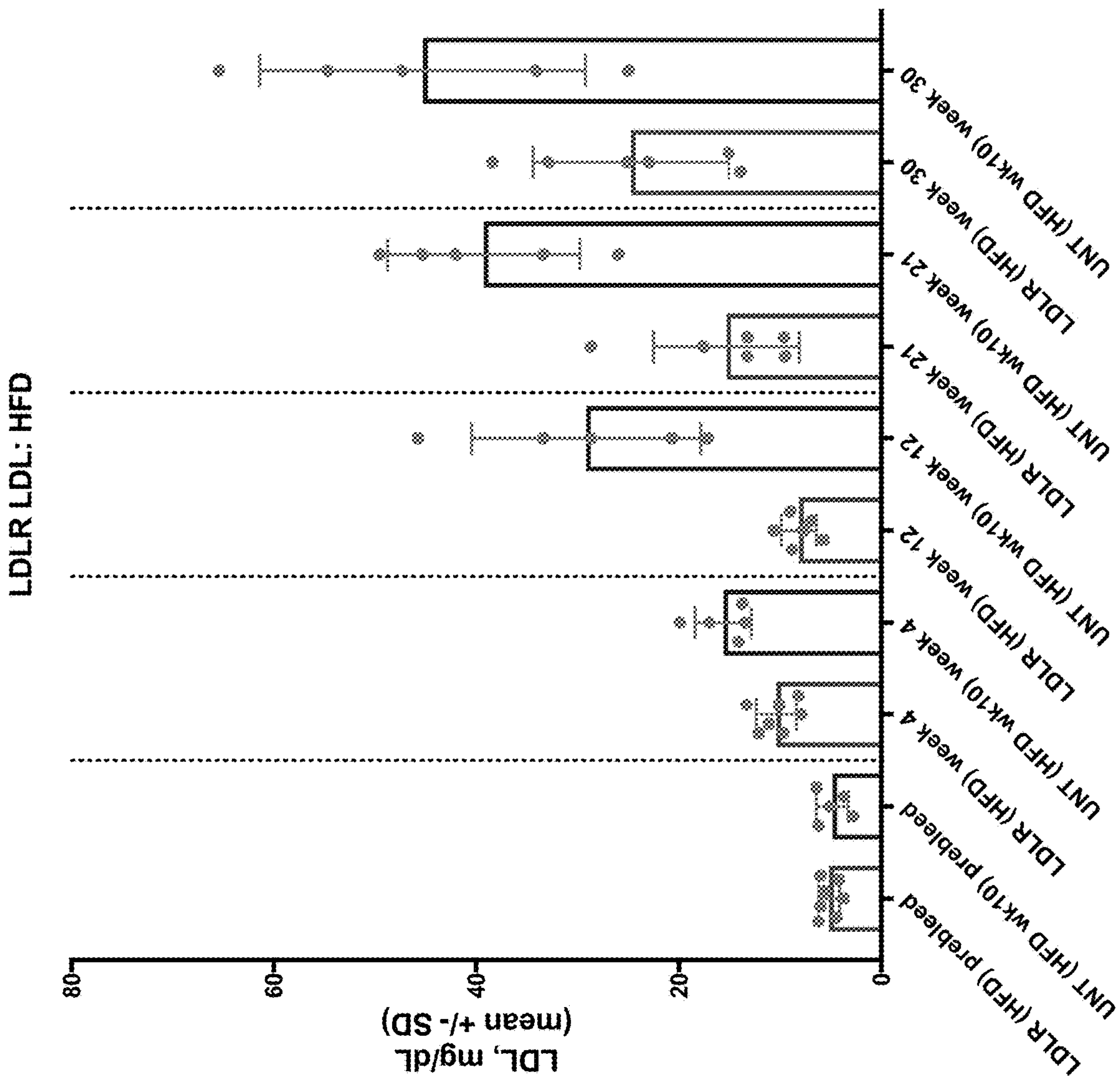

As further validation showing that the increase of LDLR through the dCAS9-SAM system could lead to a long-term benefit, we evaluated the AAV8-Ldlr guide RNA array in homozygous dCas9-SAM mice fed a high-fat diet and followed them for 20 weeks after injection of the AAV8-Ldlr guide RNA array. Mice were pre-bled for initial cholesterol levels and then placed on a high fat diet (HFD) for 8 weeks (bled every 4 weeks to test cholesterol levels). The results for cholesterol and LDL levels are shown in FIGS. 18A and 18B, respectively. After 8 weeks, mice were injected either with AAV8-Ldlr guide array or left untreated. The mice were bled monthly, and their total cholesterol and LDL levels were evaluated. During this time frame, the mice treated with the AAV8-Ldlr guide array had a lower total cholesterol and lower LDL levels when compared to the untreated mice on a HFD.

We claim:

1. A non-human animal comprising a genomically integrated expression cassette, wherein the expression cassette comprises:

(a) a nucleic acid encoding a chimeric Clustered Regularly Interspaced Short Palindromic Repeats (CRISPR) associated (Cas) protein comprising a nuclease-inactive Cas protein fused to a transcriptional activation domain; and (b) a nucleic acid encoding a chimeric adaptor protein comprising an adaptor fused to transcriptional activation domains, wherein the expression cassette further comprises a polyadenylation signal or transcription terminator upstream of the nucleic acid encoding the chimeric Cas protein, wherein the polyadenylation signal or transcription terminator is flanked by recombinase recognition sites recognized by a site-specific recombinase, wherein the expression cassette comprises the sequence set forth in SEQ ID NO: 31.

2. The non-human animal of claim 1, wherein the polyadenylation signal or transcription terminator has been excised in a tissue in the non-human animal.

3. The non-human animal of claim 2, further comprising one or more guide RNAs or an expression cassette encoding one or more guide RNAs, wherein the one or more guide RNAs each comprise one or more adaptor-binding elements to which the chimeric adaptor protein can specifically bind, and wherein the one or more guide RNAs form complexes with the chimeric Cas protein and chimeric adaptor protein and guide them to a target sequence within a target gene, increasing expression of the target gene.

4. The non-human animal of claim 3, wherein the target gene is a gene expressed in the liver.

5. The non-human animal of claim 3, wherein the target sequence comprises a regulatory sequence within the target gene, and wherein the regulatory sequence comprises a promoter or an enhancer.

6. The non-human animal of claim 3, wherein the target sequence is within 200 base pairs of the transcription start site of the target gene, or wherein the target sequence is within the region 200 base pairs upstream of the transcription start site and 1 base pair downstream of the transcription start site.

7. The non-human animal of claim 3, wherein each of the one or guide RNAs comprises two adaptor-binding elements to which the chimeric adaptor protein can specifically bind, and wherein a first adaptor-binding element is within a first loop of each of the one or more guide RNAs, and a second adaptor-binding element is within a second loop of each of the one or more guide RNAs.

8. The non-human animal of claim 7, wherein each of one or more guide RNAs is a single guide RNA comprising a CRISPR RNA (crRNA) portion fused to a transactivating CRISPR RNA (tracrRNA) portion, and wherein the first loop is the tetraloop corresponding to residues 13-16 of SEQ ID NO: 12 and the second loop is the stem loop 2 corresponding to residues 53-56 of SEQ ID NO: 12.

9. The non-human animal of claim 3, wherein the adaptor-binding element comprises the sequence set forth in SEQ ID NO: 16, or wherein each of the one or more guide RNAs comprises the sequence set forth in SEQ ID NO: 40 or 63.

10. The non-human animal of claim 3, wherein at least one of the one or more guide RNAs targets a disease-associated gene.

11. The non-human animal of claim 10, wherein the disease-associated gene is a Ttr gene, and wherein the Ttr-targeting guide RNA targets a sequence comprising the sequence set forth in any one of SEQ ID NOS: 34-36 or wherein the Ttr-targeting guide RNA comprises the sequence set forth in any one of SEQ ID NOS: 37-39.

12. The non-human animal of claim 3, wherein at least one of the one or more guide RNAs targets a Pcsk9 gene, and wherein the Pcsk9-targeting guide RNA targets a sequence comprising the sequence set forth in any one of SEQ ID NOS: 89-91 or wherein the Pcsk9-targeting guide RNA comprises the sequence set forth in any one of SEQ ID NOS: 92-94, and wherein the method causes hypercholesterolemia in the non-human animal.

13. The non-human animal of claim 3, wherein at least one of the one or more guide RNAs targets a Ldlr gene, and wherein the Ldlr-targeting guide RNA targets a sequence comprising the sequence set forth in any one of SEQ ID NOS: 75-77 or wherein the Ldlr-targeting guide RNA comprises the sequence set forth in any one of SEQ ID NOS: 78-80.

14. The non-human animal of claim 3, wherein the one or more guide RNAs target two or more target genes, or wherein the one or more guide RNAs comprise multiple guide RNAs that target a single target gene.

15. The non-human animal of claim 14, wherein the one or more guide RNAs comprise at least three guide RNAs that target a single target gene.

16. The non-human animal of claim 15, wherein:

(a) the at least three guide RNAs target the mouse Ttr locus, and wherein a first guide RNA targets a sequence comprising SEQ ID NO: 34 or comprises the sequence set forth in SEQ ID NO: 37, a second guide RNA targets a sequence comprising SEQ ID NO: 35 or comprises the sequence set forth in SEQ ID NO: 38, and a third guide RNA targets a sequence comprising SEQ ID NO: 36 or comprises the sequence set forth in SEQ ID NO: 39;

(b) the at least three guide RNAs target the mouse Pcsk9 locus, and wherein a first guide RNA targets a sequence comprising SEQ ID NO: 89 or comprises the sequence set forth in SEQ ID NO: 92, a second guide RNA targets a sequence comprising SEQ ID NO: 90 or comprises the sequence set forth in SEQ ID NO: 93, and a third guide RNA targets a sequence comprising SEQ ID NO: 91 or comprises the sequence set forth in SEQ ID NO: 94; or (c) the at least three guide RNAs target the mouse Ldlr locus, and wherein a first guide RNA targets a sequence comprising SEQ ID NO: 75 or comprises the sequence set forth in SEQ ID NO: 78, a second guide RNA targets a sequence comprising SEQ ID NO: 76 or comprises the sequence set forth in SEQ ID NO: 79, and a third guide RNA targets a sequence comprising SEQ ID NO: 77 or comprises the sequence set forth in SEQ ID NO: 80.

17. The non-human animal of claim 3, wherein the non-human animal comprises the one or more guide RNAs in the form of RNA.

18. The non-human animal of claim 3, wherein the non-human animal comprises the expression cassette encoding the one or more guide RNAs.

19. The non-human animal of claim 18, wherein the expression cassette encoding the one or more guide RNAs is genomically integrated.

20. The non-human animal of claim 18, wherein each of the one or more guide RNAs is encoded by a DNA operably linked to a separate U6 promoter.

21. The non-human animal of claim 18, wherein the expression cassette encoding the one or more guide RNAs is genomically integrated, wherein each of the one or more guide RNAs is encoded by a DNA operably linked to a separate U6 promoter, and wherein the one or more guide RNAs comprise multiple guide RNAs that target a single target gene.

22. The non-human animal of claim 1, wherein the non-human animal further comprises a Cre recombinase expression cassette comprising a Cre recombinase coding sequence operably linked to a tissue-specific promoter, and the polyadenylation signal or transcription terminator has been excised in a tissue-specific manner, or wherein the non-human animal further comprises a Cre recombinase.

23. The non-human animal of claim 22, wherein the non-human animal comprises a genomically integrated Cre recombinase expression cassette comprising the Cre recombinase coding sequence operably linked to the tissue-specific promoter, wherein the tissue-specific promoter is an albumin promoter.

24. The non-human animal of claim 1, wherein the genomically integrated expression cassette is integrated into a safe harbor locus, and wherein the expression cassette is operably linked to an endogenous promoter in the safe harbor locus.

25. The non-human animal of claim 24, wherein the safe harbor locus is a Rosa26 locus.

26. The non-human animal of claim 1, wherein the non-human animal is a mammal.

27. The non-human animal of claim 26, wherein the mammal is a rodent that is a rat or a mouse.

28. The non-human animal of claim 27, wherein the rodent is the mouse.

29. A non-human animal cell of the non-human animal of claim 1, wherein the non-human animal cell comprises a genomically integrated expression cassette, wherein the expression cassette comprises:

(a) a nucleic acid encoding a chimeric Clustered Regularly Interspaced Short Palindromic Repeats (CRISPR) associated (Cas) protein comprising a nuclease-inactive Cas protein fused to a transcriptional activation domain; and (b) a nucleic acid encoding a chimeric adaptor protein comprising an adaptor fused to transcriptional activation domains, wherein the expression cassette further comprises a polyadenylation signal or transcription terminator upstream of the nucleic acid encoding the chimeric Cas protein, wherein the polyadenylation signal or transcription terminator is flanked by recombinase recognition sites recognized by a site-specific recombinase, wherein the expression cassette comprises the sequence set forth in SEQ ID NO: 31.

* * * * *

SEQUENCE LISTING

```
Sequence total quantity: 98
SEQ ID NO: 1            moltype = AA  length = 1471
FEATURE                 Location/Qualifiers
REGION                  1..1471
                        note = Synthetic
source                  1..1471
                        mol_type = protein
                        organism = synthetic construct
SEQUENCE: 1
MKRPAATKKA GQAKKKKDKK YSIGLAIGTN SVGWAVITDE YKVPSKKFKV LGNTDRHSIK  60
KNLIGALLFD SGETAEATRL KRTARRRYTR RKNRICYLQE IFSNEMAKVD DSFFHRLEES  120
FLVEEDKKHE RHPIFGNIVD EVAYHEKYPT IYHLRKKLVD STDKADLRLI YLALAHMIKF  180
RGHFLIEGDL NPDNSDVDKL FIQLVQTYNQ LFEENPINAS GVDAKAILSA RLSKSRRLEN  240
LIAQLPGEKK NGLFGNLIAL SLGLTPNFKS NFDLAEDAKL QLSKDTYDDD LDNLLAQIGD  300
QYADLFLAAK NLSDAILLSD ILRVNTEITK APLSASMIKR YDEHHQDLTL LKALVRQQLP  360
EKYKEIFFDQ SKNGYAGYID GGASQEEFYK FIKPILEKMD GTEELLVKLN REDLLRKQRT  420
```

-continued

```
FDNGSIPHQI HLGELHAILR RQEDFYPFLK DNREKIEKIL TFRIPYYVGP LARGNSRFAW  480
MTRKSEETIT PWNFEEVVDK GASAQSFIER MTNFDKNLPN EKVLPKHSLL YEYFTVYNEL  540
TKVKYVTEGM RKPAFLSGEQ KKAIVDLLFK TNRKVTVKQL KEDYFKKIEC FDSVEISGVE  600
DRFNASLGTY HDLLKIIKDK DFLDNEENED ILEDIVLTLT LFEDREMIEE RLKTYAHLFD  660
DKVMKQLKRR RYTGWGRLSR KLINGIRDKQ SGKTILDFLK SDGFANRNFM QLIHDDSLTF  720
KEDIQKAQVS GQGDSLHEHI ANLAGSPAIK KGILQTVKVV DELVKVMGRH KPENIVIEMA  780
RENQTTQKGQ KNSRERMKRI EEGIKELGSQ ILKEHPVENT QLQNEKLYLY YLQNGRDMYV  840
DQELDINRLS DYDVDHIVPQ SFLKDDSIDN KVLTRSDKAR GKSDNVPSEE VVKKMKNYWR  900
QLLNAKLITQ RKFDNLTKAE RGGLSELDKA GFIKRQLVET RQITKHVAQI LDSRMNTKYD  960
ENDKLIREVK VITLKSKLVS DFRKDFQFYK VREINNYHHA HDAYLNAVVG TALIKKYPKL  1020
ESEFVYGDYK VYDVRKMIAK SEQEIGKATA KYFFYSNIMN FFKTEITLAN GEIRKRPLIE  1080
TNGETGEIVW DKGRDFATVR KVLSMPQVNI VKKTEVQTGG FSKESILPKR NSDKLIARKK  1140
DWDPKKYGGF DSPTVAYSVL VVAKVEKGKS KKLKSVKELL GITIMERSSF EKNPIDFLEA  1200
KGYKEVKKDL IIKLPKYSLF ELENGRKRML ASAGELQKGN ELALPSKYVN FLYLASHYEK  1260
LKGSPEDNEQ KQLFVEQHKH YLDEIIEQIS EFSKRVILAD ANLDKVLSAY NKHRDKPIRE  1320
QAENIIHLFT LTNLGAPAAF KYFDTTIDRK RYTSTKEVLD ATLIHQSITG LYETRIDLSQ  1380
LGGDSAGGGG SGGGGSGGGG SGPKKKRKVA AAGSGRADAL DDFDLDMLGS DALDDFDLDM  1440
LGSDALDDFD LDMLGSDALD DFDLDMLINC T                                1471

SEQ ID NO: 2           moltype = AA  length = 1384
FEATURE                Location/Qualifiers
REGION                 1..1384
                       note = Synthetic
source                 1..1384
                       mol_type = protein
                       organism = synthetic construct
SEQUENCE: 2
MKRPAATKKA GQAKKKKDKK YSIGLAIGTN SVGWAVITDE YKVPSKKFKV LGNTDRHSIK  60
KNLIGALLFD SGETAEATRL KRTARRRYTR RKNRICYLQE IFSNEMAKVD DSFFHRLEES  120
FLVEEDKKHE RHPIFGNIVD EVAYHEKYPT IYHLRKKLVD STDKADLRLI YLALAHMIKF  180
RGHFLIEGDL NPDNSDVDKL FIQLVQTYNQ LFEENPINAS GVDAKAILSA RLSKSRRLEN  240
LIAQLPGEKK NGLFGNLIAL SLGLTPNFKS NFDLAEDAKL QLSKDTYDDD LDNLLAQIGD  300
QYADLFLAAK NLSDAILLSD ILRVNTEITK APLSASMIKR YDEHHQDLTL LKALVRQQLP  360
EKYKEIFFDQ SKNGYAGYID GGASQEEFYK FIKPILEKMD GTEELLVKLN REDLLRKQRT  420
FDNGSIPHQI HLGELHAILR RQEDFYPFLK DNREKIEKIL TFRIPYYVGP LARGNSRFAW  480
MTRKSEETIT PWNFEEVVDK GASAQSFIER MTNFDKNLPN EKVLPKHSLL YEYFTVYNEL  540
TKVKYVTEGM RKPAFLSGEQ KKAIVDLLFK TNRKVTVKQL KEDYFKKIEC FDSVEISGVE  600
DRFNASLGTY HDLLKIIKDK DFLDNEENED ILEDIVLTLT LFEDREMIEE RLKTYAHLFD  660
DKVMKQLKRR RYTGWGRLSR KLINGIRDKQ SGKTILDFLK SDGFANRNFM QLIHDDSLTF  720
KEDIQKAQVS GQGDSLHEHI ANLAGSPAIK KGILQTVKVV DELVKVMGRH KPENIVIEMA  780
RENQTTQKGQ KNSRERMKRI EEGIKELGSQ ILKEHPVENT QLQNEKLYLY YLQNGRDMYV  840
DQELDINRLS DYDVDHIVPQ SFLKDDSIDN KVLTRSDKAR GKSDNVPSEE VVKKMKNYWR  900
QLLNAKLITQ RKFDNLTKAE RGGLSELDKA GFIKRQLVET RQITKHVAQI LDSRMNTKYD  960
ENDKLIREVK VITLKSKLVS DFRKDFQFYK VREINNYHHA HDAYLNAVVG TALIKKYPKL  1020
ESEFVYGDYK VYDVRKMIAK SEQEIGKATA KYFFYSNIMN FFKTEITLAN GEIRKRPLIE  1080
TNGETGEIVW DKGRDFATVR KVLSMPQVNI VKKTEVQTGG FSKESILPKR NSDKLIARKK  1140
DWDPKKYGGF DSPTVAYSVL VVAKVEKGKS KKLKSVKELL GITIMERSSF EKNPIDFLEA  1200
KGYKEVKKDL IIKLPKYSLF ELENGRKRML ASAGELQKGN ELALPSKYVN FLYLASHYEK  1260
LKGSPEDNEQ KQLFVEQHKH YLDEIIEQIS EFSKRVILAD ANLDKVLSAY NKHRDKPIRE  1320
QAENIIHLFT LTNLGAPAAF KYFDTTIDRK RYTSTKEVLD ATLIHQSITG LYETRIDLSQ  1380
LGGD                                                              1384

SEQ ID NO: 3           moltype = AA  length = 62
FEATURE                Location/Qualifiers
REGION                 1..62
                       note = Synthetic
source                 1..62
                       mol_type = protein
                       organism = synthetic construct
SEQUENCE: 3
AAAGSGRADA LDDFDLDMLG SDALDDFDLD MLGSDALDDF DLDMLGSDAL DDFDLDMLIN  60
CT                                                                62

SEQ ID NO: 4           moltype = AA  length = 4
FEATURE                Location/Qualifiers
REGION                 1..4
                       note = Synthetic
source                 1..4
                       mol_type = protein
                       organism = synthetic construct
SEQUENCE: 4
GGGS                                                              4

SEQ ID NO: 5           moltype = AA  length = 5
FEATURE                Location/Qualifiers
REGION                 1..5
                       note = Synthetic
```

```
source                  1..5
                        mol_type = protein
                        organism = synthetic construct
SEQUENCE: 5
GGGGS                                                                       5

SEQ ID NO: 6            moltype = AA  length = 473
FEATURE                 Location/Qualifiers
REGION                  1..473
                        note = Synthetic
source                  1..473
                        mol_type = protein
                        organism = synthetic construct
SEQUENCE: 6
MASNFTQFVL VDNGGTGDVT VAPSNFANGV AEWISSNSRS QAYKVTCSVR QSSAQKRKYT  60
IKVEVPKVAT QTVGGVELPV AAWRSYLNME LTIPIFATNS DCELIVKAMQ GLLKDGNPIP  120
SAIAANSGIY SAGGGGSGGG GSGGGGSGPK KKRKVAAAGS PSGQISNQAL ALAPSSAPVL  180
AQTMVPSSAM VPLAQPPAPA PVLTPGPPQS LSAPVPKSTQ AGEGTLSEAL LHLQFDADED  240
LGALLGNSTD PGVFTDLASV DNSEFQQLLN QGVSMSHSTA EPMLMEYPEA ITRLVTGSQR  300
PPDPAPTPLG TSGLPNGLSG DEDFSSIADM DFSALLSQIS SSGQGGGGSG FSVDTSALLD  360
LFSPSVTVPD MSLPDLDSSL ASIQELLSPQ EPPRPPEAEN SSPDSGKQLV HYTAQPLFLL  420
DPGSVDTGSN DLPVLFELGE GSYFSEGDGF AEDPTISLLT GSEPPKAKDP TVS         473

SEQ ID NO: 7            moltype = AA  length = 130
FEATURE                 Location/Qualifiers
REGION                  1..130
                        note = Synthetic
source                  1..130
                        mol_type = protein
                        organism = synthetic construct
SEQUENCE: 7
MASNFTQFVL VDNGGTGDVT VAPSNFANGV AEWISSNSRS QAYKVTCSVR QSSAQKRKYT  60
IKVEVPKVAT QTVGGVELPV AAWRSYLNME LTIPIFATNS DCELIVKAMQ GLLKDGNPIP  120
SAIAANSGIY                                                          130

SEQ ID NO: 8            moltype = AA  length = 181
FEATURE                 Location/Qualifiers
REGION                  1..181
                        note = Synthetic
source                  1..181
                        mol_type = protein
                        organism = synthetic construct
SEQUENCE: 8
PSGQISNQAL ALAPSSAPVL AQTMVPSSAM VPLAQPPAPA PVLTPGPPQS LSAPVPKSTQ  60
AGEGTLSEAL LHLQFDADED LGALLGNSTD PGVFTDLASV DNSEFQQLLN QGVSMSHSTA  120
EPMLMEYPEA ITRLVTGSQR PPDPAPTPLG TSGLPNGLSG DEDFSSIADM DFSALLSQIS  180
S                                                                   181

SEQ ID NO: 9            moltype = AA  length = 124
FEATURE                 Location/Qualifiers
REGION                  1..124
                        note = Synthetic
source                  1..124
                        mol_type = protein
                        organism = synthetic construct
SEQUENCE: 9
GFSVDTSALL DLFSPSVTVP DMSLPDLDSS LASIQELLSP QEPPRPPEAE NSSPDSGKQL  60
VHYTAQPLFL LDPGSVDTGS NDLPVLFELG EGSYFSEGDG FAEDPTISLL TGSEPPKAKD  120
PTVS                                                                124

SEQ ID NO: 10           moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 10
gttttagagc tatgct                                                   16

SEQ ID NO: 11           moltype = RNA  length = 67
FEATURE                 Location/Qualifiers
misc_feature            1..67
                        note = Synthetic
source                  1..67
                        mol_type = other RNA
                        organism = synthetic construct
```

```
SEQUENCE: 11
agcatagcaa gttaaaataa ggctagtccg ttatcaactt gaaaaagtgg caccgagtcg  60
gtgcttt                                                            67

SEQ ID NO: 12          moltype = RNA  length = 77
FEATURE                Location/Qualifiers
misc_feature           1..77
                       note = Synthetic
source                 1..77
                       mol_type = other RNA
                       organism = synthetic construct
SEQUENCE: 12
gttttagagc tagaaatagc aagttaaaat aaggctagtc cgttatcaac ttgaaaaagt  60
ggcaccgagt cggtgct                                                 77

SEQ ID NO: 13          moltype = RNA  length = 82
FEATURE                Location/Qualifiers
misc_feature           1..82
                       note = Synthetic
source                 1..82
                       mol_type = other RNA
                       organism = synthetic construct
SEQUENCE: 13
gttggaacca ttcaaaacag catagcaagt taaaataagg ctagtccgtt atcaacttga  60
aaaagtggca ccgagtcggt gc                                           82

SEQ ID NO: 14          moltype = RNA  length = 76
FEATURE                Location/Qualifiers
misc_feature           1..76
                       note = Synthetic
source                 1..76
                       mol_type = other RNA
                       organism = synthetic construct
SEQUENCE: 14
gttttagagc tagaaatagc aagttaaaat aaggctagtc cgttatcaac ttgaaaaagt  60
ggcaccgagt cggtgc                                                  76

SEQ ID NO: 15          moltype = RNA  length = 86
FEATURE                Location/Qualifiers
misc_feature           1..86
                       note = Synthetic
source                 1..86
                       mol_type = other RNA
                       organism = synthetic construct
SEQUENCE: 15
gtttaagagc tatgctggaa acagcatagc aagtttaaat aaggctagtc cgttatcaac  60
ttgaaaaagt ggcaccgagt cggtgc                                       86

SEQ ID NO: 16          moltype = RNA  length = 34
FEATURE                Location/Qualifiers
misc_feature           1..34
                       note = Synthetic
source                 1..34
                       mol_type = other RNA
                       organism = synthetic construct
SEQUENCE: 16
ggccaacatg aggatcaccc atgtctgcag ggcc                              34

SEQ ID NO: 17          moltype =   length =
SEQUENCE: 17
000

SEQ ID NO: 18          moltype =   length =
SEQUENCE: 18
000

SEQ ID NO: 19          moltype =   length =
SEQUENCE: 19
000

SEQ ID NO: 20          moltype = AA  length = 18
FEATURE                Location/Qualifiers
REGION                 1..18
                       note = Synthetic
source                 1..18
                       mol_type = protein
                       organism = synthetic construct
SEQUENCE: 20
EGRGSLLTCG DVEENPGP                                                18
```

```
SEQ ID NO: 21          moltype = AA  length = 19
FEATURE                Location/Qualifiers
REGION                 1..19
                       note = Synthetic
source                 1..19
                       mol_type = protein
                       organism = synthetic construct
SEQUENCE: 21
ATNFSLLKQA GDVEENPGP                                              19

SEQ ID NO: 22          moltype = AA  length = 20
FEATURE                Location/Qualifiers
REGION                 1..20
                       note = Synthetic
source                 1..20
                       mol_type = protein
                       organism = synthetic construct
SEQUENCE: 22
QCTNYALLKL AGDVESNPGP                                             20

SEQ ID NO: 23          moltype = AA  length = 22
FEATURE                Location/Qualifiers
REGION                 1..22
                       note = Synthetic
source                 1..22
                       mol_type = protein
                       organism = synthetic construct
SEQUENCE: 23
VKQTLNFDLL KLAGDVESNP GP                                          22

SEQ ID NO: 24          moltype = DNA  length = 4152
FEATURE                Location/Qualifiers
misc_feature           1..4152
                       note = Synthetic
source                 1..4152
                       mol_type = other DNA
                       organism = synthetic construct
SEQUENCE: 24
atgaaaaggc cggcggccac gaaaaaggcc ggccaggcaa aaaagaaaaa ggacaagaag  60
tacagcatcg gcctggccat cggcaccaac tctgtgggct gggccgtgat caccgacgag  120
tacaaggtgc ccagcaagaa attcaaggtg ctgggcaaca ccgaccggca cagcatcaag  180
aagaacctga tcggagccct gctgttcgac agcggcgaaa cagccgaggc cacccggctg  240
aagagaaccg ccagaagaag atacaccaga cggaagaacc ggatctgcta tctgcaagag  300
atcttcagca acgagatggc caaggtggac gacagcttct tccacagact ggaagagtcc  360
ttcctggtgg aagaggataa gaagcacgag cggcacccca tcttcggcaa catcgtggac  420
gaggtggcct accacgagaa gtaccccacc atctaccacc tgagaaagaa actggtggac  480
agcaccgaca aggccgacct gcggctgatc tatctggccc tggcccacat gatcaagttc  540
cggggccact tcctgatcga gggcgacctg aaccccgaca acagcgacgt ggacaagctg  600
ttcatccagc tggtgcagac ctacaaccag ctgttcgagg aaaaccccat caacgccagc  660
ggcgtggacg ccaaggccat cctgtctgcc agactgagca agagcagacg gctggaaaat  720
ctgatcgccc agctgcccgg cgagaagaag aatggcctgt tcggcaacct gattgccctg  780
agcctgggcc tgacccccaa cttcaagagc aacttcgacc tggccgagga tgccaaactg  840
cagctgagca aggacaccta cgacgacgac ctggacaacc tgctggccca gatcggcgac  900
cagtacgccg acctgtttct ggccgccaag aacctgtccg acgccatcct gctgagcgac  960
atcctgagag tgaacaccga gatcaccaag gcccccctga gcgcctctat gatcaagaga  1020
tacgacgagc accaccagga cctgaccctg ctgaaagctc tcgtgcggca gcagctgcct  1080
gagaagtaca aagagatttt cttcgaccag agcaagaacg gctacgccgg ctacattgac  1140
ggcggagcca gccaggaaga gttctacaag ttcatcaagc ccatcctgga aaagatggac  1200
ggcaccgagg aactgctcgt gaagctgaac agagaggacc tgctgcggaa gcagcggacc  1260
ttcgacaacg gcagcatccc ccaccagatc cacctgggag agctgcacgc cattctgcgg  1320
cggcaggaag atttttaccc attcctgaag gacaaccggg aaaagatcga gaagatcctg  1380
accttccgca tcccctacta cgtgggccct ctggccaggg gaaacagcag attcgcctgg  1440
atgaccagaa agagcgagga aaccatcacc ccctggaact tcgaggaagt ggtggacaag  1500
ggcgcttccg cccagagctt catcgagcgg atgaccaact tcgataagaa cctgcccaac  1560
gagaaggtgc tgcccaagca cagcctgctg tacgagtact tcaccgtgta taacgagctg  1620
accaaagtga aatacgtgac cgagggaatg agaaagcccg ccttcctgag cggcgagcag  1680
aaaaaggcca tcgtggacct gctgttcaag accaaccgga aagtgaccgt gaagcagctg  1740
aaagaggact acttcaagaa aatcgagtgc ttcgactccg tggaaatctc cggcgtggaa  1800
gatcggttca acgcctccct gggcacatac cacgatctgc tgaaaattat caaggacaag  1860
gacttcctgg acaatgagga aaacgaggac attctggaag atatcgtgct gaccctgaca  1920
ctgtttgagg acagagagat gatcgaggaa cggctgaaaa cctatgccca cctgttcgac  1980
gacaaagtga tgaagcagct gaagcggcgg agatacaccg gctggggcag gctgagccgg  2040
aagctgatca acggcatccg ggacaagcag tccggcaaga caatcctgga tttcctgaag  2100
tccgacggct tcgccaacag aaacttcatg cagctgatcc acgacgacag cctgaccttt  2160
aaagaggaca tccagaaagc ccaggtgtcc ggccagggcg atagcctgca cgagcacatt  2220
gccaatctgg ccggcagccc cgccattaag aagggcatcc tgcagacagt gaaggtggtg  2280
gacgagctcg tgaaagtgat gggccggcac aagcccgaga acatcgtgat cgaaatggcc  2340
agagagaacc agaccaccca gaagggacag aagaacagcc gcgagagaat gaagcggatc  2400
```

```
gaagagggca tcaaagagct gggcagccag atcctgaaag aacaccccgt ggaaaacacc  2460
cagctgcaga acgagaagct gtacctgtac tacctgcaga atgggcggga tatgtacgtg  2520
gaccaggaac tggacatcaa ccggctgtcc gactacgatg tggaccacat cgtgcctcag  2580
agctttctga aggacgactc catcgacaac aaggtgctga ccagaagcga caaggcccgg  2640
ggcaagagcg acaacgtgcc ctccgaagag gtcgtgaaga agatgaagaa ctactggcgg  2700
cagctgctga acgccaagct gattacccag agaaagttcg acaatctgac caaggccgag  2760
agaggcggcc tgagcgaact ggataaggcc ggcttcatca agagacagct ggtggaaacc  2820
cggcagatca caaagcacgt ggcacagatc ctggactccc ggatgaacac taagtacgac  2880
gagaatgaca agctgatccg ggaagtgaaa gtgatcaccc tgaagtccaa gctggtgtcc  2940
gatttccgga aggatttcca gttttacaaa gtgcgcgaga tcaacaacta ccaccacgcc  3000
cacgacgcct acctgaacgc cgtcgtggga accgccctga tcaaaaagta ccctaagctg  3060
gaaagcgagt tcgtgtacgg cgactacaag gtgtacgacg tgcggaagat gatcgccaag  3120
agcgagcagg aaatcggcaa ggctaccgcc aagtacttct tctacagcaa catcatgaac  3180
tttttcaaga ccgagattac cctggccaac ggcgagatcc ggaagcggcc tctgatcgag  3240
acaaacggcg aaaccgggga gatcgtgtgg gataagggcc gggattttgc caccgtgcgg  3300
aaagtgctga gcatgcccca agtgaatatc gtgaaaaaga ccgaggtgca gacaggcggc  3360
ttcagcaaag agtctatcct gcccaagagg aacagcgata agctgatcgc cagaaagaag  3420
gactgggacc ctaagaagta cggcggcttc gacagcccca ccgtggccta ttctgtgctg  3480
gtggtggcca aagtggaaaa gggcaagtcc aagaaactga agagtgtgaa agagctgctg  3540
gggatcacca tcatggaaag aagcagcttc gagaagaatc ccatcgactt tctggaagcc  3600
aagggctaca aagaagtgaa aaaggacctg atcatcaagc tgcctaagta ctccctgttc  3660
gagctggaaa acggccggaa gagaatgctg gcctctgccg gcgaactgca gaagggaaac  3720
gaactggccc tgccctccaa atatgtgaac ttcctgtacc tggccagcca ctatgagaag  3780
ctgaagggct cccccgagga taatgagcag aaacagctgt ttgtggaaca gcacaagcac  3840
tacctggacg agatcatcga gcagatcagc gagttctcca agagagtgat cctggccgac  3900
gctaatctgg acaaagtgct gtccgcctac aacaagcacc gggataagcc catcagagag  3960
caggccgaga atatcatcca cctgtttacc ctgaccaatc tgggagcccc tgccgccttc  4020
aagtactttg acaccaccat cgaccggaag aggtacacca gcaccaaaga ggtgctggac  4080
gccaccctga tccaccagag catcaccggc ctgtacgaga cacggatcga cctgtctcag  4140
ctgggaggcg ac                                                      4152

SEQ ID NO: 25          moltype = DNA  length = 4414
FEATURE                Location/Qualifiers
misc_feature           1..4414
                       note = Synthetic
source                 1..4414
                       mol_type = other DNA
                       organism = synthetic construct
SEQUENCE: 25
atgaaaaggc cggcggccac gaaaaaggcc ggccaggcaa aaaagaaaaa ggacaagaag  60
tacagcatcg gcctggccat cggcaccaac tctgtgggct gggccgtgat caccgacgag  120
tacaaggtgc ccagcaagaa attcaaggtg ctgggcaaca ccgaccggca cagcatcaag  180
aagaacctga tcggagccct gctgttcgac agcggcgaaa cagccgaggc cacccggctg  240
aagagaaccg ccagaagaag atacaccaga cggaagaacc ggatctgcta tctgcaagag  300
atcttcagca acgagatggc caaggtggac gacagcttct tccacagact ggaagagtcc  360
ttcctggtgg aagaggataa gaagcacgag cggcacccca tcttcggcaa catcgtggac  420
gaggtggcct accacgagaa gtaccccacc atctaccacc tgagaaagaa actggtggac  480
agcaccgaca aggccgacct gcggctgatc tatctggccc tggcccacat gatcaagttc  540
cggggccact tcctgatcga gggcgacctg aaccccgaca acagcgacgt ggacaagctg  600
ttcatccagc tggtgcagac ctacaaccag ctgttcgagg aaaaccccat caacgccagc  660
ggcgtggacg ccaaggccat cctgtctgcc agactgagca agagcagacg gctggaaaat  720
ctgatcgccc agctgcccgg cgagaagaag aatggcctgt tcggcaacct gattgccctg  780
agcctgggcc tgacccccaa cttcaagagc aacttcgacc tggccgagga tgccaaactg  840
cagctgagca aggacaccta cgacgacgac ctggacaacc tgctggccca gatcggcgac  900
cagtacgccg acctgtttct ggccgccaag aacctgtccg acgccatcct gctgagcgac  960
atcctgagag tgaacaccga gatcaccaag gccccctga gcgcctctat gatcaagaga  1020
tacgacgagc accaccagga cctgaccctg ctgaaagctc tcgtgcggca gcagctgcct  1080
gagaagtaca aagagatttt cttcgaccag agcaagaacg gctacgccgg ctacattgac  1140
ggcggagcca gccaggaaga gttctacaag ttcatcaagc ccatcctgga aaagatggac  1200
ggcaccgagg aactgctcgt gaagctgaac agagaggacc tgctgcggaa gcagcggacc  1260
ttcgacaacg gcagcatccc ccaccagatc cacctgggag agctgcacgc cattctgcgg  1320
cggcaggaag atttttaccc attcctgaag gacaaccggg aaaagatcga gaagatcctg  1380
accttccgca tcccctacta cgtgggccct ctggccaggg gaaacagcag attcgcctgg  1440
atgaccagaa agagcgagga aaccatcacc ccctggaact tcgaggaagt ggtggacaag  1500
ggcgcttccg cccagagctt catcgagcgg atgaccaact tcgataagaa cctgcccaac  1560
gagaaggtgc tgcccaagca cagcctgctg tacgagtact tcaccgtgta taacgagctg  1620
accaaagtga aatacgtgac cgagggaatg agaaagcccg ccttcctgag cggcgagcag  1680
aaaaaggcca tcgtggacct gctgttcaag accaaccgga aagtgaccgt gaagcagctg  1740
aaagaggact acttcaagaa aatcgagtgc ttcgactccg tggaaatctc cggcgtggaa  1800
gatcggttca acgcctccct gggcacatac cacgatctgc tgaaaattat caaggacaag  1860
gacttcctgg acaatgagga aaacgaggac attctggaag atatcgtgct gaccctgaca  1920
ctgtttgagg acagagagat gatcgaggaa cggctgaaaa cctatgccca cctgttcgac  1980
gacaaagtga tgaagcagct gaagcggcgg agatacaccg gctggggcag gctgagccgg  2040
aagctgatca acggcatccg ggacaagcag tccggcaaga caatcctgga tttcctgaag  2100
tccgacggct tcgccaacag aaacttcatg cagctgatcc acgacgacag cctgaccttt  2160
aaagaggaca tccagaaagc ccaggtgtcc ggccagggcg atagcctgca cgagcacatt  2220
gccaatctgg ccggcagccc cgccattaag aagggcatcc tgcagacagt gaaggtggtg  2280
gacgagctcg tgaaagtgat gggccggcac aagcccgaga acatcgtgat cgaaatggcc  2340
agagagaacc agaccaccca gaagggacag aagaacagcc gcgagagaat gaagcggatc  2400
```

gaagagggca tcaaagagct gggcagccag atcctgaaag aacaccccgt ggaaaacacc 2460
cagctgcaga acgagaagct gtacctgtac tacctgcaga atgggcggga tatgtacgtg 2520
gaccaggaac tggacatcaa ccggctgtcc gactacgatg tggaccacat cgtgcctcag 2580
agctttctga aggacgactc catcgacaac aaggtgctga ccagaagcga caaggcccgg 2640
ggcaagagcg acaacgtgcc ctccgaagag gtcgtgaaga agatgaagaa ctactggcgg 2700
cagctgctga acgccaagct gattacccag agaaagttcg acaatctgac caaggccgag 2760
agaggcggcc tgagcgaact ggataaggcc ggcttcatca agagacagct ggtggaaacc 2820
cggcagatca caaagcacgt ggcacagatc ctggactccc ggatgaacac taagtacgac 2880
gagaatgaca agctgatccg ggaagtgaaa gtgatcaccc tgaagtccaa gctggtgtcc 2940
gatttccgga aggatttcca gttttacaaa gtgcgcgaga tcaacaacta ccaccacgcc 3000
cacgacgcct acctgaacgc cgtcgtggga accgccctga tcaaaaagta ccctaagctg 3060
gaaagcgagt tcgtgtacgg cgactacaag gtgtacgacg tgcggaagat gatcgccaag 3120
agcgagcagg aaatcggcaa ggctaccgcc aagtacttct tctacagcaa catcatgaac 3180
tttttcaaga ccgagattac cctggccaac ggcgagatcc ggaagcggcc tctgatcgag 3240
acaaacggcg aaaccgggga gatcgtgtgg gataagggcc gggattttgc caccgtgcgg 3300
aaagtgctga gcatgcccca agtgaatatc gtgaaaaaga ccgaggtgca gacaggcggc 3360
ttcagcaaag agtctatcct gcccaagagg aacagcgata agctgatcgc cagaaagaag 3420
gactgggacc ctaagaagta cggcggcttc gacagcccca ccgtggccta ttctgtgctg 3480
gtggtggcca aagtggaaaa gggcaagtcc aagaaactga agagtgtgaa agagctgctg 3540
gggatcacca tcatggaaag aagcagcttc gagaagaatc ccatcgactt tctggaagcc 3600
aagggctaca aagaagtgaa aaaggacctg atcatcaagc tgcctaagta ctccctgttc 3660
gagctggaaa acggccggaa gagaatgctg gcctctgccg gcgaactgca gaagggaaac 3720
gaactggccc tgccctccaa atatgtgaac ttcctgtacc tggccagcca ctatgagaag 3780
ctgaagggct cccccgagga taatgagcag aaacagctgt ttgtggaaca gcacaagcac 3840
tacctggacg agatcatcga gcagatcagc gagttctcca agagagtgat cctggccgac 3900
gctaatctgg acaaagtgct gtccgcctac aacaagcacc gggataagcc catcagagag 3960
caggccgaga atatcatcca cctgtttacc ctgaccaatc tgggagcccc tgccgccttc 4020
aagtactttg acaccaccat cgaccggaag aggtacacca gcaccaaaga ggtgctggac 4080
gccaccctga tccaccagag catcaccggc ctgtacgaga cacggatcga cctgtctcag 4140
ctgggaggcg acagcgctgg aggaggtgga agcggaggag gaggaagcgg aggaggaggt 4200
agcggaccta agaaaaagag gaaggtggcg gccgctggat ccggacgggc tgacgcattg 4260
gacgattttg atctggatat gctgggaagt gacgccctcg atgattttga ccttgacatg 4320
cttggttcgg atgcccttga tgactttgac ctcgacatgc tcggcagtga cgcccttgat 4380
gatttcgacc tggacatgct gattaactgt acag 4414

SEQ ID NO: 26 moltype = DNA length = 390
FEATURE Location/Qualifiers
misc_feature 1..390
note = Synthetic
source 1..390
mol_type = other DNA
organism = synthetic construct
SEQUENCE: 26
atggcttcaa actttactca gttcgtgctc gtggacaatg gtgggacagg ggatgtgaca 60
gtggctcctt ctaatttcgc taatggggtg gcagagtgga tcagctccaa ctcacggagc 120
caggcctaca aggtgacatg cagcgtcagg cagtctagtg cccagaagag aaagtatacc 180
atcaaggtgg aggtccccaa agtggctacc cagacagtgg gcggagtcga actgcctgtc 240
gccgcttgga ggtcctacct gaacatggag ctcactatcc caattttcgc taccaattct 300
gactgtgaac tcatcgtgaa ggcaatgcag gggctcctca aagacggtaa tcctatccct 360
tccgccatcg ccgctaactc aggtatctac 390

SEQ ID NO: 27 moltype = DNA length = 1419
FEATURE Location/Qualifiers
misc_feature 1..1419
note = Synthetic
source 1..1419
mol_type = other DNA
organism = synthetic construct
SEQUENCE: 27
atggcttcaa actttactca gttcgtgctc gtggacaatg gtgggacagg ggatgtgaca 60
gtggctcctt ctaatttcgc taatggggtg gcagagtgga tcagctccaa ctcacggagc 120
caggcctaca aggtgacatg cagcgtcagg cagtctagtg cccagaagag aaagtatacc 180
atcaaggtgg aggtccccaa agtggctacc cagacagtgg gcggagtcga actgcctgtc 240
gccgcttgga ggtcctacct gaacatggag ctcactatcc caattttcgc taccaattct 300
gactgtgaac tcatcgtgaa ggcaatgcag gggctcctca aagacggtaa tcctatccct 360
tccgccatcg ccgctaactc aggtatctac agcgctggag gaggtggaag cggaggagga 420
ggaagcggag gaggaggtag cggacctaag aaaaagagga aggtggcggc cgctggatcc 480
ccttcagggc agatcagcaa ccaggccctg gctctggccc ctagctccgc tccagtgctg 540
gcccagacta tggtgccctc tagtgctatg gtgcctctgg cccagccacc tgctccagcc 600
cctgtgctga ccccaggacc accccagtca ctgagcgctc cagtgcccaa gtctacacag 660
gccggcgagg ggactctgag tgaagctctg ctgcacctgc agttcgacgc tgatgaggac 720
ctgggagctc tgctggggaa cagcaccgat cccggagtgt tcacagatct ggcctccgtg 780
gacaactctg agtttcagca gctgctgaat cagggcgtgt ccatgtctca tagtacagcc 840
gaaccaatgc tgatggagta ccccgaagcc attacccggc tggtgaccgg cagccagcgg 900
ccccccgacc ccgctccaac tcccctggga accagcggcc tgcctaatgg gctgtccgga 960
gatgaagact tctcaagcat cgctgatatg gactttagtg ccctgctgtc acagatttcc 1020
tctagtgggc agggaggagg tggaagcggc ttcagcgtgg acaccagtgc cctgctggac 1080
ctgttcagcc cctcggtgac cgtgcccgac atgagcctgc ctgaccttga cagcagcctg 1140
gccagtatcc aagagctcct gtctccccag gagcccccca ggcctcccga ggcagagaac 1200

```
agcagcccgg attcagggaa gcagctggtg cactacacag cgcagccgct gttcctgctg  1260
gaccccggct ccgtggacac cgggagcaac gacctgccgg tgctgtttga gctgggagag  1320
ggctcctact tctccgaagg ggacggcttc gccgaggacc ccaccatctc cctgctgaca  1380
ggctcggagc ctcccaaagc caaggacccc actgtctcc                          1419

SEQ ID NO: 28          moltype = DNA  length = 187
FEATURE                Location/Qualifiers
misc_feature           1..187
                       note = Synthetic
source                 1..187
                       mol_type = other DNA
                       organism = synthetic construct
SEQUENCE: 28
gcggccgctg gatccggacg ggctgacgca ttggacgatt ttgatctgga tatgctggga  60
agtgacgccc tcgatgattt tgaccttgac atgcttggtt cggatgccct tgatgacttt  120
gacctcgaca tgctcggcag tgacgccctt gatgatttcg acctggacat gctgattaac  180
tgtacag                                                            187

SEQ ID NO: 29          moltype = DNA  length = 543
FEATURE                Location/Qualifiers
misc_feature           1..543
                       note = Synthetic
source                 1..543
                       mol_type = other DNA
                       organism = synthetic construct
SEQUENCE: 29
ccttcagggc agatcagcaa ccaggccctg gctctggccc ctagctccgc tccagtgctg  60
gcccagacta tggtgccctc tagtgctatg gtgcctctgg cccagccacc tgctccagcc  120
cctgtgctga ccccaggacc accccagtca ctgagcgctc cagtgcccaa gtctacacag  180
gccggcgagg ggactctgag tgaagctctg ctgcacctgc agttcgacgc tgatgaggac  240
ctgggagctc tgctggggaa cagcaccgat cccggagtgt tcacagatct ggcctccgtg  300
gacaactctg agtttcagca gctgctgaat cagggcgtgt ccatgtctca tagtacagcc  360
gaaccaatgc tgatggagta ccccgaagcc attacccggc tggtgaccgg cagccagcgg  420
ccccccgacc ccgctccaac tcccctggga accagcggcc tgcctaatgg gctgtccgga  480
gatgaagact tctcaagcat cgctgatatg gactttagtg ccctgctgtc acagatttcc  540
tct                                                                543

SEQ ID NO: 30          moltype = DNA  length = 372
FEATURE                Location/Qualifiers
misc_feature           1..372
                       note = Synthetic
source                 1..372
                       mol_type = other DNA
                       organism = synthetic construct
SEQUENCE: 30
ggcttcagcg tggacaccag tgccctgctg gacctgttca gcccctcggt gaccgtgccc  60
gacatgagcc tgcctgacct tgacagcagc ctggccagta tccaagagct cctgtctccc  120
caggagcccc ccaggcctcc cgaggcagag aacagcagcc cggattcagg gaagcagctg  180
gtgcactaca cagcgcagcc gctgttcctg ctggaccccg gctccgtgga caccgggagc  240
aacgacctgc cggtgctgtt tgagctggga gagggctcct acttctccga aggggacggc  300
ttcgccgagg accccaccat ctccctgctg acaggctcgg agcctcccaa agccaaggac  360
cccactgtct cc                                                      372

SEQ ID NO: 31          moltype = DNA  length = 9043
FEATURE                Location/Qualifiers
misc_feature           1..9043
                       note = Synthetic
misc_feature           1..34
                       note = First loxP site
misc_feature           125..928
                       note = Sequence encoding neomycin phosphotransferase for
                        resistance to neomycin family antibiotics
misc_feature           937..2190
                       note = Polyadenylation signal
misc_feature           2218..2251
                       note = Second loxP site
misc_feature           2306..6457
                       note = Codon-optimized dCas9 coding sequence
misc_feature           2309..2356
                       note = First NLS
misc_feature           6512..6532
                       note = Second NLS
misc_feature           6533..6719
                       note = VP64
misc_feature           6719..6781
                       note = T2A with 5' GSG
misc_feature           6782..7171
                       note = MCP
```

```
misc_feature           7226..7246
                       note = Third NLS
misc_feature           7262..7804
                       note = p65
misc_feature           7829..8200
                       note = HSF1
misc_feature           8224..8820
                       note = Woodchuck hepatitis virus posttranscriptional
                        regulatory element (WPRE)
source                 1..9043
                       mol_type = other DNA
                       organism = synthetic construct
SEQUENCE: 31
ataacttcgt ataatgtatg ctatacgaag ttattaggtc cctcgacctg caggaattgt  60
tgacaattaa tcatcggcat agtatatcgg catagtataa tacgacaagg tgaggaacta  120
aaccatggga tcggccattg aacaagatgg attgcacgca ggttctccgg ccgcttgggt  180
ggagaggcta ttcggctatg actgggcaca acagacaatc ggctgctctg atgccgccgt  240
gttccggctg tcagcgcagg ggcgcccggt tctttttgtc aagaccgacc tgtccggtgc  300
cctgaatgaa ctgcaggacg aggcagcgcg gctatcgtgg ctggccacga cgggcgttcc  360
ttgcgcagct gtgctcgacg ttgtcactga agcgggaagg gactggctgc tattgggcga  420
agtgccgggg caggatctcc tgtcatctca ccttgctcct gccgagaaag tatccatcat  480
ggctgatgca atgcggcggc tgcatacgct tgatccggct acctgcccat tcgaccacca  540
agcgaaacat cgcatcgagc gagcacgtac tcggatggaa gccggtcttg tcgatcagga  600
tgatctggac gaagagcatc aggggctcgc gccagccgaa ctgttcgcca ggctcaaggc  660
gcgcatgccc gacggcgatg atctcgtcgt gacccatggc gatgcctgct tgccgaatat  720
catggtggaa aatggccgct tttctggatt catcgactgt ggccggctgg gtgtggcgga  780
ccgctatcag gacatagcgt tggctacccg tgatattgct gaagagcttg gcggcgaatg  840
ggctgaccgc ttcctcgtgc tttacggtat cgccgctccc gattcgcagc gcatcgcctt  900
ctatcgcctt cttgacgagt tcttctgagg ggatccgctg taagtctgca gaaattgatg  960
atctattaaa caataaagat gtccactaaa atggaagttt ttcctgtcat actttgttaa  1020
gaagggtgag aacagagtac ctacattttg aatggaagga ttggagctac gggggtgggg  1080
gtggggtggg attagataaa tgcctgctct ttactgaagg ctctttacta ttgctttatg  1140
ataatgtttc atagttggat atcataattt aaacaagcaa aaccaaatta agggccagct  1200
cattcctccc actcatgatc tatagatcta tagatctctc gtgggatcat tgtttttctc  1260
ttgattccca ctttgtggtt ctaagtactg tggtttccaa atgtgtcagt ttcatagcct  1320
gaagaacgag atcagcagcc tctgttccac atacacttca ttctcagtat tgttttgcca  1380
agttctaatt ccatcagaag cttgcagatc tgcgactcta gaggatctgc gactctagag  1440
gatcataatc agccatacca catttgtaga ggttttactt gctttaaaaa acctcccaca  1500
cctccccctg aacctgaaac ataaaatgaa tgcaattgtt gttgttaact tgtttattgc  1560
agcttataat ggttacaaat aaagcaatag catcacaaat ttcacaaata aagcattttt  1620
ttcactgcat tctagttgtg gtttgtccaa actcatcaat gtatcttatc atgtctggat  1680
ctgcgactct agaggatcat aatcagccat accacatttg tagaggtttt acttgcttta  1740
aaaaacctcc cacacctccc cctgaacctg aaacataaaa tgaatgcaat tgttgttgtt  1800
aacttgttta ttgcagctta taatggttac aaataaagca atagcatcac aaatttcaca  1860
aataaagcat ttttttcact gcattctagt tgtggtttgt ccaaactcat caatgtatct  1920
tatcatgtct ggatctgcga ctctagagga tcataatcag ccataccaca tttgtagagg  1980
ttttacttgc tttaaaaaac ctcccacacc tccccctgaa cctgaaacat aaaatgaatg  2040
caattgttgt tgttaacttg tttattgcag cttataatgg ttacaaataa agcaatagca  2100
tcacaaattt cacaaataaa gcattttttt cactgcattc tagttgtggt ttgtccaaac  2160
tcatcaatgt atcttatcat gtctggatcc ccatcaagct gatccggaac ccttaatata  2220
acttcgtata atgtatgcta tacgaagtta ttaggtccct cgacctgcag cccaagctag  2280
tgcccgggaa ttcgctaggg ccaccatgaa aaggccggcg gccacgaaaa aggccggcca  2340
ggcaaaaaag aaaaaggaca agaagtacag catcggcctg gccatcggca ccaactctgt  2400
gggctgggcc gtgatcaccg acgagtacaa ggtgcccagc aagaaattca aggtgctggg  2460
caacaccgac cggcacagca tcaagaagaa cctgatcgga gccctgctgt tcgacagcgg  2520
cgaaacagcc gaggccaccc ggctgaagag aaccgccaga agaagataca ccagacggaa  2580
gaaccggatc tgctatctgc aagagatctt cagcaacgag atggccaagg tggacgacag  2640
cttcttccac agactggaag agtccttcct ggtggaagag gataagaagc acgagcggca  2700
ccccatcttc ggcaacatcg tggacgaggt ggcctaccac gagaagtacc ccaccatcta  2760
ccacctgaga aagaaactgg tggacagcac cgacaaggcc gacctgcggc tgatctatct  2820
ggccctggcc cacatgatca agttccgggg ccacttcctg atcgagggcg acctgaaccc  2880
cgacaacagc gacgtggaca agctgttcat ccagctggtg cagacctaca accagctgtt  2940
cgaggaaaac cccatcaacg ccagcggcgt ggacgccaag gccatcctgt ctgccagact  3000
gagcaagagc agacggctgg aaaatctgat cgcccagctg cccggcgaga agaagaatgg  3060
cctgttcggc aacctgattg ccctgagcct gggcctgacc cccaacttca agagcaactt  3120
cgacctggcc gaggatgcca aactgcagct gagcaaggac acctacgacg acgacctgga  3180
caacctgctg gcccagatcg gcgaccagta cgccgacctg tttctggccg ccaagaacct  3240
gtccgacgcc atcctgctga gcgacatcct gagagtgaac accgagatca ccaaggcccc  3300
cctgagcgcc tctatgatca agagatacga cgagcaccac caggacctga ccctgctgaa  3360
agctctcgtg cggcagcagc tgcctgagaa gtacaaagag attttcttcg accagagcaa  3420
gaacggctac gccggctaca ttgacggcgg agccagccag gaagagttct acaagttcat  3480
caagcccatc ctggaaaaga tggacggcac cgaggaactg ctcgtgaagc tgaacagaga  3540
ggacctgctg cggaagcagc ggaccttcga caacggcagc atcccccacc agatccacct  3600
gggagagctg cacgccattc tgcggcggca ggaagatttt tacccattcc tgaaggacaa  3660
ccgggaaaag atcgagaaga tcctgacctt ccgcatcccc tactacgtgg gccctctggc  3720
caggggaaac agcagattcg cctggatgac cagaaagagc gaggaaacca tcaccccctg  3780
gaacttcgag gaagtggtgg acaagggcgc ttccgcccag agcttcatcg agcggatgac  3840
caacttcgat aagaacctgc ccaacgagaa ggtgctgccc aagcacagcc tgctgtacga  3900
gtacttcacc gtgtataacg agctgaccaa agtgaaatac gtgaccgagg gaatgagaaa  3960
```

-continued

```
gcccgccttc ctgagcggcg agcagaaaaa ggccatcgtg gacctgctgt tcaagaccaa  4020
ccggaaagtg accgtgaagc agctgaaaga ggactacttc aagaaaatcg agtgcttcga  4080
ctccgtggaa atctccggcg tggaagatcg gttcaacgcc tccctgggca cataccacga  4140
tctgctgaaa attatcaagg acaaggactt cctggacaat gaggaaaacg aggacattct  4200
ggaagatatc gtgctgaccc tgacactgtt tgaggacaga gagatgatcg aggaacggct  4260
gaaaacctat gcccacctgt tcgacgacaa agtgatgaag cagctgaagc ggcggagata  4320
caccggctgg ggcaggctga gccggaagct gatcaacggc atccgggaca agcagtccgg  4380
caagacaatc ctggatttcc tgaagtccga cggcttcgcc aacagaaact tcatgcagct  4440
gatccacgac gacagcctga cctttaaaga ggacatccag aaagcccagg tgtccggcca  4500
gggcgatagc ctgcacgagc acattgccaa tctggccggc agccccgcca ttaagaaggg  4560
catcctgcag acagtgaagg tggtggacga gctcgtgaaa gtgatgggcc ggcacaagcc  4620
cgagaacatc gtgatcgaaa tggccagaga gaaccagacc acccagaagg gacagaagaa  4680
cagccgcgag agaatgaagc ggatcgaaga gggcatcaaa gagctgggca gccagatcct  4740
gaaagaacac cccgtggaaa acacccagct gcagaacgag aagctgtacc tgtactacct  4800
gcagaatggg cgggatatgt acgtggacca ggaactggac atcaaccggc tgtccgacta  4860
cgatgtggac cacatcgtgc ctcagagctt tctgaaggac gactccatcg acaacaaggt  4920
gctgaccaga agcgacaagg cccggggcaa gagcgacaac gtgccctccg aagaggtcgt  4980
gaagaagatg aagaactact ggcggcagct gctgaacgcc aagctgatta cccagagaaa  5040
gttcgacaat ctgaccaagg ccgagagagg cggcctgagc gaactggata aggccggctt  5100
catcaagaga cagctggtgg aaacccggca gatcacaaag cacgtggcac agatcctgga  5160
ctcccggatg aacactaagt acgacgagaa tgacaagctg atccgggaag tgaaagtgat  5220
caccctgaag tccaagctgg tgtccgattt ccggaaggat ttccagtttt acaaagtgcg  5280
cgagatcaac aactaccacc acgcccacga cgcctacctg aacgccgtcg tgggaaccgc  5340
cctgatcaaa aagtacccta agctggaaag cgagttcgtg tacggcgact acaaggtgta  5400
cgacgtgcgg aagatgatcg ccaagagcga gcaggaaatc ggcaaggcta ccgccaagta  5460
cttcttctac agcaacatca tgaacttttt caagaccgag attaccctgg ccaacggcga  5520
gatccggaag cggcctctga tcgagacaaa cggcgaaacc ggggagatcg tgtgggataa  5580
gggccgggat tttgccaccg tgcggaaagt gctgagcatg ccccaagtga atatcgtgaa  5640
aaagaccgag gtgcagacag gcggcttcag caaagagtct atcctgccca agaggaacag  5700
cgataagctg atcgccagaa agaaggactg ggaccctaag aagtacggcg gcttcgacag  5760
ccccaccgtg gcctattctg tgctggtggt ggccaaagtg gaaaagggca agtccaagaa  5820
actgaagagt gtgaaagagc tgctggggat caccatcatg gaaagaagca gcttcgagaa  5880
gaatcccatc gactttctgg aagccaaggg ctacaaagaa gtgaaaaagg acctgatcat  5940
caagctgcct aagtactccc tgttcgagct ggaaaacggc cggaagagaa tgctggcctc  6000
tgccggcgaa ctgcagaagg gaaacgaact ggccctgccc tccaaatatg tgaacttcct  6060
gtacctggcc agccactatg agaagctgaa gggctccccc gaggataatg agcagaaaca  6120
gctgtttgtg gaacagcaca agcactacct ggacgagatc atcgagcaga tcagcgagtt  6180
ctccaagaga gtgatcctgg ccgacgctaa tctggacaaa gtgctgtccg cctacaacaa  6240
gcaccgggat aagcccatca gagagcaggc cgagaatatc atccacctgt ttaccctgac  6300
caatctggga gcccctgccg ccttcaagta ctttgacacc accatcgacc ggaagaggta  6360
caccagcacc aaagaggtgc tggacgccac cctgatccac cagagcatca ccggcctgta  6420
cgagacacgg atcgacctgt ctcagctggg aggcgacagc gctggaggag gtggaagcgg  6480
aggaggagga agcggaggag gaggtagcgg acctaagaaa aagaggaagg tggcggccgc  6540
tggatccgga cgggctgacg cattggacga ttttgatctg gatatgctgg gaagtgacgc  6600
cctcgatgat tttgaccttg acatgcttgg ttcggatgcc cttgatgact ttgacctcga  6660
catgctcggc agtgacgccc ttgatgattt cgacctggac atgctgatta actgtacagg  6720
cagtggagag ggcagaggaa gtctgctaac atgcggtgac gtcgaggaga atcctggccc  6780
aatggcttca aactttactc agttcgtgct cgtggacaat ggtgggacag gggatgtgac  6840
agtggctcct tctaatttcg ctaatggggt ggcagagtgg atcagctcca actcacggag  6900
ccaggcctac aaggtgacat gcagcgtcag gcagtctagt gcccagaaga gaaagtatac  6960
catcaaggtg gaggtcccca aagtggctac ccagacagtg ggcggagtcg aactgcctgt  7020
cgccgcttgg aggtcctacc tgaacatgga gctcactatc ccaattttcg ctaccaattc  7080
tgactgtgaa ctcatcgtga aggcaatgca ggggctcctc aaagacggta atcctatccc  7140
ttccgccatc gccgctaact caggtatcta cagcgctgga ggaggtggaa gcggaggagg  7200
aggaagcgga ggaggaggta gcggacctaa gaaaaagagg aaggtggcgg ccgctggatc  7260
cccttcaggg cagatcagca accaggccct ggctctggcc cctagctccg ctccagtgct  7320
ggcccagact atggtgccct ctagtgctat ggtgcctctg gcccagccac ctgctccagc  7380
ccctgtgctg accccaggac caccccagtc actgagcgct ccagtgccca agtctacaca  7440
ggccggcgag gggactctga gtgaagctct gctgcacctg cagttcgacg ctgatgagga  7500
cctgggagct ctgctgggga acagcaccga tcccggagtg ttcacagatc tggcctccgt  7560
ggacaactct gagtttcagc agctgctgaa tcagggcgtg tccatgtctc atagtacagc  7620
cgaaccaatg ctgatggagt accccgaagc cattacccgg ctggtgaccg gcagccagcg  7680
gccccccgac cccgctccaa ctcccctggg aaccagcggc ctgcctaatg ggctgtccgg  7740
agatgaagac ttctcaagca tcgctgatat ggactttagt gccctgctgt cacagatttc  7800
ctctagtggg cagggaggag gtggaagcgg cttcagcgtg gacaccagtg ccctgctgga  7860
cctgttcagc ccctcggtga ccgtgcccga catgagcctg cctgaccttg acagcagcct  7920
ggccagtatc caagagctcc tgtctcccca ggagcccccc aggcctcccg aggcagagaa  7980
cagcagcccg gattcaggga agcagctggt gcactacaca gcgcagccgc tgttcctgct  8040
ggaccccggc tccgtggaca ccgggagcaa cgacctgccg gtgctgtttg agctgggaga  8100
gggctcctac ttctccgaag gggacggctt cgccgaggac cccaccatct ccctgctgac  8160
aggctcggag cctcccaaag ccaaggaccc cactgtctcc tgagaattcg atatcaagct  8220
tatcgataat caacctctgg attacaaaat ttgtgaaaga ttgactggta ttcttaacta  8280
tgttgctcct tttacgctat gtggatacgc tgctttaatg cctttgtatc atgctattgc  8340
ttcccgtatg gctttcattt tctcctcctt gtataaatcc tggttgctgt ctctttatga  8400
ggagttgtgg cccgttgtca ggcaacgtgg cgtggtgtgc actgtgtttg ctgacgcaac  8460
ccccactggt tggggcattg ccaccacctg tcagctcctt tccgggactt tcgctttccc  8520
cctccctatt gccacggcgg aactcatcgc cgcctgcctt gcccgctgct ggacaggggc  8580
tcggctgttg ggcactgaca attccgtggt gttgtcgggg aaatcatcgt cctttccttg  8640
gctgctcgcc tgtgttgcca cctggattct gcgcgggacg tccttctgct acgtcccttc  8700
```

```
ggccctcaat ccagcggacc ttccttcccg cggcctgctg ccggctctgc ggcctcttcc  8760
gcgtcttcgc cttcgccctc agacgagtcg gatctccctt tgggccgcct ccccgcatcg  8820
ataccgtcga cctcgacctc gactgtgcct tctagttgcc agccatctgt tgtttgcccc  8880
tcccccgtgc cttccttgac cctggaaggt gccactccca ctgtcctttc ctaataaaat  8940
gaggaaattg catcgcattg tctgagtagg tgtcattcta ttctgggggg tggggtgggg  9000
caggacagca agggggagga ttgggaagac aatggcaggc atg                    9043

SEQ ID NO: 32          moltype = DNA  length = 3812
FEATURE                Location/Qualifiers
misc_feature           1..3812
                       note = Synthetic
misc_feature           1..32
                       note = First rox site
misc_feature           111..710
                       note = Sequence encoding puromycin-N-acetyltransferase for
                        resistance to puromycin family antibiotics
misc_feature           797..2338
                       note = Polyadenylation signal
misc_feature           2363..2394
                       note = Second rox site
misc_feature           2401..2640
                       note = First U6 promoter
misc_feature           2641..2797
                       note = First guide RNA coding sequence
misc_difference        2641..2660
                       note = n = A, T, C, or G
misc_feature           2883..3122
                       note = Second U6 promoter
misc_feature           3123..3279
                       note = Second guide RNA coding sequence
misc_difference        3123..3142
                       note = n = A, T, C, or G
misc_feature           3364..3603
                       note = Third U6 promoter
misc_feature           3604..3760
                       note = Third guide RNA coding sequence
misc_difference        3604..3623
                       note = n = A, T, C, or G
source                 1..3812
                       mol_type = other DNA
                       organism = synthetic construct
SEQUENCE: 32
taactttaaa taatgccaat tatttaaagt tacctgcagg acgtgttgac aattaatcat  60
cggcatagta tatcggcata gtataatacg acaaggtgag gaactaaacc atgaccgagt  120
acaagcccac ggtgcgcctc gccacccgcg acgacgtccc cagggccgta cgcaccctcg  180
ccgccgcgtt cgccgactac cccgccacgc gccacaccgt cgatccggac cgccacatcg  240
agcgggtcac cgagctgcaa gaactcttcc tcacgcgcgt cgggctcgac atcggcaagg  300
tgtgggtcgc ggacgacggc gccgcggtgg cggtctggac cacgccggag agcgtcgaag  360
cgggggcggt gttcgccgag atcggcccgc gcatggccga gttgagcggt tcccggctgg  420
ccgcgcagca acagatggaa ggcctcctgg cgccgcaccg gcccaaggag cccgcgtggt  480
tcctggccac cgtcggcgtc tcgcccgacc accagggcaa gggtctgggc agcgccgtcg  540
tgctccccgg agtggaggcg gccgagcgcg ccggggtgcc cgccttcctg gagacctccg  600
cgccccgcaa cctccccttc tacgagcggc tcggcttcac cgtcaccgcc gacgtcgagg  660
tgcccgaagg accgcgcacc tggtgcatga cccgcaagcc cggtgcctga cgcccgcccc  720
acgacccgca gcgcccgacc gaaaggagcg cacgacccca tgcatcgatg atctagagct  780
cgctgatcag cctcgactgt gccttctagt tgccagccat ctgttgtttg cccctccccc  840
gtgccttcct tgaccctgga aggtgccact cccactgtcc tttcctaata aaatgaggaa  900
attgcatcgc attgtctgag taggtgtcat tctattctgg ggggtggggt ggggcaggac  960
agcaaggggg aggattggga agacaatagc aggcatgctg gggatgcggt gggctctatg  1020
gcataacttc gtataatgta tgctatacgg gggatccgct gtaagtctgc agaaattgat  1080
gatctattaa acaataaaga tgtccactaa aatggaagtt tttcctgtca tactttgtta  1140
agaagggtga gaacagagta cctacatttt gaatggaagg attggagcta cgggggtggg  1200
ggtggggtgg gattagataa atgcctgctc tttactgaag gctctttact attgctttat  1260
gataatgttt catagttgga tatcataatt taaacaagca aaaccaaatt aagggccagc  1320
tcattcctcc cactcatgat ctatagatct atagatctct cgtgggatca ttgtttttct  1380
cttgattccc actttgtggt tctaagtact gtggtttcca aatgtgtcag tttcatagcc  1440
tgaagaacga gatcagcagc ctctgttcca catacacttc attctcagta ttgttttgcc  1500
aagttctaat tccatcagac ctcgacctgc agccgacgct aggtcgtcag tcaaagtacg  1560
tacctcaggt gcaggctgcc tatcagaagg tggtggctgg tgtggccaat gccctggctc  1620
acaaatacca ctgagatctt tttccctctg ccaaaaatta tggggacatc atgaagcccc  1680
ttgagcatct gacttctggc taataaagga aatttatttt cattgcaata gtgtgttgga  1740
attttttgtg tctctcactc ggaaggacat atgggagggc aaatcattta aaacatcaga  1800
atgagtattt ggtttagagt ttggcaacat atgcccatat gctggctgcc atgaacaaag  1860
gttggctata aagaggtcat cagtatatga aacagccccc tgctgtccat tccttattcc  1920
atagaaaagc cttgacttga ggttagattt tttttatatt ttgttttgtg ttattttttt  1980
ctttaacatc cctaaaattt tccttagatg ttttactagc cagatttttc ctcctctcct  2040
gactactccc agtcatagct gtccctcttc tcttatggag atccctcgag gacatgaggt  2100
cgtcgctgta atcagccata ccacatttgt agaggtttta cttgctttaa aaaacctccc  2160
acacctcccc ctgaacctga aacataaaat gaatgcaatt gttgttgtta acttgtttat  2220
```

```
tgcagcttat aatggttaca aataaagcaa tagcatcaca aatttcacaa ataaagcatt  2280
tttttcactg cattctagtt gtggtttgtc caaactcatc aatgtatctt atcatgtcga  2340
cactgggtcg tgatcgggta cctaacttta aataatgcca attatttaaa gttagctagc  2400
tttcccatga ttccttcata tttgcatata cgatacaagg ctgttagaga gataattgga  2460
attaatttga ctgtaaacac aaagatatta gtacaaaata cgtgacgtag aaagtaataa  2520
tttcttgggt agtttgcagt tttaaaatta tgttttaaaa tggactatca tatgcttacc  2580
gtaacttgaa agtatttcga tttcttggct ttatatatct tgtggaaagg acgaaacacc  2640
nnnnnnnnnn nnnnnnnnnn gttttagagc taggccaaca tgaggatcac ccatgtctgc  2700
agggcctagc aagttaaaat aaggctagtc cgttatcaac ttggccaaca tgaggatcac  2760
ccatgtctgc agggccaagt ggcaccgagt cggtgctttt tttgttttag agctagaaat  2820
agcaagttaa aataaggcta gtccgttttg agctccataa gactcggcct tagaacaagc  2880
tttttcccat gattccttca tatttgcata tacgatacaa ggctgttaga gagataattg  2940
gaattaattt gactgtaaac acaaagatat tagtacaaaa tacgtgacgt agaaagtaat  3000
aatttcttgg gtagtttgca gttttaaaat tatgttttaa aatggactat catatgctta  3060
ccgtaacttg aaagtatttc gatttcttgg ctttatatat cttgtggaaa ggacgaaaca  3120
ccnnnnnnnn nnnnnnnnnn nngttttaga gctaggccaa catgaggatc acccatgtct  3180
gcagggccta gcaagttaaa ataaggctag tccgttatca acttggccaa catgaggatc  3240
acccatgtct gcagggccaa gtggcaccga gtcggtgctt tttttgtttt agagctagaa  3300
atagcaagtt aaaataaggc tagtccgttt tatgcatgtg gctcccattt atacctggcc  3360
ggctttccca tgattccttc atatttgcat atacgataca aggctgttag agagataatt  3420
ggaattaatt tgactgtaaa cacaaagata ttagtacaaa atacgtgacg tagaaagtaa  3480
taatttcttg ggtagtttgc agttttaaaa ttatgtttta aaatggacta tcatatgctt  3540
accgtaactt gaaagtattt cgatttcttg gctttatata tcttgtggaa aggacgaaac  3600
accnnnnnnn nnnnnnnnnn nnngttttag agctaggcca acatgaggat cacccatgtc  3660
tgcagggcct agcaagttaa aataaggcta gtccgttatc aacttggcca acatgaggat  3720
cacccatgtc tgcagggcca agtggcaccg agtcggtgct ttttttgttt tagagctaga  3780
aatagcaagt taaaataagg ctagtccgtt tt                                3812
```

```
SEQ ID NO: 33          moltype = DNA  length = 3814
FEATURE                Location/Qualifiers
misc_feature           1..3814
                       note = Synthetic
misc_feature           1..32
                       note = First rox site
misc_feature           111..710
                       note = Sequence encoding puromycin-N-acetyltransferase for
                        resistance to puromycin family antibiotics
misc_feature           797..2338
                       note = Polyadenylation signal
misc_feature           2363..2394
                       note = Second rox site
misc_feature           2401..2640
                       note = First U6 promoter
misc_feature           2642..2798
                       note = First Ttr guide RNA coding sequence
misc_feature           2884..3123
                       note = Second U6 promoter
misc_feature           3125..3281
                       note = Second Ttr guide RNA coding sequence
misc_feature           3366..3605
                       note = Third U6 promoter
misc_feature           3606..3762
                       note = Third Ttr guide RNA coding sequence
source                 1..3814
                       mol_type = other DNA
                       organism = synthetic construct
SEQUENCE: 33
taactttaaa taatgccaat tatttaaagt tacctgcagg acgtgttgac aattaatcat  60
cggcatagta tatcggcata gtataatacg acaaggtgag gaactaaacc atgaccgagt  120
acaagcccac ggtgcgcctc gccacccgcg acgacgtccc cagggccgta cgcaccctcg  180
ccgccgcgtt cgccgactac cccgccacgc gccacaccgt cgatccggac cgccacatcg  240
agcgggtcac cgagctgcaa gaactcttcc tcacgcgcgt cgggctcgac atcggcaagg  300
tgtgggtcgc ggacgacggc gccgcggtgg cggtctggac cacgccggag agcgtcgaag  360
cgggggcggt gttcgccgag atcggcccgc gcatggccga gttgagcggt tcccggctgg  420
ccgcgcagca acagatggaa ggcctcctgg cgccgcaccg gcccaaggag cccgcgtggt  480
tcctggccac cgtcggcgtc tcgcccgacc accagggcaa gggtctgggc agcgccgtcg  540
tgctccccgg agtggaggcg gccgagcgcg ccggggtgcc cgccttcctg gagacctccg  600
cgccccgcaa cctccccttc tacgagcggc tcggcttcac cgtcaccgcc gacgtcgagg  660
tgcccgaagg accgcgcacc tggtgcatga cccgcaagcc cggtgcctga cgcccgcccc  720
acgacccgca gcgcccgacc gaaaggagcg cacgacccca tgcatcgatg atctagagct  780
cgctgatcag cctcgactgt gccttctagt tgccagccat ctgttgtttg cccctccccc  840
gtgccttcct tgaccctgga aggtgccact cccactgtcc tttcctaata aaatgaggaa  900
attgcatcgc attgtctgag taggtgtcat tctattctgg ggggtggggt ggggcaggac  960
agcaaggggg aggattggga agacaatagc aggcatgctg gggatgcggt gggctctatg  1020
gcataacttc gtataatgta tgctatacgg gggatccgct gtaagtctgc agaaattgat  1080
gatctattaa acaataaaga tgtccactaa aatggaagtt tttcctgtca tactttgtta  1140
agaagggtga gaacagagta cctacatttt gaatggaagg attggagcta cgggggtggg  1200
ggtggggtgg gattagataa atgcctgctc tttactgaag gctctttact attgctttat  1260
gataatgttt catagttgga tatcataatt taaacaagca aaaccaaatt aagggccagc  1320
```

```
tcattcctcc cactcatgat ctatagatct atagatctct cgtgggatca ttgtttttct  1380
cttgattccc actttgtggt tctaagtact gtggtttcca aatgtgtcag tttcatagcc  1440
tgaagaacga gatcagcagc ctctgttcca catacacttc attctcagta ttgttttgcc  1500
aagttctaat tccatcagac ctcgacctgc agccgacgct aggtcgtcag tcaaagtacg  1560
tacctcaggt gcaggctgcc tatcagaagg tggtggctgg tgtggccaat gccctggctc  1620
acaaatacca ctgagatctt tttccctctg ccaaaaatta tggggacatc atgaagcccc  1680
ttgagcatct gacttctggc taataaagga aatttatttt cattgcaata gtgtgttgga  1740
attttttgtg tctctcactc ggaaggacat atgggagggc aaatcattta aaacatcaga  1800
atgagtattt ggtttagagt ttggcaacat atgcccatat gctggctgcc atgaacaaag  1860
gttggctata aagaggtcat cagtatatga aacagccccc tgctgtccat tccttattcc  1920
atagaaaagc cttgacttga ggttagattt tttttatatt ttgttttgtg ttattttttt  1980
ctttaacatc cctaaaattt tccttagatg ttttactagc cagatttttc ctcctctcct  2040
gactactccc agtcatagct gtccctcttc tcttatggag atccctcgag gacatgaggt  2100
cgtcgctgta atcagccata ccacatttgt agaggtttta cttgctttaa aaaacctccc  2160
acacctcccc ctgaacctga aacataaaat gaatgcaatt gttgttgtta acttgtttat  2220
tgcagcttat aatggttaca aataaagcaa tagcatcaca aatttcacaa ataaagcatt  2280
tttttcactg cattctagtt gtggtttgtc caaactcatc aatgtatctt atcatgtcga  2340
cactgggtcg tgatcgggta cctaacttta aataatgcca attatttaaa gttagctagc  2400
tttcccatga ttccttcata tttgcatata cgatacaagg ctgttagaga gataattgga  2460
attaatttga ctgtaaacac aaagatatta gtacaaaata cgtgacgtag aaagtaataa  2520
tttcttgggt agtttgcagt tttaaaatta tgttttaaaa tggactatca tatgcttacc  2580
gtaacttgaa agtatttcga tttcttggct ttatatatct tgtggaaagg acgaaacacc  2640
gacggttgcc ctctttccca agttttagag ctaggccaac atgaggatca cccatgtctg  2700
cagggcctag caagttaaaa taaggctagt ccgttatcaa cttggccaac atgaggatca  2760
cccatgtctg cagggccaag tggcaccgag tcggtgcttt ttttgtttta gagctagaaa  2820
tagcaagtta aaataaggct agtccgtttt gagctccata agactcggcc ttagaacaag  2880
ctttttccca tgattccttc atatttgcat atacgataca aggctgttag agagataatt  2940
ggaattaatt tgactgtaaa cacaaagata ttagtacaaa atacgtgacg tagaaagtaa  3000
taatttcttg ggtagtttgc agttttaaaa ttatgtttta aaatggacta tcatatgctt  3060
accgtaactt gaaagtattt cgatttcttg gctttatata tcttgtggaa aggacgaaac  3120
accgactgtc agactcaaag gtgcgtttta gagctaggcc aacatgagga tcacccatgt  3180
ctgcagggcc tagcaagtta aaataaggct agtccgttat caacttggcc aacatgagga  3240
tcacccatgt ctgcagggcc aagtggcacc gagtcggtgc ttttttttgtt ttagagctag  3300
aaatagcaag ttaaaataag gctagtccgt tttatgcatg tggctcccat ttatacctgg  3360
ccggctttcc catgattcct tcatatttgc atatacgata caaggctgtt agagagataa  3420
ttggaattaa tttgactgta aacacaaaga tattagtaca aaatacgtga cgtagaaagt  3480
aataatttct tgggtagttt gcagttttaa aattatgttt taaaatggac tatcatatgc  3540
ttaccgtaac ttgaaagtat ttcgatttct tggctttata tatcttgtgg aaaggacgaa  3600
acaccgacaa taagtagtct tactcgtttt agagctaggc caacatgagg atcacccatg  3660
tctgcagggc ctagcaagtt aaaataaggc tagtccgtta tcaacttggc caacatgagg  3720
atcacccatg tctgcagggc caagtggcac cgagtcggtg cttttttttgt tttagagcta  3780
gaaatagcaa gttaaaataa ggctagtccg tttt                              3814
```

```
SEQ ID NO: 34          moltype = DNA  length = 20
FEATURE                Location/Qualifiers
source                 1..20
                       mol_type = other DNA
                       organism = Mus musculus
SEQUENCE: 34
acggttgccc tctttcccaa                                              20

SEQ ID NO: 35          moltype = DNA  length = 20
FEATURE                Location/Qualifiers
source                 1..20
                       mol_type = other DNA
                       organism = Mus musculus
SEQUENCE: 35
actgtcagac tcaaaggtgc                                              20

SEQ ID NO: 36          moltype = DNA  length = 20
FEATURE                Location/Qualifiers
source                 1..20
                       mol_type = other DNA
                       organism = Mus musculus
SEQUENCE: 36
gacaataagt agtcttactc                                              20

SEQ ID NO: 37          moltype = RNA  length = 157
FEATURE                Location/Qualifiers
misc_feature           1..157
                       note = Synthetic
source                 1..157
                       mol_type = other RNA
                       organism = synthetic construct
SEQUENCE: 37
acggttgccc tctttcccaa gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                          157
```

```
SEQ ID NO: 38          moltype = RNA  length = 157
FEATURE                Location/Qualifiers
misc_feature           1..157
                       note = Synthetic
source                 1..157
                       mol_type = other RNA
                       organism = synthetic construct
SEQUENCE: 38
actgtcagac tcaaaggtgc gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 39          moltype = RNA  length = 157
FEATURE                Location/Qualifiers
misc_feature           1..157
                       note = Synthetic
source                 1..157
                       mol_type = other RNA
                       organism = synthetic construct
SEQUENCE: 39
gacaataagt agtcttactc gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 40          moltype = RNA  length = 137
FEATURE                Location/Qualifiers
misc_feature           1..137
                       note = Synthetic
source                 1..137
                       mol_type = other RNA
                       organism = synthetic construct
SEQUENCE: 40
gttttagagc taggccaaca tgaggatcac ccatgtctgc agggcctagc aagttaaaat  60
aaggctagtc cgttatcaac ttggccaaca tgaggatcac ccatgtctgc agggccaagt  120
ggcaccgagt cggtgct                                                 137

SEQ ID NO: 41          moltype = RNA  length = 20
FEATURE                Location/Qualifiers
misc_feature           1..20
                       note = Synthetic
source                 1..20
                       mol_type = other RNA
                       organism = synthetic construct
SEQUENCE: 41
acggttgccc tctttcccaa                                              20

SEQ ID NO: 42          moltype = RNA  length = 20
FEATURE                Location/Qualifiers
misc_feature           1..20
                       note = Synthetic
source                 1..20
                       mol_type = other RNA
                       organism = synthetic construct
SEQUENCE: 42
actgtcagac tcaaaggtgc                                              20

SEQ ID NO: 43          moltype = RNA  length = 20
FEATURE                Location/Qualifiers
misc_feature           1..20
                       note = Synthetic
source                 1..20
                       mol_type = other RNA
                       organism = synthetic construct
SEQUENCE: 43
gacaataagt agtcttactc                                              20

SEQ ID NO: 44          moltype = AA  length = 1965
FEATURE                Location/Qualifiers
REGION                 1..1965
                       note = Synthetic
source                 1..1965
                       mol_type = protein
                       organism = synthetic construct
SEQUENCE: 44
MKRPAATKKA GQAKKKKDKK YSIGLAIGTN SVGWAVITDE YKVPSKKFKV LGNTDRHSIK  60
KNLIGALLFD SGETAEATRL KRTARRRYTR RKNRICYLQE IFSNEMAKVD DSFFHRLEES  120
FLVEEDKKHE RHPIFGNIVD EVAYHEKYPT IYHLRKKLVD STDKADLRLI YLALAHMIKF  180
RGHFLIEGDL NPDNSDVDKL FIQLVQTYNQ LFEENPINAS GVDAKAILSA RLSKSRRLEN  240
LIAQLPGEKK NGLFGNLIAL SLGLTPNFKS NFDLAEDAKL QLSKDTYDDD LDNLLAQIGD  300
```

```
QYADLFLAAK NLSDAILLSD ILRVNTEITK APLSASMIKR YDEHHQDLTL LKALVRQQLP  360
EKYKEIFFDQ SKNGYAGYID GGASQEEFYK FIKPILEKMD GTEELLVKLN REDLLRKQRT  420
FDNGSIPHQI HLGELHAILR RQEDFYPFLK DNREKIEKIL TFRIPYYVGP LARGNSRFAW  480
MTRKSEETIT PWNFEEVVDK GASAQSFIER MTNFDKNLPN EKVLPKHSLL YEYFTVYNEL  540
TKVKYVTEGM RKPAFLSGEQ KKAIVDLLFK TNRKVTVKQL KEDYFKKIEC FDSVEISGVE  600
DRFNASLGTY HDLLKIIKDK DFLDNEENED ILEDIVLTLT LFEDREMIEE RLKTYAHLFD  660
DKVMKQLKRR RYTGWGRLSR KLINGIRDKQ SGKTILDFLK SDGFANRNFM QLIHDDSLTF  720
KEDIQKAQVS GQGDSLHEHI ANLAGSPAIK KGILQTVKVV DELVKVMGRH KPENIVIEMA  780
RENQTTQKGQ KNSRERMKRI EEGIKELGSQ ILKEHPVENT QLQNEKLYLY YLQNGRDMYV  840
DQELDINRLS DYDVDHIVPQ SFLKDDSIDN KVLTRSDKAR GKSDNVPSEE VVKKMKNYWR  900
QLLNAKLITQ RKFDNLTKAE RGGLSELDKA GFIKRQLVET RQITKHVAQI LDSRMNTKYD  960
ENDKLIREVK VITLKSKLVS DFRKDFQFYK VREINNYHHA HDAYLNAVVG TALIKKYPKL  1020
ESEFVYGDYK VYDVRKMIAK SEQEIGKATA KYFFYSNIMN FFKTEITLAN GEIRKRPLIE  1080
TNGETGEIVW DKGRDFATVR KVLSMPQVNI VKKTEVQTGG FSKESILPKR NSDKLIARKK  1140
DWDPKKYGGF DSPTVAYSVL VVAKVEKGKS KKLKSVKELL GITIMERSSF EKNPIDFLEA  1200
KGYKEVKKDL IIKLPKYSLF ELENGRKRML ASAGELQKGN ELALPSKYVN FLYLASHYEK  1260
LKGSPEDNEQ KQLFVEQHKH YLDEIIEQIS EFSKRVILAD ANLDKVLSAY NKHRDKPIRE  1320
QAENIIHLFT LTNLGAPAAF KYFDTTIDRK RYTSTKEVLD ATLIHQSITG LYETRIDLSQ  1380
LGGDSAGGGG SGGGGSGGGG SGPKKKRKVA AAGSGRADAL DDFDLDMLGS DALDDFDLDM  1440
LGSDALDDFD LDMLGSDALD DFDLDMLINC TGSGEGRGSL LTCGDVEENP GPMASNFTQF  1500
VLVDNGGTGD VTVAPSNFAN GVAEWISSNS RSQAYKVTCS VRQSSAQKRK YTIKVEVPKV  1560
ATQTVGGVEL PVAAWRSYLN MELTIPIFAT NSDCELIVKA MQGLLKDGNP IPSAIAANSG  1620
IYSAGGGGSG GGGSGGGGSG PKKKRKVAAA GSPSGQISNQ ALALAPSSAP VLAQTMVPSS  1680
AMVPLAQPPA PAPVLTPGPP QSLSAPVPKS TQAGEGTLSE ALLHLQFDAD EDLGALLGNS  1740
TDPGVFTDLA SVDNSEFQQL LNQGVSMSHS TAEPMLMEYP EAITRLVTGS QRPPDPAPTP  1800
LGTSGLPNGL SGDEDFSSIA DMDFSALLSQ ISSSGQGGGG SGFSVDTSAL LDLFSPSVTV  1860
PDMSLPDLDS SLASIQELLS PQEPPRPPEA ENSSPDSGKQ LVHYTAQPLF LLDPGSVDTG  1920
SNDLPVLFEL GEGSYFSEGD GFAEDPTISL LTGSEPPKAK DPTVS                  1965

SEQ ID NO: 45          moltype = DNA  length = 22
FEATURE                Location/Qualifiers
misc_feature           1..22
                       note = Synthetic
source                 1..22
                       mol_type = other DNA
                       organism = synthetic construct
SEQUENCE: 45
cgtgatctgc aactccagtc tt                                           22

SEQ ID NO: 46          moltype = DNA  length = 23
FEATURE                Location/Qualifiers
misc_feature           1..23
                       note = Synthetic
source                 1..23
                       mol_type = other DNA
                       organism = synthetic construct
SEQUENCE: 46
agatgggcgg gagtcttctg ggc                                          23

SEQ ID NO: 47          moltype = DNA  length = 23
FEATURE                Location/Qualifiers
misc_feature           1..23
                       note = Synthetic
source                 1..23
                       mol_type = other DNA
                       organism = synthetic construct
SEQUENCE: 47
cacaccaggt tagcctttaa gcc                                          23

SEQ ID NO: 48          moltype = DNA  length = 19
FEATURE                Location/Qualifiers
misc_feature           1..19
                       note = Synthetic
source                 1..19
                       mol_type = other DNA
                       organism = synthetic construct
SEQUENCE: 48
ggtggagagg ctattcggc                                               19

SEQ ID NO: 49          moltype = DNA  length = 23
FEATURE                Location/Qualifiers
misc_feature           1..23
                       note = Synthetic
source                 1..23
                       mol_type = other DNA
                       organism = synthetic construct
SEQUENCE: 49
tgggcacaac agacaatcgg ctg                                          23
```

```
SEQ ID NO: 50          moltype = DNA  length = 17
FEATURE                Location/Qualifiers
misc_feature           1..17
                       note = Synthetic
source                 1..17
                       mol_type = other DNA
                       organism = synthetic construct
SEQUENCE: 50
gaacacggcg gcatcag                                                17

SEQ ID NO: 51          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 51
accggctgtc cgactacgat                                             20

SEQ ID NO: 52          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 52
tggaccacat cgtgcctcag a                                           21

SEQ ID NO: 53          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 53
cgggccttgt cgcttctg                                               18

SEQ ID NO: 54          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 54
ggctccttct aatttcgcta atgg                                        24

SEQ ID NO: 55          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 55
tggcagagtg gatcagctcc a                                           21

SEQ ID NO: 56          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 56
ctgacgctgc atgtcacctt                                             20

SEQ ID NO: 57          moltype = DNA  length = 22
FEATURE                Location/Qualifiers
misc_feature           1..22
                       note = Synthetic
source                 1..22
                       mol_type = other DNA
                       organism = synthetic construct
SEQUENCE: 57
agggcgtgtc catgtctcat ag                                          22
```

```
SEQ ID NO: 58          moltype = DNA  length = 23
FEATURE                Location/Qualifiers
misc_feature           1..23
                       note = Synthetic
source                 1..23
                       mol_type = other DNA
                       organism = synthetic construct
SEQUENCE: 58
acagccgaac caatgctgat gga                                          23

SEQ ID NO: 59          moltype = DNA  length = 19
FEATURE                Location/Qualifiers
misc_feature           1..19
                       note = Synthetic
source                 1..19
                       mol_type = other DNA
                       organism = synthetic construct
SEQUENCE: 59
ccagccgggt aatggcttc                                               19

SEQ ID NO: 60          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 60
tgtgttgcca cctggattct g                                            21

SEQ ID NO: 61          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 61
cgcgggacgt ccttctgcta c                                            21

SEQ ID NO: 62          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 62
ggaaggtccg ctggattgag                                              20

SEQ ID NO: 63          moltype = RNA  length = 157
FEATURE                Location/Qualifiers
misc_feature           1..157
                       note = Synthetic
misc_difference        1..20
                       note = n = A, T, C, or G
source                 1..157
                       mol_type = other RNA
                       organism = synthetic construct
SEQUENCE: 63
nnnnnnnnnn nnnnnnnnnn gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 64          moltype = DNA  length = 5895
FEATURE                Location/Qualifiers
misc_feature           1..5895
                       note = Synthetic
source                 1..5895
                       mol_type = other DNA
                       organism = synthetic construct
SEQUENCE: 64
atgaaaaggc cggcggccac gaaaaaggcc ggccaggcaa aaaagaaaaa ggacaagaag  60
tacagcatcg gcctggccat cggcaccaac tctgtgggct gggccgtgat caccgacgag  120
tacaaggtgc ccagcaagaa attcaaggtg ctgggcaaca ccgaccggca cagcatcaag  180
aagaacctga tcggagccct gctgttcgac agcggcgaaa cagccgaggc cacccggctg  240
aagagaaccg ccagaagaag atacaccaga cggaagaacc ggatctgcta tctgcaagag  300
atcttcagca acgagatggc caaggtggac gacagcttct tccacagact ggaagagtcc  360
```

```
ttcctggtgg aagaggataa gaagcacgag cggcacccca tcttcggcaa catcgtggac  420
gaggtggcct accacgagaa gtaccccacc atctaccacc tgagaaagaa actggtggac  480
agcaccgaca aggccgacct gcggctgatc tatctggccc tggcccacat gatcaagttc  540
cggggccact tcctgatcga gggcgacctg aaccccgaca acagcgacgt ggacaagctg  600
ttcatccagc tggtgcagac ctacaaccag ctgttcgagg aaaaccccat caacgccagc  660
ggcgtggacg ccaaggccat cctgtctgcc agactgagca agagcagacg gctggaaaat  720
ctgatcgccc agctgcccgg cgagaagaag aatggcctgt tcggcaacct gattgccctg  780
agcctgggcc tgacccccaa cttcaagagc aacttcgacc tggccgagga tgccaaactg  840
cagctgagca aggacaccta cgacgacgac ctggacaacc tgctggccca gatcggcgac  900
cagtacgccg acctgtttct ggccgccaag aacctgtccg acgccatcct gctgagcgac  960
atcctgagag tgaacaccga gatcaccaag gccccccctga gcgcctctat gatcaagaga  1020
tacgacgagc accaccagga cctgaccctg ctgaaagctc tcgtgcggca gcagctgcct  1080
gagaagtaca aagagatttt cttcgaccag agcaagaacg gctacgccgg ctacattgac  1140
ggcggagcca gccaggaaga gttctacaag ttcatcaagc ccatcctgga aaagatggac  1200
ggcaccgagg aactgctcgt gaagctgaac agagaggacc tgctgcggaa gcagcggacc  1260
ttcgacaacg gcagcatccc ccaccagatc cacctgggag agctgcacgc cattctgcgg  1320
cggcaggaag atttttaccc attcctgaag gacaaccggg aaaagatcga gaagatcctg  1380
accttccgca tcccctacta cgtgggccct ctggccaggg gaaacagcag attcgcctgg  1440
atgaccagaa agagcgagga aaccatcacc ccctggaact tcgaggaagt ggtggacaag  1500
ggcgcttccg cccagagctt catcgagcgg atgaccaact tcgataagaa cctgcccaac  1560
gagaaggtgc tgcccaagca cagcctgctg tacgagtact tcaccgtgta taacgagctg  1620
accaaagtga aatacgtgac cgagggaatg agaaagcccg ccttcctgag cggcgagcag  1680
aaaaaggcca tcgtggacct gctgttcaag accaaccgga aagtgaccgt gaagcagctg  1740
aaagaggact acttcaagaa aatcgagtgc ttcgactccg tggaaatctc cggcgtggaa  1800
gatcggttca acgcctccct gggcacatac cacgatctgc tgaaaattat caaggacaag  1860
gacttcctgg acaatgagga aaacgaggac attctggaag atatcgtgct gaccctgaca  1920
ctgtttgagg acagagagat gatcgaggaa cggctgaaaa cctatgccca cctgttcgac  1980
gacaaagtga tgaagcagct gaagcggcgg agatacaccg gctggggcag gctgagccgg  2040
aagctgatca acggcatccg ggacaagcag tccggcaaga caatcctgga tttcctgaag  2100
tccgacggct tcgccaacag aaacttcatg cagctgatcc acgacgacag cctgaccttt  2160
aaagaggaca tccagaaagc ccaggtgtcc ggccagggcg atagcctgca cgagcacatt  2220
gccaatctgg ccggcagccc cgccattaag aagggcatcc tgcagacagt gaaggtggtg  2280
gacgagctcg tgaaagtgat gggccggcac aagcccgaga acatcgtgat cgaaatggcc  2340
agagagaacc agaccaccca gaagggacag aagaacagcc gcgagagaat gaagcggatc  2400
gaagagggca tcaaagagct gggcagccag atcctgaaag aacaccccgt ggaaaacacc  2460
cagctgcaga acgagaagct gtacctgtac tacctgcaga atgggcggga tatgtacgtg  2520
gaccaggaac tggacatcaa ccggctgtcc gactacgatg tggaccacat cgtgcctcag  2580
agctttctga aggacgactc catcgacaac aaggtgctga ccagaagcga caaggcccgg  2640
ggcaagagcg acaacgtgcc ctccgaagag gtcgtgaaga agatgaagaa ctactggcgg  2700
cagctgctga acgccaagct gattacccag agaaagttcg acaatctgac caaggccgag  2760
agaggcggcc tgagcgaact ggataaggcc ggcttcatca agagacagct ggtggaaacc  2820
cggcagatca caaagcacgt ggcacagatc ctggactccc ggatgaacac taagtacgac  2880
gagaatgaca agctgatccg ggaagtgaaa gtgatcaccc tgaagtccaa gctggtgtcc  2940
gatttccgga aggatttcca gttttacaaa gtgcgcgaga tcaacaacta ccaccacgcc  3000
cacgacgcct acctgaacgc cgtcgtggga accgccctga tcaaaaagta ccctaagctg  3060
gaaagcgagt tcgtgtacgg cgactacaag gtgtacgacg tgcggaagat gatcgccaag  3120
agcgagcagg aaatcggcaa ggctaccgcc aagtacttct tctacagcaa catcatgaac  3180
tttttcaaga ccgagattac cctggccaac ggcgagatcc ggaagcggcc tctgatcgag  3240
acaaacggcg aaaccgggga gatcgtgtgg gataagggcc gggattttgc caccgtgcgg  3300
aaagtgctga gcatgcccca agtgaatatc gtgaaaaaga ccgaggtgca gacaggcggc  3360
ttcagcaaag agtctatcct gcccaagagg aacagcgata agctgatcgc cagaaagaag  3420
gactgggacc ctaagaagta cggcggcttc gacagcccca ccgtggccta ttctgtgctg  3480
gtggtggcca aagtggaaaa gggcaagtcc aagaaactga agagtgtgaa agagctgctg  3540
gggatcacca tcatggaaag aagcagcttc gagaagaatc ccatcgactt tctggaagcc  3600
aagggctaca aagaagtgaa aaaggacctg atcatcaagc tgcctaagta ctccctgttc  3660
gagctggaaa acggccggaa gagaatgctg gcctctgccg gcgaactgca gaagggaaac  3720
gaactggccc tgccctccaa atatgtgaac ttcctgtacc tggccagcca ctatgagaag  3780
ctgaagggct cccccgagga taatgagcag aaacagctgt ttgtggaaca gcacaagcac  3840
tacctggacg agatcatcga gcagatcagc gagttctcca agagagtgat cctggccgac  3900
gctaatctgg acaaagtgct gtccgcctac aacaagcacc gggataagcc catcagagag  3960
caggccgaga atatcatcca cctgtttacc ctgaccaatc tgggagcccc tgccgccttc  4020
aagtactttg acaccaccat cgaccggaag aggtacacca gcaccaaaga ggtgctggac  4080
gccaccctga tccaccagag catcaccggc ctgtacgaga cacggatcga cctgtctcag  4140
ctgggaggcg acagcgctgg aggaggtgga agcggaggag gaggaagcgg aggaggaggt  4200
agcggaccta agaaaaagag gaaggtggcg gccgctggat ccggacgggc tgacgcattg  4260
gacgattttg atctggatat gctgggaagt gacgccctcg atgattttga ccttgacatg  4320
cttggttcgg atgcccttga tgactttgac ctcgacatgc tcggcagtga cgcccttgat  4380
gatttcgacc tggacatgct gattaactgt acaggcagtg gagagggcag aggaagtctg  4440
ctaacatgcg gtgacgtcga ggagaatcct ggcccaatgg cttcaaactt tactcagttc  4500
gtgctcgtgg acaatggtgg gacaggggat gtgacagtgg ctccttctaa tttcgctaat  4560
ggggtggcag agtggatcag ctccaactca cggagccagg cctacaaggt gacatgcagc  4620
gtcaggcagt ctagtgccca gaagagaaag tataccatca aggtggaggt ccccaaagtg  4680
gctacccaga cagtgggcgg agtcgaactg cctgtcgccg cttggaggtc ctacctgaac  4740
atggagctca ctatcccaat tttcgctacc aattctgact gtgaactcat cgtgaaggca  4800
atgcaggggc tcctcaaaga cggtaatcct atcccttccg ccatcgccgc taactcaggt  4860
atctacagcg ctggaggagg tggaagcgga ggaggaggaa gcggaggagg aggtagcgga  4920
cctaagaaaa agaggaaggt ggcggccgct ggatcccctt cagggcagat cagcaaccag  4980
gccctggctc tggcccctag ctccgctcca gtgctggccc agactatggt gccctctagt  5040
gctatggtgc ctctggccca gccacctgct ccagcccctg tgctgacccc aggaccaccc  5100
```

```
cagtcactga gcgctccagt gcccaagtct acacaggccg gcgaggggac tctgagtgaa  5160
gctctgctgc acctgcagtt cgacgctgat gaggacctgg gagctctgct ggggaacagc  5220
accgatcccg gagtgttcac agatctggcc tccgtggaca actctgagtt tcagcagctg  5280
ctgaatcagg gcgtgtccat gtctcatagt acagccgaac caatgctgat ggagtacccc  5340
gaagccatta cccggctggt gaccggcagc cagcggcccc ccgaccccgc tccaactccc  5400
ctgggaacca gcggcctgcc taatgggctg tccggagatg aagacttctc aagcatcgct  5460
gatatggact ttagtgccct gctgtcacag atttcctcta gtgggcaggg aggaggtgga  5520
agcggcttca gcgtggacac cagtgccctg ctggacctgt tcagcccctc ggtgaccgtg  5580
cccgacatga gcctgcctga ccttgacagc agcctggcca gtatccaaga gctcctgtct  5640
ccccaggagc cccccaggcc tcccgaggca gagaacagca gcccggattc agggaagcag  5700
ctggtgcact acacagcgca gccgctgttc ctgctggacc ccggctccgt ggacaccggg  5760
agcaacgacc tgccggtgct gtttgagctg ggagagggct cctacttctc cgaaggggac  5820
ggcttcgccg aggaccccac catctccctg ctgacaggct cggagcctcc caaagccaag  5880
gaccccactg tctcc                                                   5895
```

```
SEQ ID NO: 65          moltype = DNA  length = 1412
FEATURE                Location/Qualifiers
misc_feature           1..1412
                       note = Synthetic
source                 1..1412
                       mol_type = other DNA
                       organism = synthetic construct
misc_difference        241..260
                       note = n = A, T, C, or G
misc_difference        723..742
                       note = n = A, T, C, or G
misc_difference        1204..1223
                       note = n = A, T, C, or G
SEQUENCE: 65
tttcccatga ttccttcata tttgcatata cgatacaagg ctgttagaga gataattgga  60
attaatttga ctgtaaacac aaagatatta gtacaaaata cgtgacgtag aaagtaataa  120
tttcttgggt agtttgcagt tttaaaatta tgttttaaaa tggactatca tatgcttacc  180
gtaacttgaa agtatttcga tttcttggct ttatatatct tgtggaaagg acgaaacacc  240
nnnnnnnnnn nnnnnnnnnn gttttagagc taggccaaca tgaggatcac ccatgtctgc  300
agggcctagc aagttaaaat aaggctagtc cgttatcaac ttggccaaca tgaggatcac  360
ccatgtctgc agggccaagt ggcaccgagt cggtgctttt tttgttttag agctagaaat  420
agcaagttaa aataaggcta gtccgttttg agctccataa gactcggcct tagaacaagc  480
tttttcccat gattccttca tatttgcata tacgatacaa ggctgttaga gagataattg  540
gaattaattt gactgtaaac acaaagatat tagtacaaaa tacgtgacgt agaaagtaat  600
aatttcttgg gtagtttgca gttttaaaat tatgttttaa aatggactat catatgctta  660
ccgtaacttg aaagtatttc gatttcttgg ctttatatat cttgtggaaa ggacgaaaca  720
ccnnnnnnnn nnnnnnnnnn nngttttaga gctaggccaa catgaggatc acccatgtct  780
gcagggccta gcaagttaaa ataaggctag tccgttatca acttggccaa catgaggatc  840
acccatgtct gcagggccaa gtggcaccga gtcggtgctt tttttgtttt agagctagaa  900
atagcaagtt aaaataaggc tagtccgttt tatgcatgtg gctcccattt atacctggcc  960
ggctttccca tgattccttc atatttgcat atacgataca aggctgttag agagataatt  1020
ggaattaatt tgactgtaaa cacaaagata ttagtacaaa atacgtgacg tagaaagtaa  1080
taatttcttg ggtagtttgc agttttaaaa ttatgtttta aaatggacta tcatatgctt  1140
accgtaactt gaaagtattt cgatttcttg gctttatata tcttgtggaa aggacgaaac  1200
accnnnnnnn nnnnnnnnnn nnngttttag agctaggcca acatgaggat cacccatgtc  1260
tgcagggcct agcaagttaa aataaggcta gtccgttatc aacttggcca acatgaggat  1320
cacccatgtc tgcagggcca agtggcaccg agtcggtgct ttttttgttt tagagctaga  1380
aatagcaagt taaaataagg ctagtccgtt tt                                1412
```

```
SEQ ID NO: 66          moltype = DNA  length = 1414
FEATURE                Location/Qualifiers
misc_feature           1..1414
                       note = Synthetic
source                 1..1414
                       mol_type = other DNA
                       organism = synthetic construct
SEQUENCE: 66
tttcccatga ttccttcata tttgcatata cgatacaagg ctgttagaga gataattgga  60
attaatttga ctgtaaacac aaagatatta gtacaaaata cgtgacgtag aaagtaataa  120
tttcttgggt agtttgcagt tttaaaatta tgttttaaaa tggactatca tatgcttacc  180
gtaacttgaa agtatttcga tttcttggct ttatatatct tgtggaaagg acgaaacacc  240
gacggttgcc ctctttccca agttttagag ctaggccaac atgaggatca cccatgtctg  300
cagggcctag caagttaaaa taaggctagt ccgttatcaa cttggccaac atgaggatca  360
cccatgtctg cagggccaag tggcaccgag tcggtgcttt ttttgtttta gagctagaaa  420
tagcaagtta aaataaggct agtccgtttt gagctccata agactcggcc ttagaacaag  480
ctttttccca tgattccttc atatttgcat atacgataca aggctgttag agagataatt  540
ggaattaatt tgactgtaaa cacaaagata ttagtacaaa atacgtgacg tagaaagtaa  600
taatttcttg ggtagtttgc agttttaaaa ttatgtttta aaatggacta tcatatgctt  660
accgtaactt gaaagtattt cgatttcttg gctttatata tcttgtggaa aggacgaaac  720
accgactgtc agactcaaag gtgcgtttta gagctaggcc aacatgagga tcacccatgt  780
ctgcagggcc tagcaagtta aaataaggct agtccgttat caacttggcc aacatgagga  840
tcacccatgt ctgcagggcc aagtggcacc gagtcggtgc ttttttttgtt ttagagctag  900
aaatagcaag ttaaaataag gctagtccgt tttatgcatg tggctcccat ttatacctgg  960
ccggctttcc catgattcct tcatatttgc atatacgata caaggctgtt agagagataa  1020
```

```
ttggaattaa tttgactgta aacacaaaga tattagtaca aaatacgtga cgtagaaagt  1080
aataatttct tgggtagttt gcagttttaa aattatgttt taaaatggac tatcatatgc  1140
ttaccgtaac ttgaaagtat ttcgatttct tggctttata tatcttgtgg aaaggacgaa  1200
acaccgacaa taagtagtct tactcgtttt agagctaggc caacatgagg atcacccatg  1260
tctgcagggc ctagcaagtt aaaataaggc tagtccgtta tcaacttggc caacatgagg  1320
atcacccatg tctgcagggc caagtggcac cgagtcggtg cttttttgt tttagagcta  1380
gaaatagcaa gttaaaataa ggctagtccg tttt                              1414

SEQ ID NO: 67          moltype = DNA  length = 1490
FEATURE                Location/Qualifiers
misc_feature           1..1490
                       note = Synthetic
misc_feature           28..267
                       note = hU6 promoter
misc_feature           269..288
                       note = Guide1
misc_feature           289..425
                       note = SAM Tracr
misc_feature           426..477
                       note = Extended terminator
misc_feature           511..750
                       note = hU6 promoter
misc_feature           752..771
                       note = Guide2
misc_feature           772..908
                       note = SAM Tracr
misc_feature           909..960
                       note = Extended terminator
misc_feature           993..1232
                       note = hU6 promoter
misc_feature           1233..1252
                       note = Guide3
misc_feature           1253..1389
                       note = SAM Tracr
misc_feature           1390..1441
                       note = Extended terminator
source                 1..1490
                       mol_type = other DNA
                       organism = synthetic construct
SEQUENCE: 67
gctagccata agactcggcc ttagaacttt cccatgattc cttcatattt gcatatacga  60
tacaaggctg ttagagagat aattggaatt aatttgactg taaacacaaa gatattagta  120
caaaatacgt gacgtagaaa gtaataattt cttgggtagt ttgcagtttt aaaattatgt  180
tttaaaatgg actatcatat gcttaccgta acttgaaagt atttcgattt cttggcttta  240
tatatcttgt ggaaaggacg aaacaccgac ggttgccctc tttcccaagt tttagagcta  300
ggccaacatg aggatcaccc atgtctgcag ggcctagcaa gttaaaataa ggctagtccg  360
ttatcaactt ggccaacatg aggatcaccc atgtctgcag ggccaagtgg caccgagtcg  420
gtgctttttt tgttttagag ctagaaatag caagttaaaa taaggctagt ccgttttgag  480
ctccataaga ctcggcctta gaacaagctt tttcccatga ttccttcata tttgcatata  540
cgatacaagg ctgttagaga gataattgga attaatttga ctgtaaacac aaagatatta  600
gtacaaaata cgtgacgtag aaagtaataa tttcttgggt agtttgcagt tttaaaatta  660
tgttttaaaa tggactatca tatgcttacc gtaacttgaa agtatttcga tttcttggct  720
ttatatatct tgtggaaagg acgaaacacc gactgtcaga ctcaaaggtg cgttttagag  780
ctaggccaac atgaggatca cccatgtctg cagggcctag caagttaaaa taaggctagt  840
ccgttatcaa cttggccaac atgaggatca cccatgtctg cagggccaag tggcaccgag  900
tcggtgcttt ttttgtttta gagctagaaa tagcaagtta aaataaggct agtccgtttt  960
atgcatgtgg ctcccattta tacctggccg gctttcccat gattccttca tatttgcata  1020
tacgatacaa ggctgttaga gagataattg gaattaattt gactgtaaac acaaagatat  1080
tagtacaaaa tacgtgacgt agaaagtaat aatttcttgg gtagtttgca gttttaaaat  1140
tatgttttaa aatggactat catatgctta ccgtaacttg aaagtatttc gatttcttgg  1200
ctttatatat cttgtggaaa ggacgaaaca ccgacaataa gtagtcttac tcgttttaga  1260
gctaggccaa catgaggatc acccatgtct gcagggccta gcaagttaaa ataaggctag  1320
tccgttatca acttggccaa catgaggatc acccatgtct gcagggccaa gtggcaccga  1380
gtcggtgctt tttttgtttt agagctagaa atagcaagtt aaaataaggc tagtccgttt  1440
tggtcaccca gtgaggaagc taggacagac ctaggacggt tgcctgcagg             1490

SEQ ID NO: 68          moltype = DNA  length = 490
FEATURE                Location/Qualifiers
misc_feature           1..490
                       note = Synthetic
misc_feature           1..318
                       note = mU6 promoter
misc_feature           320..339
                       note = Guide1
misc_feature           340..476
                       note = SAM Tracr
misc_feature           477..482
                       note = Small terminator
```

```
source                1..490
                      mol_type = other DNA
                      organism = synthetic construct
SEQUENCE: 68
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccga cggttgccct ctttcccaag ttttagagct aggccaacat  360
gaggatcacc catgtctgca gggcctagca agttaaaata aggctagtcc gttatcaact  420
tggccaacat gaggatcacc catgtctgca gggccaagtg gcaccgagtc ggtgcttttt  480
ttctagaggc                                                         490

SEQ ID NO: 69         moltype = DNA  length = 490
FEATURE               Location/Qualifiers
misc_feature          1..490
                      note = Synthetic
misc_feature          1..318
                      note = mU6 promoter
misc_feature          320..339
                      note = Guide2
misc_feature          340..476
                      note = SAM Tracr
misc_feature          477..482
                      note = Small terminator
source                1..490
                      mol_type = other DNA
                      organism = synthetic construct
SEQUENCE: 69
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccga ctgtcagact caaaggtgcg ttttagagct aggccaacat  360
gaggatcacc catgtctgca gggcctagca agttaaaata aggctagtcc gttatcaact  420
tggccaacat gaggatcacc catgtctgca gggccaagtg gcaccgagtc ggtgcttttt  480
ttctagaggc                                                         490

SEQ ID NO: 70         moltype = DNA  length = 489
FEATURE               Location/Qualifiers
misc_feature          1..489
                      note = Synthetic
misc_feature          1..318
                      note = mU6 promoter
misc_feature          319..338
                      note = Guide3
misc_feature          339..475
                      note = SAM Tracr
misc_feature          476..481
                      note = Small terminator
source                1..489
                      mol_type = other DNA
                      organism = synthetic construct
SEQUENCE: 70
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccga caataagtag tcttactcgt tttagagcta ggccaacatg  360
aggatcaccc atgtctgcag ggcctagcaa gttaaaataa ggctagtccg ttatcaactt  420
ggccaacatg aggatcaccc atgtctgcag ggccaagtgg caccgagtcg gtgctttttt  480
tctagaggc                                                          489

SEQ ID NO: 71         moltype = DNA  length = 1491
FEATURE               Location/Qualifiers
misc_feature          1..1491
                      note = Synthetic
misc_feature          28..267
                      note = hU6 promoter
misc_feature          269..288
                      note = Guide1
misc_feature          289..425
                      note = SAM Tracr
misc_feature          426..477
                      note = Extended terminator
```

```
misc_feature          511..750
                      note = hU6 promoter
misc_feature          752..771
                      note = Guide2
misc_feature          772..908
                      note = SAM Tracr
misc_feature          909..960
                      note = Extended terminator
misc_feature          993..1232
                      note = hU6 promoter
misc_feature          1234..1253
                      note = Guide3
misc_feature          1254..1390
                      note = SAM Tracr
misc_feature          1391..1442
                      note = Extended terminator
source                1..1491
                      mol_type = other DNA
                      organism = synthetic construct
SEQUENCE: 71
gctagccata agactcggcc ttagaacttt cccatgattc cttcatattt gcatatacga  60
tacaaggctg ttagagagat aattggaatt aatttgactg taaacacaaa gatattagta  120
caaaatacgt gacgtagaaa gtaataattt cttgggtagt ttgcagtttt aaaattatgt  180
tttaaaatgg actatcatat gcttaccgta acttgaaagt atttcgattt cttggcttta  240
tatatcttgt ggaaaggacg aaacaccgaa gcggtgaaat tctgtggggt tttagagcta  300
ggccaacatg aggatcaccc atgtctgcag ggcctagcaa gttaaaataa ggctagtccg  360
ttatcaactt ggccaacatg aggatcaccc atgtctgcag ggccaagtgg caccgagtcg  420
gtgctttttt tgttttagag ctagaaatag caagttaaaa taaggctagt ccgttttgag  480
ctccataaga ctcggcctta gaacaagctt tttcccatga ttccttcata tttgcatata  540
cgatacaagg ctgttagaga gataattgga attaatttga ctgtaaacac aaagatatta  600
gtacaaaata cgtgacgtag aaagtaataa tttcttgggt agtttgcagt tttaaaatta  660
tgttttaaaa tggactatca tatgcttacc gtaacttgaa agtatttcga tttcttggct  720
ttatatatct tgtggaaagg acgaaacacc gcactcaaac agcaacgcgg ggttttagag  780
ctaggccaac atgaggatca cccatgtctg cagggcctag caagttaaaa taaggctagt  840
ccgttatcaa cttggccaac atgaggatca cccatgtctg cagggccaag tggcaccgag  900
tcggtgcttt ttttgtttta gagctagaaa tagcaagtta aaataaggct agtccgtttt  960
atgcatgtgg ctcccattta tacctggccg gctttcccat gattccttca tatttgcata  1020
tacgatacaa ggctgttaga gagataattg gaattaattt gactgtaaac acaaagatat  1080
tagtacaaaa tacgtgacgt agaaagtaat aatttcttgg gtagtttgca gttttaaaat  1140
tatgttttaa aatggactat catatgctta ccgtaacttg aaagtatttc gatttcttgg  1200
ctttatatat cttgtggaaa ggacgaaaca ccgcttcacc tcactgagcg ggggttttag  1260
agctaggcca acatgaggat cacccatgtc tgcagggcct agcaagttaa aataaggcta  1320
gtccgttatc aacttggcca acatgaggat cacccatgtc tgcagggcca agtggcaccg  1380
agtcggtgct ttttttgttt tagagctaga aatagcaagt taaaataagg ctagtccgtt  1440
ttggtcaccc agtgaggaag ctaggacaga cctaggacgg ttgcctgcag g           1491

SEQ ID NO: 72         moltype = DNA  length = 490
FEATURE               Location/Qualifiers
misc_feature          1..490
                      note = Synthetic
misc_feature          1..318
                      note = mU6 promoter
misc_feature          320..339
                      note = Guide1
misc_feature          340..476
                      note = SAM Tracr
misc_feature          477..482
                      note = Small terminator
source                1..490
                      mol_type = other DNA
                      organism = synthetic construct
SEQUENCE: 72
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccga agcggtgaaa ttctgtgggg ttttagagct aggccaacat  360
gaggatcacc catgtctgca gggcctagca agttaaaata aggctagtcc gttatcaact  420
tggccaacat gaggatcacc catgtctgca gggccaagtg gcaccgagtc ggtgcttttt  480
ttctagaggc                                                         490

SEQ ID NO: 73         moltype = DNA  length = 490
FEATURE               Location/Qualifiers
misc_feature          1..490
                      note = Synthetic
misc_feature          1..318
                      note = mU6 promoter
```

```
misc_feature          320..339
                      note = Guide2
misc_feature          340..476
                      note = SAM Tracr
misc_feature          477..482
                      note = Small terminator
source                1..490
                      mol_type = other DNA
                      organism = synthetic construct
SEQUENCE: 73
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccgc actcaaacag caacgcgggg ttttagagct aggccaacat  360
gaggatcacc catgtctgca gggcctagca agttaaaata aggctagtcc gttatcaact  420
tggccaacat gaggatcacc catgtctgca gggccaagtg gcaccgagtc ggtgcttttt  480
ttctagaggc                                                        490

SEQ ID NO: 74         moltype = DNA  length = 489
FEATURE               Location/Qualifiers
misc_feature          1..489
                      note = Synthetic
misc_feature          1..318
                      note = mU6 promoter
misc_feature          319..338
                      note = Guide3
misc_feature          339..475
                      note = SAM Tracr
misc_feature          476..481
                      note = Small terminator
source                1..489
                      mol_type = other DNA
                      organism = synthetic construct
SEQUENCE: 74
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccct tcacctcact gagcgggggt tttagagcta ggccaacatg  360
aggatcaccc atgtctgcag ggcctagcaa gttaaaataa ggctagtccg ttatcaactt  420
ggccaacatg aggatcaccc atgtctgcag ggccaagtgg caccgagtcg gtgctttttt  480
tctagaggc                                                         489

SEQ ID NO: 75         moltype = DNA  length = 20
FEATURE               Location/Qualifiers
misc_feature          1..20
                      note = Synthetic
source                1..20
                      mol_type = other DNA
                      organism = synthetic construct
SEQUENCE: 75
aagcggtgaa attctgtggg                                             20

SEQ ID NO: 76         moltype = DNA  length = 20
FEATURE               Location/Qualifiers
misc_feature          1..20
                      note = Synthetic
source                1..20
                      mol_type = other DNA
                      organism = synthetic construct
SEQUENCE: 76
cactcaaaca gcaacgcggg                                             20

SEQ ID NO: 77         moltype = DNA  length = 20
FEATURE               Location/Qualifiers
misc_feature          1..20
                      note = Synthetic
source                1..20
                      mol_type = other DNA
                      organism = synthetic construct
SEQUENCE: 77
cttcacctca ctgagcgggg                                             20

SEQ ID NO: 78         moltype = RNA  length = 157
FEATURE               Location/Qualifiers
```

```
misc_feature          1..157
                      note = Synthetic
source                1..157
                      mol_type = other RNA
                      organism = synthetic construct
SEQUENCE: 78
aagcggtgaa attctgtggg gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 79         moltype = RNA  length = 157
FEATURE               Location/Qualifiers
misc_feature          1..157
                      note = Synthetic
source                1..157
                      mol_type = other RNA
                      organism = synthetic construct
SEQUENCE: 79
cactcaaaca gcaacgcggg gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 80         moltype = RNA  length = 157
FEATURE               Location/Qualifiers
misc_feature          1..157
                      note = Synthetic
source                1..157
                      mol_type = other RNA
                      organism = synthetic construct
SEQUENCE: 80
cttcacctca ctgagcgggg gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 81         moltype = RNA  length = 20
FEATURE               Location/Qualifiers
misc_feature          1..20
                      note = Synthetic
source                1..20
                      mol_type = other RNA
                      organism = synthetic construct
SEQUENCE: 81
aagcggtgaa attctgtggg                                              20

SEQ ID NO: 82         moltype = RNA  length = 20
FEATURE               Location/Qualifiers
misc_feature          1..20
                      note = Synthetic
source                1..20
                      mol_type = other RNA
                      organism = synthetic construct
SEQUENCE: 82
cactcaaaca gcaacgcggg                                              20

SEQ ID NO: 83         moltype = RNA  length = 20
FEATURE               Location/Qualifiers
misc_feature          1..20
                      note = Synthetic
source                1..20
                      mol_type = other RNA
                      organism = synthetic construct
SEQUENCE: 83
cttcacctca ctgagcgggg                                              20

SEQ ID NO: 84         moltype = DNA  length = 1415
FEATURE               Location/Qualifiers
misc_feature          1..1415
                      note = Synthetic
source                1..1415
                      mol_type = other DNA
                      organism = synthetic construct
SEQUENCE: 84
tttcccatga ttccttcata tttgcatata cgatacaagg ctgttagaga gataattgga  60
attaatttga ctgtaaacac aaagatatta gtacaaaata cgtgacgtag aaagtaataa  120
tttcttgggt agtttgcagt tttaaaatta tgttttaaaa tggactatca tatgcttacc  180
gtaacttgaa agtatttcga tttcttggct ttatatatct tgtggaaagg acgaaacacc  240
gaagcggtga aattctgtgg ggttttagag ctaggccaac atgaggatca cccatgtctg  300
cagggcctag caagttaaaa taaggctagt ccgttatcaa cttggccaac atgaggatca  360
cccatgtctg cagggccaag tggcaccgag tcggtgcttt ttttgtttta gagctagaaa  420
```

```
tagcaagtta aaataaggct agtccgtttt gagctccata agactcggcc ttagaacaag  480
ctttttccca tgattccttc atatttgcat atacgataca aggctgttag agagataatt  540
ggaattaatt tgactgtaaa cacaaagata ttagtacaaa atacgtgacg tagaaagtaa  600
taatttcttg ggtagtttgc agttttaaaa ttatgtttta aaatggacta tcatatgctt  660
accgtaactt gaaagtattt cgatttcttg gctttatata tcttgtggaa aggacgaaac  720
accgcactca aacagcaacg cggggtttta gagctaggcc aacatgagga tcacccatgt  780
ctgcagggcc tagcaagtta aaataaggct agtccgttat caacttggcc aacatgagga  840
tcacccatgt ctgcagggcc aagtggcacc gagtcggtgc ttttttgtt ttagagctag  900
aaatagcaag ttaaaataag gctagtccgt tttatgcatg tggctcccat ttatacctgg  960
ccggctttcc catgattcct tcatatttgc atatacgata caaggctgtt agagagataa  1020
ttggaattaa tttgactgta aacacaaaga tattagtaca aaatacgtga cgtagaaagt  1080
aataatttct tgggtagttt gcagttttaa aattatgttt taaaatggac tatcatatgc  1140
ttaccgtaac ttgaaagtat ttcgatttct tggctttata tatcttgtgg aaaggacgaa  1200
acaccgcttc acctcactga gcgggggttt tagagctagg ccaacatgag gatcacccat  1260
gtctgcaggg cctagcaagt taaaataagg ctagtccgtt atcaacttgg ccaacatgag  1320
gatcacccat gtctgcaggg ccaagtggca ccgagtcggt gcttttttg ttttagagct  1380
agaaatagca agttaaaata aggctagtcc gtttt                           1415
```

```
SEQ ID NO: 85          moltype = DNA  length = 1490
FEATURE                Location/Qualifiers
misc_feature           1..1490
                       note = Synthetic
misc_feature           28..267
                       note = hU6 promoter
misc_feature           268..287
                       note = Guide1
misc_feature           288..424
                       note = SAM Tracr
misc_feature           425..476
                       note = Extended terminator
misc_feature           510..749
                       note = hU6 promoter
misc_feature           751..770
                       note = Guide2
misc_feature           771..907
                       note = SAM Tracr
misc_feature           908..959
                       note = Extended terminator
misc_feature           992..1231
                       note = hU6 promoter
misc_feature           1233..1252
                       note = Guide3
misc_feature           1253..1389
                       note = SAM Tracr
misc_feature           1390..1441
                       note = Extended terminator
source                 1..1490
                       mol_type = other DNA
                       organism = synthetic construct
SEQUENCE: 85
gctagccata agactcggcc ttagaacttt cccatgattc cttcatattt gcatatacga  60
tacaaggctg ttagagagat aattggaatt aatttgactg taaacacaaa gatattagta  120
caaaatacgt gacgtagaaa gtaataattt cttgggtagt ttgcagtttt aaaattatgt  180
tttaaaatgg actatcatat gcttaccgta acttgaaagt atttcgattt cttggcttta  240
tatatcttgt ggaaaggacg aaacaccgaa gagtcatggg tcacagggtt ttagagctag  300
gccaacatga ggatcaccca tgtctgcagg gcctagcaag ttaaaataag gctagtccgt  360
tatcaacttg gccaacatga ggatcaccca tgtctgcagg gccaagtggc accgagtcgg  420
tgcttttttt gttttagagc tagaaatagc aagttaaaat aaggctagtc cgttttgagc  480
tccataagac tcggccttag aacaagcttt ttcccatgat tccttcatat ttgcatatac  540
gatacaaggc tgttagagag ataattggaa ttaatttgac tgtaaacaca aagatattag  600
tacaaaatac gtgacgtaga aagtaataat ttcttgggta gtttgcagtt ttaaaattat  660
gttttaaaat ggactatcat atgcttaccg taacttgaaa gtatttcgat ttcttggctt  720
tatatatctt gtggaaagga cgaaacaccg caggcggggt gccaactcag gttttagagc  780
taggccaaca tgaggatcac ccatgtctgc agggcctagc aagttaaaat aaggctagtc  840
cgttatcaac ttggccaaca tgaggatcac ccatgtctgc agggccaagt ggcaccgagt  900
cggtgctttt tttgttttag agctagaaat agcaagttaa aataaggcta gtccgtttta  960
tgcatgtggc tcccatttat acctggccgg ctttcccatg attccttcat atttgcatat  1020
acgatacaag gctgttagag agataattgg aattaatttg actgtaaaca caaagatatt  1080
agtacaaaat acgtgacgta gaaagtaata atttcttggg tagtttgcag ttttaaaatt  1140
atgttttaaa atggactatc atatgcttac cgtaacttga aagtatttcg atttcttggc  1200
tttatatatc ttgtggaaag gacgaaacac cgaatattaa ctaacttctc ctgttttaga  1260
gctaggccaa catgaggatc acccatgtct gcagggccta gcaagttaaa ataaggctag  1320
tccgttatca acttggccaa catgaggatc acccatgtct gcagggccaa gtggcaccga  1380
gtcggtgctt tttttgtttt agagctagaa atagcaagtt aaaataaggc tagtccgttt  1440
tggtcaccca gtgaggaagc taggacagac ctaggacggt tgcctgcagg            1490
```

```
SEQ ID NO: 86          moltype = DNA  length = 489
FEATURE                Location/Qualifiers
```

```
misc_feature          1..489
                      note = Synthetic
misc_feature          1..318
                      note = mU6 promoter
misc_feature          319..338
                      note = Guide1
misc_feature          339..475
                      note = SAM Tracr
misc_feature          476..481
                      note = Small terminator
source                1..489
                      mol_type = other DNA
                      organism = synthetic construct
SEQUENCE: 86
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccga agagtcatgg gtcacagggt tttagagcta ggccaacatg  360
aggatcaccc atgtctgcag ggcctagcaa gttaaaataa ggctagtccg ttatcaactt  420
ggccaacatg aggatcaccc atgtctgcag ggccaagtgg caccgagtcg gtgctttttt  480
tctagaggc                                                          489

SEQ ID NO: 87         moltype = DNA  length = 490
FEATURE               Location/Qualifiers
misc_feature          1..490
                      note = Synthetic
misc_feature          1..318
                      note = mU6 promoter
misc_feature          320..339
                      note = Guide2
misc_feature          340..476
                      note = SAM Tracr
misc_feature          477..482
                      note = Small terminator
source                1..490
                      mol_type = other DNA
                      organism = synthetic construct
SEQUENCE: 87
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccgc aggcggggtg ccaactcagg ttttagagct aggccaacat  360
gaggatcacc catgtctgca gggcctagca agttaaaata aggctagtcc gttatcaact  420
tggccaacat gaggatcacc catgtctgca gggccaagtg gcaccgagtc ggtgcttttt  480
ttctagaggc                                                         490

SEQ ID NO: 88         moltype = DNA  length = 489
FEATURE               Location/Qualifiers
misc_feature          1..489
                      note = Synthetic
misc_feature          1..318
                      note = mU6 promoter
misc_feature          319..338
                      note = Guide3
misc_feature          339..475
                      note = SAM Tracr
misc_feature          476..481
                      note = Small terminator
source                1..489
                      mol_type = other DNA
                      organism = synthetic construct
SEQUENCE: 88
tgtacaaaaa agcaggcttt aaaggaacca attcagtcga ctggatccgg taccaaggtc  60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccaa tattaactaa cttctcctgt tttagagcta ggccaacatg  360
aggatcaccc atgtctgcag ggcctagcaa gttaaaataa ggctagtccg ttatcaactt  420
ggccaacatg aggatcaccc atgtctgcag ggccaagtgg caccgagtcg gtgctttttt  480
tctagaggc                                                          489

SEQ ID NO: 89         moltype = DNA  length = 20
FEATURE               Location/Qualifiers
```

```
misc_feature           1..20
                       note = Synthetic
source                 1..20
                       mol_type = other DNA
                       organism = synthetic construct
SEQUENCE: 89
gaagagtcat gggtcacagg                                              20

SEQ ID NO: 90          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 90
caggcggggt gccaactcag                                              20

SEQ ID NO: 91          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 91
aatattaact aacttctcct                                              20

SEQ ID NO: 92          moltype = RNA  length = 157
FEATURE                Location/Qualifiers
misc_feature           1..157
                       note = Synthetic
source                 1..157
                       mol_type = other RNA
                       organism = synthetic construct
SEQUENCE: 92
gaagagtcat gggtcacagg gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 93          moltype = RNA  length = 157
FEATURE                Location/Qualifiers
misc_feature           1..157
                       note = Synthetic
source                 1..157
                       mol_type = other RNA
                       organism = synthetic construct
SEQUENCE: 93
caggcggggt gccaactcag gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 94          moltype = RNA  length = 157
FEATURE                Location/Qualifiers
misc_feature           1..157
                       note = Synthetic
source                 1..157
                       mol_type = other RNA
                       organism = synthetic construct
SEQUENCE: 94
aatattaact aacttctcct gttttagagc taggccaaca tgaggatcac ccatgtctgc  60
agggcctagc aagttaaaat aaggctagtc cgttatcaac ttggccaaca tgaggatcac  120
ccatgtctgc agggccaagt ggcaccgagt cggtgct                           157

SEQ ID NO: 95          moltype = RNA  length = 20
FEATURE                Location/Qualifiers
misc_feature           1..20
                       note = Synthetic
source                 1..20
                       mol_type = other RNA
                       organism = synthetic construct
SEQUENCE: 95
gaagagtcat gggtcacagg                                              20

SEQ ID NO: 96          moltype = RNA  length = 20
FEATURE                Location/Qualifiers
misc_feature           1..20
                       note = Synthetic
```

-continued

```
source                1..20
                      mol_type = other RNA
                      organism = synthetic construct
SEQUENCE: 96
caggcggggt gccaactcag                                         20

SEQ ID NO: 97         moltype = RNA  length = 20
FEATURE               Location/Qualifiers
misc_feature          1..20
                      note = Synthetic
source                1..20
                      mol_type = other RNA
                      organism = synthetic construct
SEQUENCE: 97
aatattaact aacttctcct                                         20

SEQ ID NO: 98         moltype = DNA  length = 1414
FEATURE               Location/Qualifiers
misc_feature          1..1414
                      note = Synthetic
source                1..1414
                      mol_type = other DNA
                      organism = synthetic construct
SEQUENCE: 98
tttcccatga ttccttcata tttgcatata cgatacaagg ctgttagaga gataattgga  60
attaatttga ctgtaaacac aaagatatta gtacaaaata cgtgacgtag aaagtaataa  120
tttcttgggt agtttgcagt tttaaaatta tgttttaaaa tggactatca tatgcttacc  180
gtaacttgaa agtatttcga tttcttggct ttatatatct tgtggaaagg acgaaacacc  240
gaagagtcat gggtcacagg gttttagagc taggccaaca tgaggatcac ccatgtctgc  300
agggcctagc aagttaaaat aaggctagtc cgttatcaac ttggccaaca tgaggatcac  360
ccatgtctgc agggccaagt ggcaccgagt cggtgctttt tttgttttag agctagaaat  420
agcaagttaa aataaggcta gtccgttttg agctccataa gactcggcct tagaacaagc  480
tttttcccat gattccttca tatttgcata tacgatacaa ggctgttaga gagataattg  540
gaattaattt gactgtaaac acaaagatat tagtacaaaa tacgtgacgt agaaagtaat  600
aatttcttgg gtagtttgca gttttaaaat tatgttttaa aatggactat catatgctta  660
ccgtaacttg aaagtatttc gatttcttgg ctttatatat cttgtggaaa ggacgaaaca  720
ccgcaggcgg ggtgccaact caggttttag agctaggcca acatgaggat cacccatgtc  780
tgcagggcct agcaagttaa aataaggcta gtccgttatc aacttggcca acatgaggat  840
cacccatgtc tgcagggcca agtggcaccg agtcggtgct ttttttgttt tagagctaga  900
aatagcaagt taaaataagg ctagtccgtt ttatgcatgt ggctcccatt tatacctggc  960
cggctttccc atgattcctt catatttgca tatacgatac aaggctgtta gagagataat  1020
tggaattaat ttgactgtaa acacaaagat attagtacaa aatacgtgac gtagaaagta  1080
ataatttctt gggtagtttg cagttttaaa attatgtttt aaaatggact atcatatgct  1140
taccgtaact tgaaagtatt tcgatttctt ggctttatat atcttgtgga aaggacgaaa  1200
caccgaatat taactaactt ctcctgtttt agagctaggc caacatgagg atcacccatg  1260
tctgcagggc ctagcaagtt aaaataaggc tagtccgtta tcaacttggc caacatgagg  1320
atcacccatg tctgcagggc caagtggcac cgagtcggtg ctttttttgt tttagagcta  1380
gaaatagcaa gttaaaataa ggctagtccg tttt                         1414
```